US005798259A

United States Patent [19]

Yazawa et al.

[11] Patent Number: 5,798,259

[45] Date of Patent: *Aug. 25, 1998

[54] GENE CODING FOR EICOSAPENTAENOIC ACID SYNTHESIZING ENZYMES AND PROCESS FOR PRODUCTION OF EICOSAPENTAENOIC ACID

[75] Inventors: Kazunaga Yazawa; Akiko Yamada; Seishi Kato, all of Sagamihara; Kiyosi Kondo, Yamato, all of Japan

[73] Assignee: Sagami Chemical Research Center, Tokyo, Japan

[ * ] Notice: The term of this patent shall not extend beyond the expiration date of Pat. No. 5,683,898.

[21] Appl. No.: 752,929

[22] Filed: Nov. 20, 1996

Related U.S. Application Data

[63] Continuation-in-part of Ser. No. 375,709, Jan. 20, 1995, Pat. No. 5,683,898, which is a continuation-in-part of Ser. No. 178,251, Jan. 10, 1994, abandoned.

[30] Foreign Application Priority Data

May 15, 1992 [JP] Japan .................................... 4-147945

[51] Int. Cl.$^{6}$ ............................ C12N 15/52; C12N 1/21; C12P 7/64

[52] U.S. Cl. ...................... 435/252.3; 435/134; 435/136; 435/183; 435/325; 435/320.1; 536/23.1; 536/23.2

[58] Field of Search ................................ 536/23.2, 23.1; 435/183, 136, 134, 252.3, 325, 320.1

[56] References Cited

FOREIGN PATENT DOCUMENTS

| | | |
|---|---|---|
| 223 877 | 4/1990 | Japan . |
| 297 393 | 4/1990 | Japan . |
| 228 023 | 11/1990 | Japan . |

*Primary Examiner*—Rebecca E. Prouty
*Attorney, Agent, or Firm*—Foley & Lardner

[57] ABSTRACT

There is provided an advantageous process for production of EPA by a gene recombinant technique wherein genes coding for biosynthesis enzymes for eicosapentaenoic acid (EPA) useful as pharmaceuticals, agrochemicals, foods, feeds or the like is obtained from microorganisms.

EPA is produced by obtaining genes coding for eicosapentaenoic acid (EPA) biosynthesis enzymes, constructing a plasmid by joining the genes to a vector, transforming *E. coli* with the plasmid, and culturing the transformed *E. coli*.

14 Claims, 3 Drawing Sheets

XhoI
AscI
PacI
SnaBI
SnaBI
BbeI
BbeI
Sa II
NruI
PstI
EcoT22I
NheI
SpeI
Aat II
ORF
2
3
4
5
6
7
8
9
10
pEPA△2
pEPA△4,5
pEPA△6
pEPA△7
pEPA△8
pXS-BS
pPA-NEB
pAA-NEB
XhoI-AscI DELETION
SnaBI-SnaBI DELETION
BbeI-BbeI DELETION
Sa II-NruI DELETION
PstI-EcoT22I DELETION
XhoI-SpeI/BS
PacI-Aat II/NEB
AscI-Aat II/NEB
Stem & Roop XhoI-Aat II FRAGMENT OF pEPA
XhoI
BstBI
PacI
EcoRI
XbaI
BstBI
Dra III
NheI
SpeI
Aat II
ORF
2
3
4
5
6
7
8
9
10
① ORF3/pSTV28
② Δ2,4,5/pNEB
③ Δ2,3,5/pNEB
ORF2,5 DELETION
ORF2,4,5 DELETION
ORF2,5,10 DELETION
ORF2,4,5,10 DELETION
INSERTED REGION
DELETED REGION

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
( A ) LENGTH: 37895 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( A ) ORGANISM: Shewanella putrefaciens SCRC-2874 (FERM BP- 1625)

( x i ) SEQUENCE DESCRIPTION: SEQ ID NO:1:

```
GATCTCTTAC AAAGAAACTA TCTCAATGTG AATTTAACCT TAATTCCGTT TAATTACGGC    60
CTGATAGAGC ATCACCCAAT CAGCCATAAA ACTGTAAAGT GGGTACTCAA AGGTGGCTGG   120
GCGATTCTTC TCAAATACAA AGTGCCCAAC CCAAGCAAAT CCATATCCGA TAACAGGTAA   180
AAGTAGCAAT AAACCCCAGC GCTGAGTTAG TAATACATAA GCGAATAATA GGATCACTAA   240
ACTACTGCCG AAATAGTGTA ATATTCGACA GTTTCTATGC TGATGTTGAG ATAAATAAAA   300
AGGGTAAAAT TCAGCAAAAG AACGATAGCG CTTACTCATT ACTCACACCT CGGTAAAAAA   360
GCAACTCGCC ATTAACTTGG CCAATCGTCA GTTGTTCTAT CGTCTCAAAG TTATGCCGAC   420
TAAATAACTC TATATGTGCA TTATGATTAG CAAAAACTCC GATACCATCA AGATGAAGTT   480
GTTCATCACA CCAACTCAAA ACTGCGTCGA TAAGCTTACT GCCATAGCCC TTGCCTTGCT   540
CCACATTTGC GATAGCAATA AACTGTAAAA TGCCACATTG GCCACTTGGT AAGCTCTCTA   600
```

-continued

```
TAATCTGATT TTCTTTGTTA ATAAGTGCCT GAGTTGAATA CCAACCAGTA CTTAACAACA   660
TCTTTAAACG CCAATGCCAA AAACGCGCTT CACCTAAGGG AACCTGCTGA GTCACTATGC   720
AGGCTACGCC TATCAATCTA TCCCCAACGA ACATACCAAT AAGTGCTTGC TCCTGTTGCC   780
AGAGCTCATT GAGTTCTTCT CGAATAGCCC CGCGAAGCTT TTGCTCATAC TGCGCTTGAT   840
CACCACTAAA AAGTGTTTCG ATAAAAAAGG GATCATCATG ATAGGCGTTA TAGAGAATAG   900
AGGCTGCTAT GCGTAAATCT TCTGCCGTGA GATAAACTGC ACGACACTCT TCCATGGCTT   960
GATCTTCCAT TGTTATTGTC CTTGACCTTG ATCACACAAC ACCAATGTAA CAAGACTGTA  1020
TAGAAGTGCA ATTAATAATC AATTCGTGCA TTAAGCAGGT CAGCATTTCT TTGCTAAACA  1080
AGCTTTATTG GCTTTGACAA AACTTTGCCT AGACTTTAAC GATAGAAATC ATAATGAAAG  1140
AGAAAAGCTA CAACCTAGAG GGGAATAATC AAACAACTGC TAAGATCTAG ATAATGTAAT  1200
AAACACCGAG TTTATCGACC ATACTTAGAT AGAGTCATAG CAACGAGAAT AGTTATGGAT  1260
ACAACGCCGC AAGATCTATC ACACCTGTTT TTACAGCTAG GATTAGCAAA TGATCAACCC  1320
GCAATTGAAC AGTTTATCAA TGACCATCAA TTAGCGGACA ATATATTGCT ACATCAAGCA  1380
AGCTTTTGGA GCCCATCGCA AAAGCACTTC TTAATTGAGT CATTTAATGA AGATGCCCAG  1440
TGGACCGAAG TCATCGACCA CTTAGACACC TTATTAAGAA AAAACTAACC ATTACAACAG  1500
CAACTTTAAA TTTTGCCGTA AGCCATCTCC CCCCACCCCA CAACAGCGTT GTTGCTTATG  1560
ACCACTGGAG TACATTCGTC TTTAGTCGTT TTACCATCAC CATGGGTACG TTGAGTGCGA  1620
TAAAAAAGCA CATAAACTTC TTTATCGGCC TGAATATAGG CTTCGTTAAA ATCAGCTGTT  1680
CCCATTAAAG TAACCACTTG CTCTTTACTC ATGCCTAGAG ATATCTTTGT CAAATTGTCA  1740
CGGTTTTTAT CTTGAGTTTT CTCCCAAGCA CCGTGATTAT CCCAGTCAGA TTCCCCATCA  1800
CCAACATTGA CCACACAGCC CGTTAGCCCT AAGCTTGCAA TCCCAAAACA TGCTAAACCT  1860
AATAATTTAT TTTTCATTTT AACTTCCTGT TATGACATTA TTTTTGCTTA GAAGAAAAGC  1920
AACTTACATG CCAAAACACA AGCTGTTGTT TTAAATGACT TTATTTATTA TTAGCCTTTT  1980
AGGATATGCC TAGAGCAATA ATAATTACCA ATGTTTAAGG AATTTGACTA ACTATGAGTC  2040
CGATTGAGCA AGTGCTAACA GCTGCTAAAA AAATCAATGA ACAAGGTAGA GAACCAACAT  2100
TAGCATTGAT TAAAACCAAA CTTGGTAATA GCATCCCAAT GCGCGAGTTA ATCCAAGGTT  2160
TGCAACAGTT TAAGTCTATG AGTGCAGAAG AAAGACAAGC AATACCTAGC AGCTTAGCAA  2220
CAGCAAAAGA AACTCAATAT GGTCAATCAA GCTTATCTCA ATCTGAACAA GCTGATAGGA  2280
TCCTCCAGCT AGAAAACGCC CTCAATGAAT TAAGAAACGA ATTTAATGGG CTAAAAAGTC  2340
AATTTGATAA CTTACAACAA AACCTGATGA ATAAAGAGCC TGACACCAAA TGCATGTAAT  2400
TGAACTACGA TTTGAATGTT TTGATAACAC CACGATTACT GCAGCAGAAA AAGCCATTAA  2460
TGGTTTGCTT GAAGCTTATC GAGCCAATGG CCAGGTTCTA GGTCGTGAAT TTGCCGTTGC  2520
ATTTAACGAT GGTGAGTTTA AAGCACGCAT GTTAACCCCA GAAAAAAGCA GCTTATCTAA  2580
ACGCTTTAAT AGTCCTTGGG TAAATAGTGC ACTCGAAGAG CTAACCGAAG CCAAATTGCT  2640
TGCGCCACGT GAAAAGTATA TTGGCCAAGA TATTAATTCT GAAGCATCTA GCCAAGACAC  2700
ACCAAGTTGG CAGCTACTTT ACACAAGTTA TGTGCACATG TGCTCACCAC TAAGAAATGG  2760
CGACACCTTG CAGCCTATTC CACTGTATCA AATTCCAGCA ACTGCCAACG GCGATCATAA  2820
ACGAATGATC CGTTGGCAAA CAGAATGGCA AGCTTGTGAT GAATTGCAAA TGGCCGCAGC  2880
TACTAAAGCT GAATTTGCCG CACTTGAAGA GCTAACCAGT CATCAGAGTG ATCTATTTAG  2940
GCGTGGTTGG GACTTACGTG GCAGAGTCGA ATACTTGACG AAAATTCCGA CCTATTACTA  3000
```

-continued

```
TTTATACCGT GTTGGCGGTG AAAGCTTAGC AGTAGAAAAG CAGCGCTCTT GTCCTAAGTG 3060
TGGCAGTCAA GAATGGCTGC TCGATAAACC ATTATTGGAT ATGTTCCATT TTCGCTGTGA 3120
CACCTGCCGC ATCGTATCTA ATATCTCTTG GGACCATTTA TAACTCTTCC GAGTCTTATC 3180
ACACTAGAGT TTAGTCAGCA TAAAAATGGC GCTTATATTT CAATTAAAAG AAATATAAGC 3240
GCCATTTTCA TCGATACTAT ATATCAGCAG ACTATTTTCC GCGTAAATTA GCCCACATTA 3300
ATTTCATTCT TTGCCAGATC CCTGGATGAT CTAGTTGTGG CATCGACTCT TCAATAGGTT 3360
TAACCGCAGG TGTAACCCTT GGAGTCAATT CGTTTATAAA CTCGTTTAAA CTGTCACTTA 3420
ATTTAACGCT TTGTACTTCA CCTGGAATTT CAATCCATAC GCTGCCATCA CTATTATTAA 3480
CCGTCAACAT TTTATCTTCA TCATCAAGAA TACCAATAAA CCAAGTCGGC TCTTGCTTAA 3540
GCTTTCTCTT CATCATTAAA TGACCAATGA TGTTTTGTTG TAAGTATTCA AAATCAGTTT 3600
GATCCCACAC TTGGATTAGC TCACCTTGGC CCCATTGTGA GTCAAAAAAT AGCGGTGCAG 3660
AAAAATGACT GCCAAAAAAT GGATTAATTT CTGCAGATAA TGTCATTTCA AGTGCTGTTT 3720
CAACATTAGC AAATTCACCA GGTTGTTGAC GTACAACCGA TTGCCAAAAC ACTGCGCCAT 3780
CGGAGCCCGC TTCGGCGACA ACACACTCAG ACTTTTGTCC TTGCGCATAA TATCTTGGCT 3840
GTTCACCAAG CTTATCCATG TAGGCTTGTT GATATTTAGA TAAAAAAAGA TCTAAAGCAG 3900
GTAAAGAAGA CACTTAAGCC AGTTCCAAAA TCAGTTATAA TAGGGGTCTA TTTTGACATG 3960
GAAACCGTAT TGATGACACA ACATCATGAT CCCTACAGTA ACGCCCCCGA ACTTTCTGAA 4020
TTAACTTTAG GAAAGTCGAC CGGTTATCAA GAGCAGTATG ATGCATCTTT ACTACAAGCG 4080
TGCCGCGTAA ATTAAACCGT GATGCTATCG GTCTAACCAA TGAGCTACCT TTTCATGGCT 4140
GTGATATTTG GACTGGCTAC GAACTGTCTT GGCTAAATGC TAAAGGCAAG CCAATGATTG 4200
CTATTGCAGA CTTTAACCTA AGTTTTGATA GTAAAAATCT GATCGAGTCT AAGTCGTTTA 4260
AGCTGTATTT AAACAGCTAT AACCAAACAC GATTTGATAG CGTTCAAGCG GTTCAAGAAC 4320
GTTTAACTGA AGACTTAAGC GCCTGTGCCC AAGGCACAGT TACGGTAAAA GTGATTGAAC 4380
CTAAGCAATT TAACCACCTG AGAGTGGTTG ATATGCCAGG TACCTGCATT GACGATTTAG 4440
ATATTGAAGT TGATGACTAT AGCTTTAACT CTGACTATCT CACCGACAGT GTTGATGACA 4500
AAGTCATGGT TGCTGAAACG CTAACGTCAA ACTTATTGAA ATCAAACTGC CTAATCACTT 4560
CTCAGCCTGA CTGGGGTACA GTGATGATCC GTTATCAAGG GCCTAAGATA GACCGTGAAA 4620
AGCTACTTAG ATATCTGATT TCATTTAGAC AGCACAATGA ATTTCATGAG CAGTGTGTTG 4680
AGCGTATATT TGTTGATTTA AAGCACTATT GCCAATGTGC CAAACTTACT GTCTATGCAC 4740
GTTATACCCG CCGTGGTGGT TTAGATATCA ACCCATATCG TAGCGACTTT GAAAACCCTG 4800
CAGAAAATCA GCGCCTAGCG AGACAGTAAT TGATTGCAGT ACCTACAAAA AACAATGCCT 4860
ATAAGCCAAG CTTATGGGCA TTTTTATATT ATCAACTTGT CATCAAACCT CAGCCGCCAA 4920
GCCTTTTAGT TTTATCGCTA AATTAAGCCG CTCTCTCAGC CAAATATTTG CAGGATTTTG 4980
CTGTAATTTA TGGCTCCACA CCATGAAATA CTCTATCGGC TCTACCGCAA AAGGTAAGTC 5040
AAATACCTGT AAGCCAAACA GCTTGGCATA TTCGTCAGTG TGGGCTTTTG ACGCGATAGC 5100
TAACGCATCA CTTTTTGAGG CAACCGACAT CATACTTAAT ATTGATGATT GCTCGCTGTG 5160
CATTTGCCTT GCCGGTAACA CCTGTTTAGT CAGCAAGTCG GCAACACTTA AATTGTAGCG 5220
GCGCATCTTA AAAATAATAT GCTTTTCATT AAAGTATTGC TCTTGCGTCA ACCCACCTTG 5280
GATCCTTGGG TGAGCATTTC GTGCCACACA AACTAATTTA TCCTGCATTA CTTTTTGACT 5340
CTTAAATGCC GCAGATTCTG GCAGCCAAAT ATCTAAGGCT AAATCCACCT TTTCTAGTTG 5400
```

-continued

TAGGTCCATC TGCAACTCTT CTTCAATGAG CGGCGGCTCA CGAAATACAA TATTAATTGC 5460

AGTGCCCTGT AACACTTGCT CAATTTGATC TTGCAAGAGT TGTATTGCCG ACTCGCTGGC 5520

ATACACATAA AAAGTTCGCT CACTTGAAGT GGGGTCAAAT GCTTCAAAGC TAGTCGCAAC 5580

TTGCTCAATT GTTGACATAG CGCCCGCGAG CTGTTGATAA AGCGTCATCG CACTTGCGGT 5640

AGGTTTAACT CCCCTACCCA CTCGAGTAAA CAACTCTTCT CCAACAATAC TTTTTAGCCT 5700

CGAAATCGCA TTACTAACCG ACGACTGAGT CAAATCCAGC TCTTCTGCCG CCCGGCTAAA 5760

AGATGAGGTG CGATACACCG CAGTAAAAAC GCGAAATAAA TTAAGATCAA AAGCTTTTTG 5820

CTGCGACATA AATCAGCTAT CTCCTTATCC TTATCCTTAT CCTTATAAAA AGTTAGCTCC 5880

AGAGCACTCT AGCTCAAAAA CAACTCAGCG TATTAAGCCA ATATTTTGGG AACTCAATTA 5940

ATATTCATAA TAAAAGTATT CATAATATAA ATACCAAGTC ATAATTTAGC CCTAATTATT 6000

AATCAATTCA AGTTACCTAT ACTGGCCTCA ATTAAGCAAA TGTCTCATCA GTCTCCCTGC 6060

AACTAAATGC AATATTGAGA CATAAAGCTT TGAACTGATT CAATCTTACG AGGGTAACTT 6120

ATGAAACAGA CTCTAATGGC TATCTCAATC ATGTCGCTTT TTTCATTCAA TGCGCTAGCA 6180

GCGCAACATG AACATGACCA CATCACTGTT GATTACGAAG GGAAAGCCGC AACAGAACAC 6240

ACCATAGCTC ACAACCAAGC TGTAGCTAAA ACACTTAACT TTGCCGACAC GCGTGCATTT 6300

GAGCAATCGT CTAAAAATCT AGTCGCCAAG TTTGATAAAG CAACTGCCGA TATATTACGT 6360

GCCGAATTTG CTTTTATTAG CGATGAAATC CCTGACTCGG TTAACCCGTC TCTCTACCGT 6420

CAGGCTCAGC TTAATATGGT GCCTAATGGT CTGTATAAAG TGAGCGATGG CATTTACCAG 6480

GTCCGCGGTA CCGACTTATC TAACCTTACA CTTATCCGCA GTGATAACGG TTGGATAGCA 6540

TACGATGTTT TGTTAACCAA AGAAGCAGCA AAAGCCTCAC TACAATTTGC GTTAAAGAAT 6600

CTACCTAAAG ATGGCGATTT ACCCGTTGTT GCGATGATTT ACTCCCATAG CCATGCGGAC 6660

CACTTTGGCG GAGCTCGCGG TGTTCAAGAG ATGTTCCCTG ATGTCAAAGT CTACGGCTCA 6720

GATAACATCA CTAAAGAAAT TGTCGATGAG AACGTACTTG CCGGTAACGC CATGAGCCGC 6780

CGCGCAGCTT ATCAATACGG CGCAACACTG GGCAAACATG ACCACGGTAT TGTTGATGCT 6840

GCGCTAGGTA AAGGTCTATC AAAAGGTGAA ATCACTTACG TCGCCCCAGA CTACACCTTA 6900

AACAGTGAAG GCAAATGGGA AACGCTGACG ATTGATGGTC TAGAGATGGT GTTTATGGAT 6960

GCCTCGGGCA CCGAAGCTGA GTCAGAAATG ATCACTTATA TTCCCTCTAA AAAAGCGCTC 7020

TGGACGGCGG AGCTTACCTA TCAAGGTATG CACAACATTT ATACGCTGCG CGGCGCTAAA 7080

GTACGTGATG CGCTCAAGTG GTCAAAAGAT ATCAACGAAA TGATCAATGC CTTTGGTCAA 7140

GATGTCGAAG TGCTGTTTGC CTCGCACTCT GCGCCAGTGT GGGGTAACCA AGCGATCAAC 7200

GATTTCTTAC GCCTACAGCG TGATAACTAC GGCCTAGTGC ACAATCAAAC CTTGAGACTT 7260

GCCAACGATG GTGTCGGTAT ACAAGATATT GGCGATGCGA TTCAAGACAC GATTCCAGAG 7320

TCTATCTACA AGACGTGGCA TACCAATGGT TACCACGGCA CTTATAGCCA TAACGCTAAA 7380

GCGGTTTATA ACAAGTATCT AGGCTACTTC GATATGAACC CAGCCAACCT TAATCCGCTG 7440

CCAACCAAGC AAGAATCTGC CAAGTTTGTC GAATACATGG GCGGCGCAGA TGCCGCAATT 7500

AAGCGCGCTA AAGATGATTA CGCTCAAGGT GAATACCGCT TTGTTGCAAC GGCATTAAAT 7560

AAGGTGGTGA TGGCCGAGCC AGAAAATGAC TCCGCTCGTC AATTGCTAGC CGATACCTAT 7620

GAGCAACTTG GTTATCAAGC AGAAGGGGCT GGCTGGAGAA ACATTTACTT AACTGGCGCA 7680

CAAGAGCTAC GAGTAGGTAT TCAAGCTGGC GCGCCTAAAA CCGCATCGGC AGATGTCATC 7740

AGTGAAATGG ACATGCCGAC TCTATTTGAC TTCCTCGCGG TGAAGATTGA TAGTCAACAG 7800

-continued

```
GCGGCTAAGC ACGGCTTAGT TAAGATGAAT GTTATCACCC CTGATACTAA AGATATTCTC   7860
TATATTGAGC TAAGCAACGG TAACTTAAGC AACGCAGTGG TCGACAAAGA GCAAGCAGCT   7920
GACGCAAACC TTATGGTTAA TAAAGCTGAC GTTAACCGCA TCTTACTTGG CCAAGTAACC   7980
CTAAAAGCGT TATTAGCCAG CGGCGATGCC AAGCTCACTG GTGATAAAAC GGCATTTAGT   8040
AAAATAGCCG ATAGCATGGT CGAGTTTACA CCTGACTTCG AAATCGTACC AACGCCTGTT   8100
AAATGAGGCA TTAATCTCAA CAAGTGCAAG CTAGACATAA AAATGGGGCG ATTAGACGCC   8160
CCATTTTTTA TGCAATTTTG AACTAGCTAG TCTTAGCTGA AGCTCGAACA ACAGCTTTAA   8220
AATTCACTTC TTCTGCTGCA ATACTTATTT GCTGACACTG ACCAATACTC AGTGCAAAAC   8280
GATAACTATC ATCAAGATGG CCCAGTAAAC AATGCCAATT ATCAGCAGCG TTCATTTGCT   8340
GTTCTTTAGC CTCAATCAAA CCTAAACCAG ACTTTTGTGG CTCAGCGTTA GGCTTATTAG   8400
AACTCGACTC TAGTAAAGCA AGACCAATAT CTTGTTTTAA CAAAACCTGT CGCTGATTAA   8460
GTTGATGCTC AACCTTGTGA TCCGCAATAG CATCGGAAAT ATCAACACAA TGGCTCAAGC   8520
TTTTAGGTGC ATTAACTCCA AGAAAAGTTT CGCTCAGTGC AGAGAAGTCA AACGCAAAAG   8580
ATTTTAGCGA TAATGCCAGC CCAAGTCCTT TCGCTTTAAT GTAAGACTCC TTGAGCGCCC   8640
ACAAATCAAA AAAGCGGTCT CGCTGCAAGG CCTCTGGTAA CGCTAACAAG GCTCGCTTTT   8700
CTGATTCAGA GAAATAATGA CTAAGAATAG AGTGGATATT GGTGCTGTTA CGGCAACGCT   8760
CAATGTCGAC GCCAAACTCA ATACTAGCAG AGTCAGTTTC CTCCTTGCTT GCCTGACTGG   8820
CGCCTTTATT ATCAGCAGTG CAAATGCCTA CTAATAGCCA ATCTCCACTA TGACTCACAT   8880
TAAAGTGGAC CCCGGTTTGA GCAAATTGCG CATCACTCAA TCTAGGCTTA CCTTTGTCGC   8940
CATATTCAAA GCGCCATTCA TTGGGGCGTA TTTCACTATG TTGTGACAAT AAAGCGCGCA   9000
AATAGCCTCT TACCATTAAA CCTTGAGTTT TAGCTTCTTG TTTAATGTAG CGATTAACCT   9060
TAATTAACTC ATCTTCAGGC AGCCATGACT TAACCAACTC TGTAGTCTGG TTATCGCACT   9120
CTTGTATTGT TAACGGACAG AAGTATAAGG AAATCAATCG AGAAGTTAGC AATTTTTCAG   9180
GACACTCTTT AAAGCAACAA ACATAACCCC TATTTTTACC AATTTAAGAT CAAAACTAAA   9240
GCCAAAACTA ATTGAGAATA GTGTCAAACT AGCTTTAAAG GAAAAAAATA TAAAAAGAAC   9300
ATTATACTTG TATAAATTAT TTTACACACC AAAGCCATGA TCTTCACAAA ATTAGCTCCC   9360
TCTCCCTAAA ACAAGATTGA ATAAAAAAAT AAACCTTAAC TTTCATATAG ATAAAACAAA   9420
CCAATGGGAT AAAGTATATT GAATTCATTT TTAAGGAAAA ATTCAAATTG AATTCAAGCT   9480
CTTCAGTAAA AGCATATTTT GCCGTTAGTG TGAAAAAAAA CAAATTTAAA AACCAACATA   9540
GAACAAATAA GCAGACAATA AAACCAAGGC GCAACACAAA CAACGCGCTT ACAATTTTCA   9600
CAAAAAAGCA ACAAGAGTAA CGTTTAGTAT TTGGATATGG TTATTGTAAT TGAGAATTTT   9660
ATAACAATTA TATTAAGGGA ATGAGTATGT TTTTAAATTC AAAACTTTCG CGCTCAGTCA   9720
AACTTGCCAT ATCCGCAGGC TTAACAGCCT CGCTAGCTAT GCCTGTTTTT GCAGAAGAAA   9780
CTGCTGCTGA AGAACAAATA GAAAGAGTCG CAGTGACCGG ATCGCGAATC GCTAAAGCAG   9840
AGCTAACTCA ACCAGCTCCA GTCGTCAGCC TTTCAGCCGA AGAACTGACA AAATTTGGTA   9900
ATCAAGATTT AGGTAGCGTA CTAGCAGAAT TACCTGCTAT TGGTGCAACC AACACTATTA   9960
TTGGTAATAA CAATAGCAAC TCAAGCGCAG GTGTTAGCTC AGCAGACTTG CGTCGTCTAG  10020
GTGCTAACAG AACCTTAGTA TTAGTCAACG GTAAGCGCTA CGTTGCCGGC CAACCGGGCT  10080
CAGCTGAGGT AGATTTGTCA ACTATACCAA CTAGCATGAT CTCGCGAGTT GAGATTGTAA  10140
CCGGCGGTGC TTCAGCAATT TATGGTTCGG ACGCTGTATC AGGTGTTATC AACGTTATCC  10200
```

-continued

```
TTAAAGAAGA CTTTGAAGGC TTTGAGTTTA ACGCACGTAC TAGCGGTTCT ACTGAAAGTG 10260
TAGGCACTCA AGAGCACTCT TTTGACATTT TGGGTGGTGC AAACGTTGCA GATGGACGTG 10320
GTAATGTAAC CTTCTACGCA GGTTATGAAC GTACAAAAGA AGTCATGGCT ACCGACATTC 10380
GCCAATTCGA TGCTTGGGGA ACAATTAAAA ACGAAGCCGA TGGTGGTGAA GATGATGGTA 10440
TTCCAGACAG ACTACGTGTA CCACGAGTTT ATTCTGAAAT GATTAATGCT ACCGGTGTTA 10500
TCAATGCATT TGGTGGTGGA ATTGGTCGCT CAACCTTTGA CAGTAACGGC AATCCTATTG 10560
CACAACAAGA ACGTGATGGG ACTAACAGCT TTGCATTTGG TTCATTCCCT AATGGCTGTG 10620
ACACATGTTT CAACACTGAA GCATACGAAA ACTATATTCC AGGGGTAGAA AGAATAAACG 10680
TTGGCTCATC ATTCAACTTT GATTTTACCG ATAACATTCA ATTTTACACT GACTTCAGAT 10740
ATGTAAAGTC AGATATTCAG CAACAATTTC AGCCTTCATT CCGTTTTGGT AACATTAATA 10800
TCAATGTTGA AGATAACGCC TTTTTGAATG ACGACTTGCG TCAGCAAATG CTCGATGCGG 10860
GTCAAACCAA TGCTAGTTTT GCCAAGTTTT TTGATGAATT AGGAAATCGC TCAGCAGAAA 10920
ATAAACGCGA ACTTTTCCGT TACGTAGGTG GCTTTAAAGG TGGCTTTGAT ATTAGCGAAA 10980
CCATATTTGA TTACGACCTT TACTATGTTT ATGGCGAGAC TAATAACCGT CGTAAAACCC 11040
TTAATGACCT AATTCCTGAT AACTTTGTCG CAGCTGTCGA CTCTGTTATT GATCCTGATA 11100
CTGGCTTAGC AGCGTGTCGC TCACAAGTAG CAAGCGCTCA AGGCGATGAC TATACAGATC 11160
CCGCGTCTGT AAATGGTAGC GACTGTGTTG CTTATAACCC ATTTGGCATG GGTCAAGCTT 11220
CAGCAGAAGC CCGCGACTGG GTTTCTGCTG ATGTGACTCG TGAAGACAAA ATAACTCAAC 11280
AAGTGATTGG TGGTACTCTC GGTACCGATT CTGAAGAACT ATTTGAGCTT CAAGGTGGTG 11340
CAATCGCTAT GGTTGTTGGT TTTGAATACC GTGAAGAAAC GTCTGGTTCA ACAACCGATG 11400
AATTTACTAA AGCAGGTTTC TTGACAAGCG CTGCAACGCC AGATTCTTAT GGCGAATACG 11460
ACGTGACTGA GTATTTTGTT GAGGTGAACA TCCCAGTACT AAAAGAATTA CCTTTTGCAC 11520
ATGAGTTGAG CTTTGACGGT GCATACCGTA ATGCTGATTA CTCACATGCC GGTAAGACTG 11580
AAGCATGGAA AGCTGGTATG TTCTACTCAC CATTAGAGCA ACTTGCATTA CGTGGTACGG 11640
TAGGTGAAGC AGTACGAGCA CCAAACATTG CAGAAGCCTT TAGTCCACGC TCTCCTGGTT 11700
TTGGCCGCGT TTCAGATCCA TGTGATGCAG ATAACATTAA TGACGATCCG GATCGCGTGT 11760
CAAACTGTGC AGCATTGGGG ATCCCTCCAG GATTCCAAGC TAATGATAAC GTCAGTGTAG 11820
ATACCTTATC TGGTGGTAAC CCAGATCTAA AACCTGAAAC ATCAACATCC TTTACAGGTG 11880
GTCTTGTTTG GACACCAACG TTTGCTGACA ATCTATCATT CACTGTCGAT TATTATGATA 11940
TTCAAATTGA GGATGCTATT TTGTCAGTAG CCACCCAGAC TGTGGCTGAT AACTGTGTTG 12000
ACTCAACTGG CGGACCTGAC ACCGACTTCT GTAGTCAAGT TGATCGTAAT CCAACGACCT 12060
ATGATATTGA ACTTGTTCGC TCTGGTTATC TAAATGCCGC GGCATTGAAT ACCAAAGGTA 12120
TTGAATTTCA AGCTGCATAC TCATTAGATC TAGAGTCTTT CAACGCGCCT GGTGAACTAC 12180
GCTTCAACCT ATTGGGGAAC CAATTACTTG AACTAGAACG TCTTGAATTC CAAAATCGTC 12240
CTGATGAGAT TAATGATGAA AAAGGCGAAG TAGGTGATCC AGAGCTGCAG TTCCGCCTAG 12300
GCATCGATTA CCGTCTAGAT GATCTAAGTG TTAGCTGGAA CACGCGTTAT ATTGATAGCG 12360
TAGTAACTTA TGATGTCTCT GAAAATGGTG GCTCTCCTGA AGATTTATAT CCAGGCCACA 12420
TAGGCTCAAT GACAACTCAT GACTTGAGCG CTACATACTA CATCAATGAG AACTTCATGA 12480
TTAACGGTGG TGTACGTAAC CTATTTGACG CACTTCCACC TGGATACACT AACGATGCGC 12540
TATATGATCT AGTTGGTCGC CGTGCATTCC TAGGTATTAA GGTAATGATG TAATTAATTA 12600
```

-continued

```
TTACGCCTCT AACTAATAAA AATGCAATCT CTTCGTAGAG ATTGCATTTT TTTATGAAAT 12660
CCAATCTTAA ACTGGTTCTC CGAGCATCTT ACGCCTTAAA AACCCCGCCC CTCAATGTAA 12720
CGCCAAAGTT AATTGCTTAC ACGCACTTAC ACAAACGAAC AATTTCATTA ACACGAGACA 12780
CAGCTCACGC TTTTTATTTT ACCCTTGATT TTACTACATA AAATTGCGTT TTAGCGCACA 12840
AGTGTTCTCC CAAGCTGGTC GTATCTGTAA TTATTCAGTC CCAGGTGATT GTATTGACCC 12900
ATAAGCTCAG GTAGTCTGCT CTGCCATTAG CTAAACAATA TTGACAAAAT GGCGATAAAA 12960
TGTGGCTTAG CGCTAAGTTC ACCGTAAGTT TTATCGGCAT TAAGTCCCAA CAGATTATTA 13020
ACGGAAACCC GCTAAACTGA TGGCAAAAAT AAATAGTGAA CACTTGGATG AAGCTACTAT 13080
TACTTCGAAT AAGTGTACGC AAACAGAGAC TGAGGCTCGG CATAGAAATG CCACTACAAC 13140
ACCTGAGATG CGCCGATTCA TACAAGAGTC GGATCTCAGT GTTAGCCAAC TGTCTAAAAT 13200
ATTAAATATC AGTGAAGCTA CCGTACGTAA GTGGCGCAAG CGTGACTCTG TCGAAAACTG 13260
TCCTAATACC CCGCACCATC TCAATACCAC GCTAACCCCT TTGCAAGAAT ATGTGGTTGT 13320
GGGCCTGCGT TATCAATTGA AAATGCCATT AGACAGATTG CTCAAAGCAA CCCAAGAGTT 13380
TATCAATCCA AACGTGTCGC GCTCAGGTTT AGCAAGATGT TTGAAGCGTT ATGGCGTTTC 13440
ACGGGTGAGT GATATCCAAA GCCCACACGT ACCAATGCGC TACTTTAATC AAATTCCAGT 13500
CACTCAAGGC AGCGATGTGC AAACCTACAC CCTGCACTAT GAAACGCTGG CAAAAACCTT 13560
AGCCTTACCT AGTACCGATG GTGACAATGT GGTGCAAGTG GTGTCTCTCA CCATTCCACC 13620
AAAGTTAACC GAAGAAGCAC CCAGTTCAAT TTTGCTCGGC ATTGATCCTC ATAGCGACTG 13680
GATCTATCTC GACATATACC AAGATGGCAA TACACAAGCC ACGAATAGAT ATATGGCTTA 13740
TGTGCTAAAA CACGGGCCAT TCCATTTACG AAAGTTACTC GTGCGTAACT ATCACACCTT 13800
TTTACAGCGC TTTCCTGGAG CGACGCAAAA TCGCCGCCCC TCTAAAGATA TGCCTGAAAC 13860
AATCAACAAG ACGCCTGAAA CACAGGCACC CAGTGGAGAC TCATAATGAG CCAGACCTCT 13920
AAACCTACAA ACTCAGCAAC TGAGCAAGCA CAAGACTCAC AAGCTGACTC TCGTTTAAAT 13980
AAACGACTAA AAGATATGCC AATTGCTATT GTTGGCATGG CGAGTATTTT TGCAAACTCT 14040
CGCTATTTGA ATAAGTTTTG GGACTTAATC AGCGAAAAAA TTGATGCGAT TACTGAATTA 14100
CCATCAACTC ACTGGCAGCC TGAAGAATAT TACGACGCAG ATAAAACCGC AGCAGACAAA 14160
AGCTACTGTA AACGTGGTGG CTTTTTGCCA GATGTAGACT TCAACCCAAT GGAGTTTGGC 14220
CTGCCGCCAA ACATTTTGGA ACTGACCGAT TCATCGCAAC TATTATCACT CATCGTTGCT 14280
AAAGAAGTGT TGGCTGATGC TAACTTACCT GAGAATTACG ACCGCGATAA AATTGGTATC 14340
ACCTTAGGTG TCGGCGGTGG TCAAAAAATT AGCCACAGCC TAACAGCGCG TCTGCAATAC 14400
CCAGTATTGA AGAAAGTATT CGCCAATAGC GGCATTAGTG ACACCGACAG CGAAATGCTT 14460
ATCAAGAAAT TCCAAGACCA ATATGTACAC TGGGAAGAAA ACTCGTTCCC AGGTTCACTT 14520
GGTAACGTTA TTGCGGGCCG TATCGCCAAC CGCTTCGATT TTGGCGGCAT GAACTGTGTG 14580
GTTGATGCTG CCTGTGCTGG ATCACTTGCT GCTATGCGTA TGGCGCTAAC AGAGCTAACT 14640
GAAGGTCGCT CTGAAATGAT GATCACCGGT GGTGTGTGTA CTGATAACTC ACCCTCTATG 14700
TATATGAGCT TTTCAAAAAC GCCCGCCTTT ACCACTAACG AAACCATTCA GCCATTTGAT 14760
ATCGACTCAA AAGGCATGAT GATTGGTGAA GGTATTGGCA TGGTGGCGCT AAAGCGTCTT 14820
GAAGATGCAG AGCGCGATGG CGACCGCATT TACTCTGTAA TTAAAGGTGT GGGTGCATCA 14880
TCTGACGGTA AGTTTAAATC AATCTATGCC CCTCGCCCAT CAGGCCAAGC TAAAGCACTT 14940
AACCGTGCCT ATGATGACGC AGGTTTTGCG CCGCATACCT TAGGTCTAAT TGAAGCTCAC 15000
```

GGAACAGGTA CTGCAGCAGG TGACGCGGCA GAGTTTGCCG GCCTTTGCTC AGTATTTGCT 15060

GAAGGCAACG ATACCAAGCA ACACATTGCG CTAGGTTCAG TTAAATCACA AATTGGTCAT 15120

ACTAAATCAA CTGCAGGTAC AGCAGGTTTA ATTAAAGCTG CTCTTGCTTT GCATCACAAG 15180

GTACTGCCGC CGACCATTAA CGTTAGTCAG CCAAGCCCTA AACTTGATAT CGAAAACTCA 15240

CCGTTTTATC TAAACACTGA GACTCGTCCA TGGTTACCAC GTGTTGATGG TACGCCGCGC 15300

CGCGCGGGTA TTAGCTCATT TGGTTTTGGT GGCACTAACT TCCATTTTGT ACTAGAAGAG 15360

TACAACCAAG AACACAGCCG TACTGATAGC GAAAAAGCTA AGTATCGTCA ACGCCAAGTG 15420

GCGCAAAGCT TCCTTGTTAG CGCAAGCGAT AAAGCATCGC TAATTAACGA GTTAAACGTA 15480

CTAGCAGCAT CTGCAAGCCA AGCTGAGTTT ATCCTCAAAG ATGCAGCAGC AAACTATGGC 15540

GTACGTGAGC TTGATAAAAA TGCACCACGG ATCGGTTTAG TTGCAAACAC AGCTGAAGAG 15600

TTAGCAGGCC TAATTAAGCA AGCACTTGCC AAACTAGCAG CTAGCGATGA TAACGCATGG 15660

CAGCTACCTG GTGGCACTAG CTACCGCGCC GCTGCAGTAG AAGGTAAAGT TGCCGCACTG 15720

TTTGCTGGCC AAGGTTCACA ATATCTCAAT ATGGGCCGTG ACCTTACTTG TTATTACCCA 15780

GAGATGCGTC AGCAATTTGT AACTGCAGAT AAAGTATTTG CCGCAAATGA TAAAACGCCG 15840

TTATCGCAAA CTCTGTATCC AAAGCCTGTA TTTAATAAAG ATGAATTAAA GGCTCAAGAA 15900

GCCATTTTGA CCAATACCGC CAATGCCCAA AGCGCAATTG GTGCGATTTC AATGGGTCAA 15960

TACGATTTGT TTACTGCGGC TGGCTTTAAT GCCGACATGG TTGCAGGCCA TAGCTTTGGT 16020

GAGCTAAGTG CACTGTGTGC TGCAGGTGTT ATTTCAGCTG ATGACTACTA CAAGCTGGCT 16080

TTTGCTCGTG GTGAGGCTAT GGCAACAAAA GCACCGGCTA AAGACGGCGT TGAAGCAGAT 16140

GCAGGAGCAA TGTTTGCAAT CATAACCAAG AGTGCTGCAG ACCTTGAAAC CGTTGAAGCC 16200

ACCATCGCTA AATTTGATGG GGTGAAAGTC GCTAACTATA ACGCGCCAAC GCAATCAGTA 16260

ATTGCAGGCC CAACAGCAAC TACCGCTGAT GCGGCTAAAG CGCTAACTGA GCTTGGTTAC 16320

AAAGCGATTA ACCTGCCAGT ATCAGGTGCA TTCCACACTG AACTTGTTGG TCACGCTCAA 16380

GCGCCATTTG CTAAAGCGAT TGACGCAGCC AAATTTACTA AAACAAGCCG AGCACTTTAC 16440

TCAAATGCAA CTGGCGGACT TTATGAAAGC ACTGCTGCAA AGATTAAAGC CTCGTTTAAG 16500

AAACATATGC TTCAATCAGT GCGCTTTACT AGCCAGCTAG AAGCCATGTA CAACGACGGC 16560

GCCCGTGTAT TTGTTGAATT TGGTCCAAAG AACATCTTAC AAAAATTAGT TCAAGGCACG 16620

CTTGTCAACA CTGAAAATGA AGTTTGCACT ATCTCTATCA ACCCTAATCC TAAAGTTGAT 16680

AGTGATCTGC AGCTTAAGCA AGCAGCAATG CAGCTAGCGG TTACTGGTGT GGTACTCAGT 16740

GAAATTGACC CATACCAAGC CGATATTGCC GCACCAGCGA AAAAGTCGCC AATGAGCATT 16800

TCGCTTAATG CTGCTAACCA TATCAGCAAA GCAACTCGCG CTAAGATGGC CAAGTCTTTA 16860

GAGACAGGTA TCGTCACCTC GCAAATAGAA CATGTTATTG AAGAAAAAAT CGTTGAAGTT 16920

GAGAAACTGG TTGAAGTCGA AAAGATCGTC GAAAAAGTGG TTGAAGTAGA GAAAGTTGTT 16980

GAGGTTGAAG CTCCTGTTAA TTCAGTGCAA GCCAATGCAA TTCAAACCCG TTCAGTTGTC 17040

GCTCCAGTAA TAGAGAACCA AGTCGTGTCT AAAAACAGTA AGCCAGCAGT CCAGAGCATT 17100

AGTGGTGATG CACTCAGCAA CTTTTTTGCT GCACAGCAGC AAACCGCACA GTTGCATCAG 17160

CAGTTCTTAG CTATTCCGCA GCAATATGGT GAGACGTTCA CTACGCTGAT GACCGAGCAA 17220

GCTAAACTGG CAAGTTCTGG TGTTGCAATT CCAGAGAGTC TGCAACGCTC AATGGAGCAA 17280

TTCCACCAAC TACAAGCGCA AACACTACAA AGCCACACCC AGTTCCTTGA GATGCAAGCG 17340

GGTAGCAACA TTGCAGCGTT AAACCTACTC AATAGCAGCC AAGCAACTTA CGCTCCAGCC 17400

-continued

```
ATTCACAATG AAGCGATTCA AAGCCAAGTG GTTCAAAGCC AAACTGCAGT CCAGCCAGTA 17460
ATTTCAACAC AAGTTAACCA TGTGTCAGAG CAGCCAACTC AAGCTCCAGC TCCAAAAGCG 17520
CAGCCAGCAC CTGTGACAAC TGCAGTTCAA ACTGCTCCGG CACAAGTTGT TCGTCAAGCC 17580
GCACCAGTTC AAGCCGCTAT TGAACCGATT AATACAAGTG TTGCGACTAC AACGCCTTCA 17640
GCCTTCAGCG CCGAAACAGC CCTGAGCGCA ACAAAAGTCC AAGCCACTAT GCTTGAAGTG 17700
GTTGCTGAGA AAACCGGTTA CCCAACTGAA ATGCTAGAGC TTGAAATGGA TATGGAAGCC 17760
GATTTAGGCA TCGATTCTAT CAAGCGTGTA GAAATTCTTG GCACAGTACA AGATGAGCTA 17820
CCGGGTCTAC CTGAGCTTAG CCCTGAAGAT CTAGCTGAGT GTCGAACGCT AGGCGAAATC 17880
GTTGACTATA TGGGCAGTAA ACTGCCGGCT GAAGGCTCTA TGAATTCTCA GCTGTCTACA 17940
GGTTCCGCAG CTGCGACTCC TGCAGCGAAT GGTCTTTCTG CGGAGAAAGT TCAAGCGACT 18000
ATGATGTCTG TGGTTGCCGA AAAGACTGGC TACCCAACTG AAATGCTAGA GCTTGAAATG 18060
GATATGGAAG CCGATTTAGG CATAGATTCT ATCAAGCGCG TTGAAATTCT TGGCACAGTA 18120
CAAGATGAGC TACCGGGTCT ACCTGAGCTT AGCCCTGAAG ATCTAGCTGA GTGTCGTACT 18180
CTAGGCGAAA TCGTTGACTA TATGAACTCT AAACTCGCTG ACGGCTCTAA GCTGCCGGCT 18240
GAAGGCTCTA TGAATTCTCA GCTGTCTACA AGTGCCGCAG CTGCGACTCC TGCAGCGAAT 18300
GGTCTCTCTG CGGAGAAAGT TCAAGCGACT ATGATGTCTG TGGTTGCCGA AAAGACTGGC 18360
TACCCAACTG AAATGCTAGA ACTTGAAATG GATATGGAAG CTGACCTTGG CATCGATTCA 18420
ATCAAGCGCG TTGAAATTCT TGGCACAGTA CAAGATGAGC TACCGGGTTT ACCTGAGCTA 18480
AATCCAGAAG ATTTGGCAGA GTGTCGTACT CTTGGCGAAA TCGTGACTTA TATGAACTCT 18540
AAACTCGCTG ACGGCTCTAA GCTGCCAGCT GAAGGCTCTA TGCACTATCA GCTGTCTACA 18600
AGTACCGCTG CTGCGACTCC TGTAGCGAAT GGTCTCTCTG CAGAAAAAGT TCAAGCGACC 18660
ATGATGTCTG TAGTTGCAGA TAAAACTGGC TACCCAACTG AAATGCTTGA ACTTGAAATG 18720
GATATGGAAG CCGATTTAGG TATCGATTCT ATCAAGCGCG TTGAAATTCT TGGCACAGTA 18780
CAAGATGAGC TACCGGGTTT ACCTGAGCTA AATCCAGAAG ATCTAGCAGA GTGTCGCACC 18840
CTAGGCGAAA TCGTTGACTA TATGGGCAGT AAACTGCCGG CTGAAGGCTC TGCTAATACA 18900
AGTGCCGCTG CGTCTCTTAA TGTTAGTGCC GTTGCGGCGC CTCAAGCTGC TGCGACTCCT 18960
GTATCGAACG GTCTCTCTGC AGAGAAAGTG CAAAGCACTA TGATGTCAGT AGTTGCAGAA 19020
AAGACCGGCT ACCCAACTGA AATGCTAGAA CTTGGCATGG ATATGGAAGC CGATTTAGGT 19080
ATCGACTCAA TTAAACGCGT TGAGATTCTT GGCACAGTAC AAGATGAGCT ACCGGGTCTA 19140
CCAGAGCTTA ATCCTGAAGA TTTAGCTGAG TGCCGTACGC TGGGCGAAAT CGTTGACTAT 19200
ATGAACTCTA AGCTGGCTGA CGGCTCTAAG CTTCCAGCTG AAGGCTCTGC TAATACAAGT 19260
GCCACTGCTG CGACTCCTGC AGTGAATGGT CTTTCTGCTG ACAAGGTACA GGCGACTATG 19320
ATGTCTGTAG TTGCTGAAAA GACCGGCTAC CCAACTGAAA TGCTAGAACT TGGCATGGAT 19380
ATGGAAGCAG ACCTTGGTAT TGATTCTATT AAGCGCGTTG AAATTCTTGG CACAGTACAA 19440
GATGAGCTCC CAGGTTTACC TGAGCTTAAT CCTGAAGATC TCGCTGAGTG CCGCACGCTT 19500
GGCGAAATCG TTAGCTATAT GAACTCTCAA CTGGCTGATG GCTCTAAACT TTCTACAAGT 19560
GCGGCTGAAG GCTCTGCTGA TACAAGTGCT GCAAATGCTG CAAAGCCGGC AGCAATTTCG 19620
GCAGAACCAA GTGTTGAGCT TCCTCCTCAT AGCGAGGTAG CGCTAAAAAA GCTTAATGCG 19680
GCGAACAAGC TAGAAAATTG TTTCGCCGCA GACGCAAGTG TTGTGATTAA CGATGATGGT 19740
CACAACGCAG GCGTTTTAGC TGAGAAACTT ATTAAACAAG GCCTAAAAGT AGCCGTTGTG 19800
```

```
CGTTTACCGA AAGGTCAGCC TCAATCGCCA CTTTCAAGCG ATGTTGCTAG CTTTGAGCTT 19860
GCCTCAAGCC AAGAATCTGA GCTTGAAGCC AGTATCACTG CAGTTATCGC GCAGATTGAA 19920
ACTCAGGTTG GCGCTATTGG TGGCTTTATT CACTTGCAAC CAGAAGCGAA TACAGAAGAG 19980
CAAACGGCAG TAAACCTAGA TGCGCAAAGT TTTACTCACG TTAGCAATGC GTTCTTGTGG 20040
GCCAAATTAT TGCAACCAAA GCTCGTTGCT GGAGCAGATG CGCGTCGCTG TTTTGTAACA 20100
GTAAGCCGTA TCGACGGTGG CTTTGGTTAC CTAAATACTG ACGCCCTAAA AGATGCTGAG 20160
CTAAACCAAG CAGCATTAGC TGGTTTAACT AAAACCTTAA GCCATGAATG GCCACAAGTG 20220
TTCTGTCGCG CGCTAGATAT TGCAACAGAT GTTGATGCAA CCCATCTTGC TGATGCAATC 20280
ACCAGTGAAC TATTTGATAG CCAAGCTCAG CTACCTGAAG TGGGCTTAAG CTTAATTGAT 20340
GGCAAAGTTA ACCGCGTAAC TCTAGTTGCT GCTGAAGCTG CAGATAAAAC AGCAAAAGCA 20400
GAGCTTAACA GCACAGATAA AATCTTAGTG ACTGGTGGGG CAAAAGGGGT GACATTTGAA 20460
TGTGCACTGG CATTAGCATC TCGCAGCCAG TCTCACTTTA TCTTAGCTGG GCGCAGTGAA 20520
TTACAAGCTT TACCAAGCTG GGCTGAGGGT AAGCAAACTA GCGAGCTAAA ATCAGCTGCA 20580
ATCGCACATA TTATTTCTAC TGGTCAAAAG CCAACGCCTA AGCAAGTTGA AGCCGCTGTG 20640
TGGCCAGTGC AAAGCAGCAT TGAAATTAAT GCCGCCCTAG CCGCCTTTAA CAAAGTTGGC 20700
GCCTCAGCTG AATACGTCAG CATGGATGTT ACCGATAGCG CCGCAATCAC AGCAGCACTT 20760
AATGGTCGCT CAAATGAGAT CACCGGTCTT ATTCATGGCG CAGGTGTACT AGCCGACAAG 20820
CATATTCAAG ACAAGACTCT TGCTGAACTT GCTAAAGTTT ATGGCACTAA AGTCAACGGC 20880
CTAAAAGCGC TGCTCGCGGC ACTTGAGCCA AGCAAAATTA AATTACTTGC TATGTTCTCA 20940
TCTGCAGCAG GTTTTTACGG TAATATCGGC CAAAGCGATT ACGCGATGTC GAACGATATT 21000
CTTAACAAGG CAGCGCTGCA GTTCACCGCT CGCAACCCAC AAGCTAAAGT CATGAGCTTT 21060
AACTGGGGTC CTTGGGATGG CGGCATGGTT AACCCAGCGC TTAAAAAGAT GTTTACCGAG 21120
CGTGGTGTGT ACGTTATTCC ACTAAAAGCA GGTGCAGAGC TATTTGCCAC TCAGCTATTG 21180
GCTGAAACTG GCGTGCAGTT GCTCATTGGT ACGTCAATGC AAGGTGGCAG CGACACTAAA 21240
GCAACTGAGA CTGCTTCTGT AAAAAAGCTT AATGCGGGTG AGGTGCTAAG TGCATCGCAT 21300
CCGCGTGCTG GTGCACAAAA AACACCACTA CAAGCTGTCA CTGCAACGCG TCTGTTAACC 21360
CCAAGTGCCA TGGTCTTCAT TGAAGATCAC CGCATTGGCG GTAACAGTGT GTTGCCAACG 21420
GTATGCGCCA TCGACTGGAT GCGTGAAGCG GCAAGCGACA TGCTTGGCGC TCAAGTTAAG 21480
GTACTTGATT ACAAGCTATT AAAAGGCATT GTATTTGAGA CTGATGAGCC GCAAGAGTTA 21540
ACACTTGAGC TAACGCCAGA CGATTCAGAC GAAGCTACGC TACAAGCATT AATCAGCTGT 21600
AATGGGCGTC CGCAATACAA GGCGACGCTT ATCAGTGATA ATGCCGATAT TAAGCAACTT 21660
AACAAGCAGT TTGATTTAAG CGCTAAGGCG ATTACCACAG CAAAAGAGCT TTATAGCAAC 21720
GGCACCTTGT TCCACGGTCC GCGTCTACAA GGGATCCAAT CTGTAGTGCA GTTCGATGAT 21780
CAAGGCTTAA TTGCTAAAGT CGCTCTGCCT AAGGTTGAAC TTAGCGATTG TGGTGAGTTC 21840
TTGCCGCAAA CCCACATGGG TGGCAGTCAA CCTTTTGCTG AGGACTTGCT ATTACAAGCT 21900
ATGCTGGTTT GGGCTCGCCT TAAAACTGGC TCGGCAAGTT TGCCATCAAG CATTGGTGAG 21960
TTTACCTCAT ACCAACCAAT GGCCTTTGGT GAAACTGGTA CCATAGAGCT TGAAGTGATT 22020
AAGCACAACA AACGCTCACT TGAAGCGAAT GTTGCGCTAT ATCGTGACAA CGGCGAGTTA 22080
AGTGCCATGT TTAAGTCAGC TAAAATCACC ATTAGCAAAA GCTTAAATTC AGCATTTTTA 22140
CCTGCTGTCT TAGCAAACGA CAGTGAGGCG AATTAGTGGA ACAAACGCCT AAAGCTAGTG 22200
```

-continued

```
CGATGCCGCT GCGCATCGCA CTTATCTTAC TGCCAACACC GCAGTTTGAA GTTAACTCTG 22260
TCGACCAGTC AGTATTAGCC AGCTATCAAA CACTGCAGCC TGAGCTAAAT GCCCTGCTTA 22320
ATAGTGCGCC GACACCTGAA ATGCTCAGCA TCACTATCTC AGATGATAGC GATGCAAACA 22380
GCTTTGAGTC GCAGCTAAAT GCTGCGACCA ACGCAATTAA CAATGGCTAT ATCGTCAAGC 22440
TTGCTACGGC AACTCACGCT TTGTTAATGC TGCCTGCATT AAAAGCGGCG CAAATGCGGA 22500
TCCATCCTCA TGCGCAGCTT GCCGCTATGC AGCAAGCTAA ATCGACGCCA ATGAGTCAAG 22560
TATCTGGTGA GCTAAAGCTT GGCGCTAATG CGCTAAGCCT AGCTCAGACT AATGCGCTGT 22620
CTCATGCTTT AAGCCAAGCC AAGCGTAACT TAACTGATGT CAGCGTGAAT GAGTGTTTTG 22680
AGAACCTCAA AAGTGAACAG CAGTTCACAG AGGTTTATTC GCTTATTCAG CAACTTGCTA 22740
GCCGCACCCA TGTGAGAAAA GAGGTTAATC AAGGTGTGGA ACTTGGCCCT AAACAAGCCA 22800
AAAGCCACTA TTGGTTTAGC GAATTTCACC AAAACCGTGT TGCTGCCATC AACTTTATTA 22860
ATGGCCAACA AGCAACCAGC TATGTGCTTA CTCAAGGTTC AGGATTGTTA GCTGCGAAAT 22920
CAATGCTAAA CCAGCAAAGA TTAATGTTTA TCTTGCCGGG TAACAGTCAG CAACAAATAA 22980
CCGCATCAAT AACTCAGTTA ATGCAGCAAT TAGAGCGTTT GCAGGTAACT GAGGTTAATG 23040
AGCTTTCTCT AGAATGCCAA CTAGAGCTGC TCAGCATAAT GTATGACAAC TTAGTCAACG 23100
CAGACAAACT CACTACTCGC GATAGTAAGC CCGCTTATCA GGCTGTGATT CAAGCAAGCT 23160
CTGTTAGCGC TGCAAAGCAA GAGTTAAGCG CGCTTAACGA TGCACTCACA GCGCTGTTTG 23220
CTGAGCAAAC AAACGCCACA TCAACGAATA AAGGCTTAAT CCAATACAAA ACACCGGCGG 23280
GCAGTTACTT AACCCTAACA CCGCTTGGCA GCAACAATGA CAACGCCCAA GCGGGTCTTG 23340
CTTTTGTCTA TCCGGGTGTG GGAACGGTTT ACGCCGATAT GCTTAATGAG CTGCATCAGT 23400
ACTTCCCTGC GCTTTACGCC AAACTTGAGC GTGAAGGCGA TTTAAAGGCG ATGCTACAAG 23460
CAGAAGATAT CTATCATCTT GACCCTAAAC ATGCTGCCCA AATGAGCTTA GGTGACTTAG 23520
CCATTGCTGG CGTGGGGAGC AGCTACCTGT TAACTCAGCT GCTCACCGAT GAGTTTAATA 23580
TTAAGCCTAA TTTTGCATTA GGTTACTCAA TGGGTGAAGC ATCAATGTGG GCAAGCTTAG 23640
GCGTATGGCA AAACCCGCAT GCGCTGATCA GCAAAACCCA AACCGACCCG CTATTTACTT 23700
CTGCTATTTC CGGCAAATTG ACCGCGGTTA GACAAGCTTG GCAGCTTGAT GATACCGCAG 23760
CGGAAATCCA GTGGAATAGC TTTGTGGTTA GAAGTGAAGC AGCGCCGATT GAAGCCTTGC 23820
TAAAAGATTA CCCACACGCT TACCTCGCGA TTATTCAAGG GGATACCTGC GTAATCGCTG 23880
GCTGTGAAAT CCAATGTAAA GCGCTACTTG CAGCACTGGG TAAACGCGGT ATTGCAGCTA 23940
ATCGTGTAAC GGCGATGCAT ACGCAGCCTG CGATGCAAGA GCATCAAAAT GTGATGGATT 24000
TTTATCTGCA ACCGTTAAAA GCAGAGCTTC CTAGTGAAAT AAGCTTTATC AGCGCCGCTG 24060
ATTTAACTGC CAAGCAAACG GTGAGTGAGC AAGCACTTAG CAGCCAAGTC GTTGCTCAGT 24120
CTATTGCCGA CACCTTCTGC CAAACCTTGG ACTTTACCGC GCTAGTACAT CACGCCCAAC 24180
ATCAAGGCGC TAAGCTGTTT GTTGAAATTG GCGCGGATAG ACAAAACTGC ACCTTGATAG 24240
ACAAGATTGT TAAACAAGAT GGTGCCAGCA GTGTACAACA TCAACCTTGT TGCACAGTGC 24300
CTATGAACGC AAAAGGTAGC CAAGATATTA CCAGCGTGAT TAAAGCGCTT GGCCAATTAA 24360
TTAGCCATCA GGTGCCATTA TCGGTGCAAC CATTTATTGA TGGACTCAAG CGCGAGCTAA 24420
CACTTTGCCA ATTGACCAGC CAACAGCTGG CAGCACATGC AAATGTTGAC AGCAAGTTTG 24480
AGTCTAACCA AGACCATTTA CTTCAAGGGG AAGTCTAATG TCATTACCAG ACAATGCTTC 24540
TAACCACCTT TCTGCCAACC AGAAAGGCGC ATCTCAGGCA AGTAAAACCA GTAAGCAAAG 24600
```

```
CAAAATCGCC ATTGTCGGTT TAGCCACTCT GTATCCAGAC GCTAAAACCC CGCAAGAATT 24660
TTGGCAGAAT TTGCTGGATA AACGCGACTC TCGCAGCACC TTAACTAACG AAAAACTCGG 24720
CGCTAACAGC CAAGATTATC AAGGTGTGCA AGGCCAATCT GACCGTTTTT ATTGTAATAA 24780
AGGCGGCTAC ATTGAGAACT TCAGCTTTAA TGCTGCAGGC TACAAATTGC CGGAGCAAAG 24840
CTTAAATGGC TTGGACGACA GCTTCCTTTG GGCGCTCGAT ACTAGCCGTA ACGCACTAAT 24900
TGATGCTGGT ATTGATATCA ACGGCGCTGA TTTAAGCCGC GCAGGTGTAG TCATGGGCGC 24960
GCTGTCGTTC CCAACTACCC GCTCAAACGA TCTGTTTTTG CCAATTTATC ACAGCGCCGT 25020
TGAAAAAGCC CTGCAAGATA AACTAGGCGT AAAGGCATTT AAGCTAAGCC CAACTAATGC 25080
TCATACCGCT CGCGCGGCAA ATGAGAGCAG CCTAAATGCA GCCAATGGTG CCATTGCCCA 25140
TAACAGCTCA AAAGTGGTGG CCGATGCACT TGGCCTTGGC GGCGCACAAC TAAGCCTAGA 25200
TGCTGCCTGT GCTAGTTCGG TTTACTCATT AAAGCTTGCC TGCGATTACC TAAGCACTGG 25260
CAAAGCCGAT ATCATGCTAG CAGGCGCAGT ATCTGGCGCG GATCCTTTCT TTATTAATAT 25320
GGGATTCTCA ATCTTCCACG CCTACCCAGA CCATGGTATC TCAGTACCGT TTGATGCCAG 25380
CAGTAAAGGT TTGTTTGCTG GCGAAGGCGC TGGCGTATTA GTGCTTAAAC GTCTTGAAGA 25440
TGCCGAGCGC GACAATGACA AAATCTATGC GGTTGTTAGC GGCGTAGGTC TATCAAACGA 25500
CGGTAAAGGC CAGTTTGTAT TAAGCCCTAA TCCAAAAGGT CAGGTGAAGG CCTTTGAACG 25560
TGCTTATGCT GCCAGTGACA TTGAGCCAAA AGACATTGAA GTGATTGAGT GCCACGCAAC 25620
AGGCACACCG CTTGGCGATA AAATTGAGCT CACTTCAATG GAAACCTTCT TTGAAGACAA 25680
GCTGCAAGGC ACCGATGCAC CGTTAATTGG CTCAGCTAAG TCTAACTTAG GCCACCTATT 25740
AACTGCAGCG CATGCGGGGA TCATGAAGAT GATCTTCGCC ATGAAAGAAG GTTACCTGCC 25800
GCCAAGTATC AATATTAGTG ATGCTATCGC TTCGCCGAAA AAACTCTTCG GTAAACCAAC 25860
CCTGCCTAGC ATGGTTCAAG GCTGGCCAGA TAAGCCATCG AATAATCATT TTGGTGTAAG 25920
AACCCGTCAC GCAGGCGTAT CGGTATTTGG CTTTGGTGGC TGTAACGCCC ATCTGTTGCT 25980
TGAGTCATAC AACGGCAAAG GAACAGTAAA GGCAGAAGCC ACTCAAGTAC CGCGTCAAGC 26040
TGAGCCGCTA AAAGTGGTTG GCCTTGCCTC GCACTTTGGG CCTCTTAGCA GCATTAATGC 26100
ACTCAACAAT GCTGTGACCC AAGATGGGAA TGGCTTTATC GAACTGCCGA AAAAGCGCTG 26160
GAAAGGCCTT GAAAAGCACA GTGAACTGTT AGCTGAATTT GGCTTAGCAT CTGCGCCAAA 26220
AGGTGCTTAT GTTGATAACT TCGAGCTGGA CTTTTTACGC TTTAAACTGC CGCCAAACGA 26280
AGATGACCGT TTGATCTCAC AGCAGCTAAT GCTAATGCGA GTAACAGACG AAGCCATTCG 26340
TGATGCCAAG CTTGAGCCGG GGCAAAAAGT AGCTGTATTA GTGGCAATGG AAACTGAGCT 26400
TGAACTGCAT CAGTTCCGCG GCCGGGTTAA CTTGCATACT CAATTAGCGC AAAGTCTTGC 26460
CGCCATGGGC GTGAGTTTAT CAACGGATGA ATACCAAGCG CTTGAAGCCA TCGCCATGGA 26520
CAGCGTGCTT GATGCTGCCA AGCTCAATCA GTACACCAGC TTTATTGGTA ATATTATGGC 26580
GTCACGCGTG GCGTCACTAT GGGACTTTAA TGGCCCAGCC TTCACTATTT CAGCAGCAGA 26640
GCAATCTGTG AGCCGCTGTA TCGATGTGGC GCAAAACCTC ATCATGGAGG ATAACCTAGA 26700
TGCGGTGGTG ATTGCAGCGG TCGATCTCTC TGGTAGCTTT GAGCAAGTCA TTCTTAAAAA 26760
TGCCATTGCA CCTGTAGCCA TTGAGCCAAA CCTCGAAGCA AGCCTTAATC CAACATCAGC 26820
AAGCTGGAAT GTCGGTGAAG GTGCTGGCGC GGTCGTGCTT GTTAAAAATG AAGCTACATC 26880
GGGCTGCTCA TACGGCCAAA TTGATGCACT TGGCTTTGCT AAAACTGCCG AAACAGCGTT 26940
GGCTACCGAC AAGCTACTGA GCCAAACTGC CACAGACTTT AATAAGGTTA AAGTGATTGA 27000
```

```
AACTATGGCA GCGCCTGCTA GCCAAATTCA ATTAGCGCCA ATAGTTAGCT CTCAAGTGAC 27060
TCACACTGCT GCAGAGCAGC GTGTTGGTCA CTGCTTTGCT GCAGCGGGTA TGGCAAGCCT 27120
ATTACACGGC TTACTTAACT TAAATACTGT AGCCCAAACC AATAAAGCCA ATTGCGCGCT 27180
TATCAACAAT ATCAGTGAAA ACCAATTATC ACAGCTGTTG ATTAGCCAAA CAGCGAGCGA 27240
ACAACAAGCA TTAACCGCGC GTTTAAGCAA TGAGCTTAAA TCCGATGCTA AACACCAACT 27300
GGTTAAGCAA GTCACCTTAG GTGGCCGTGA TATCTACCAG CATATTGTTG ATACACCGCT 27360
TGCAAGCCTT GAAAGCATTA CTCAGAAATT GGCGCAAGCG ACAGCATCGA CAGTGGTCAA 27420
CCAAGTTAAA CCTATTAAGG CCGCTGGCTC AGTCGAAATG GCTAACTCAT TCGAAACGGA 27480
AAGCTCAGCA GAGCCACAAA TAACAATTGC AGCACAACAG ACTGCAAACA TTGGCGTCAC 27540
CGCTCAGGCA ACCAAACGTG AATTAGGTAC CCCACCAATG ACAACAAATA CCATTGCTAA 27600
TACAGCAAAT AATTTAGACA AGACTCTTGA GACTGTTGCT GGCAATACTG TTGCTAGCAA 27660
GGTTGGCTCT GGCGACATAG TCAATTTTCA ACAGAACCAA CAATTGGCTC AACAAGCTCA 27720
CCTCGCCTTT CTTGAAAGCC GCAGTGCGGG TATGAAGGTG GCTGATGCTT TATTGAAGCA 27780
ACAGCTAGCT CAAGTAACAG GCCAAACTAT CGATAATCAG GCCCTCGATA CTCAAGCCGT 27840
CGATACTCAA ACAAGCGAGA ATGTAGCGAT TGCCGCAGAA TCACCAGTTC AAGTTACAAC 27900
ACCTGTTCAA GTTACAACAC CTGTTCAAAT CAGTGTTGTG GAGTTAAAAC CAGATCACGC 27960
TAATGTGCCA CCATACACGC CGCCAGTGCC TGCATTAAAG CCGTGTATCT GGAACTATGC 28020
CGATTTAGTT GAGTACGCAG AAGGCGATAT CGCCAAGGTA TTTGGCAGTG ATTATGCCAT 28080
TATCGACAGC TACTCGCGCC GCGTACGTCT ACCGACCACT GACTACCTGT TGGTATCGCG 28140
CGTGACCAAA CTTGATGCGA CCATCAATCA ATTTAAGCCA TGCTCAATGA CCACTGAGTA 28200
CGACATCCCT GTTGATGCGC CGTACTTAGT AGACGGACAA ATCCCTTGGG CGGTAGCAGT 28260
AGAATCAGGC CAATGTGACT TGATGCTTAT TAGCTATCTC GGTATCGACT TTGAGAACAA 28320
AGGCGAGCGG GTTTATCGAC TACTCGATTG TACCCTCACC TTCCTAGGCG ACTTGCCACG 28380
TGGCGGAGAT ACCCTACGTT ACGACATTAA GATCAATAAC TATGCTCGCA ACGGCGACAC 28440
CCTGCTGTTC TTCTTCTCGT ATGAGTGTTT TGTTGGCGAC AAGATGATCC TCAAGATGGA 28500
TGGCGGCTGC GCTGGCTTCT TCACTGATGA AGAGCTTGCC GACGGTAAAG GCGTGATTCG 28560
CACAGAAGAA GAGATTAAAG CTCGCAGCCT AGTGCAAAAG CAACGCTTTA ATCCGTTACT 28620
AGATTGTCCT AAAACCCAAT TTAGTTATGG TGATATTCAT AAGCTATTAA CTGCTGATAT 28680
TGAGGGTTGT TTTGGCCCAA GCCACAGTGG CGTCCACCAG CCGTCACTTT GTTTCGCATC 28740
TGAAAAATTC TTGATGATTG AACAAGTCAG CAAGGTTGAT CGCACTGGCG GTACTTGGGG 28800
ACTTGGCTTA ATTGAGGGTC ATAAGCAGCT TGAAGCAGAC CACTGGTACT TCCCATGTCA 28860
TTTCAAGGGC GACCAAGTGA TGGCTGGCTC GCTAATGGCT GAAGGTTGTG GCCAGTTATT 28920
GCAGTTCTAT ATGCTGCACC TTGGTATGCA TACCCAAACT AAAAATGGTC GTTTCCAACC 28980
TCTTGAAAAC GCCTCACAGC AAGTACGCTG TCGCGGTCAA GTGCTGCCAC AATCAGGCGT 29040
GCTAACTTAC CGTATGGAAG TGACTGAAAT CGGTTTCAGT CCACGCCCAT ATGCTAAAGC 29100
TAACATCGAT ATCTTGCTTA ATGGCAAAGC GGTAGTGGAT TTCCAAAACC TAGGGGTGAT 29160
GATAAAAGAG GAAGATGAGT GTACTCGTTA TCCACTTTTG ACTGAATCAA CAACGGCTAG 29220
CACTGCACAA GTAAACGCTC AAACAAGTGC GAAAAAGGTA TACAAGCCAG CATCAGTCAA 29280
TGCGCCATTA ATGGCACAAA TTCCTGATCT GACTAAAGAG CCAAACAAGG GCGTTATTCC 29340
GATTTCCCAT GTTGAAGCAC CAATTACGCC AGACTACCCG AACCGTGTAC CTGATACAGT 29400
```

GCCATTCACG CCGTATCACA TGTTTGAGTT TGCTACAGGC AATATCGAAA ACTGTTTCGG 29460

GCCAGAGTTC TCAATCTATC GCGGCATGAT CCCACCACGT ACACCATGCG GTGACTTACA 29520

AGTGACCACA CGTGTGATTG AAGTTAACGG TAAGCGTGGC GACTTTAAAA AGCCATCATC 29580

GTGTATCGCT GAATATGAAG TGCCTGCAGA TGCGTGGTAT TTCGATAAAA ACAGCCACGG 29640

CGCAGTGATG CCATATTCAA TTTTAATGGA GATCTCACTG CAACCTAACG GCTTTATCTC 29700

AGGTTACATG GGCACAACCC TAGGCTTCCC TGGCCTTGAG CTGTTCTTCC GTAACTTAGA 29760

CGGTAGCGGT GAGTTACTAC GTGAAGTAGA TTTACGTGGT AAAACCATCC GTAACGACTC 29820

ACGTTTATTA TCAACAGTGA TGGCCGGCAC TAACATCATC CAAAGCTTTA GCTTCGAGCT 29880

AAGCACTGAC GGTGAGCCTT TCTATCGCGG CACTGCGGTA TTTGGCTATT TTAAAGGTGA 29940

CGCACTTAAA GATCAGCTAG GCCTAGATAA CGGTAAAGTC ACTCAGCCAT GGCATGTAGC 30000

TAACGGCGTT GCTGCAAGCA CTAAGGTGAA CCTGCTTGAT AAGAGCTGCC GTCACTTTAA 30060

TGCGCCAGCT AACCAGCCAC ACTATCGTCT AGCCGGTGGT CAGCTGAACT TTATCGACAG 30120

TGTTGAAATT GTTGATAATG GCGGCACCGA AGGTTTAGGT TACTTGTATG CCGAGCGCAC 30180

CATTGACCCA AGTGATTGGT TCTTCCAGTT CCACTTCCAC CAAGATCCGG TTATGCCAGG 30240

CTCCTTAGGT GTTGAAGCAA TTATTGAAAC CATGCAAGCT TACGCTATTA GTAAAGACTT 30300

GGGCGCAGAT TTCAAAAATC CTAAGTTTGG TCAGATTTTA TCGAACATCA AGTGGAAGTA 30360

TCGCGGTCAA ATCAATCCGC TGAACAAGCA GATGTCTATG GATGTCAGCA TTACTTCAAT 30420

CAAAGATGAA GACGGTAAGA AAGTCATCAC AGGTAATGCC AGCTTGAGTA AAGATGGTCT 30480

GCGCATATAC GAGGTCTTCG ATATAGCTAT CAGCATCGAA GAATCTGTAT AAATCGGAGT 30540

GACTGTCTGG CTATTTTACT CAATTTCTGT GTCAAAAGTG CTCACCTATA TTCATAGGCT 30600

GCGCGCTTTT TTCTGGAAAT TGAGCAAAAG TATCTGCGTC CTAACTCGAT TTATAAGAAT 30660

GGTTTAATTG AAAAGAACAA CAGCTAAGAG CCGCAAGCTC AATATAAATA ATTAAGGGTC 30720

TTACAAATAA TGAATCCTAC AGCAACTAAC GAAATGCTTT CTCCGTGGCC ATGGGCTGTG 30780

ACAGAGTCAA ATATCAGTTT TGACGTGCAA GTGATGGAAC AACAACTTAA AGATTTTAGC 30840

CGGGCATGTT ACGTGGTCAA TCATGCCGAC CACGGCTTTG GTATTGCGCA AACTGCCGAT 30900

ATCGTGACTG AACAAGCGGC AAACAGCACA GATTTACCTG TTAGTGCTTT TACTCCTGCA 30960

TTAGGTACCG AAAGCCTAGG CGACAATAAT TTCCGCCGCG TTCACGGCGT TAAATACGCT 31020

TATTACGCAG GCGCTATGGC AAACGGTATT TCATCTGAAG AGCTAGTGAT TGCCCTAGGT 31080

CAAGCTGGCA TTTTGTGTGG TTCGTTTGGA GCAGCCGGTC TTATTCCAAG TCGCGTTGAA 31140

GCGGCAATTA ACCGTATTCA AGCAGCGCTG CCAAATGGCC CTTATATGTT TAACCTTATC 31200

CATAGTCCTA GCGAGCCAGC ATTAGAGCGT GGCAGCGTAG AGCTATTTTT AAAGCATAAG 31260

GTACGCACCG TTGAAGCATC AGCTTTCTTA GGTCTAACAC CACAAATCGT CTATTACCGT 31320

GCAGCAGGAT TGAGCCGAGA CGCACAAGGT AAAGTTGTGG TTGGTAACAA GGTTATCGCT 31380

AAAGTAAGTC GCACCGAAGT GGCTGAAAAG TTTATGATGC CAGCGCCCGC AAAAATGCTA 31440

CAAAAACTAG TTGATGACGG TTCAATTACC GCTGAGCAAA TGGAGCTGGC GCAACTTGTA 31500

CCTATGGCTG ACGACATCAC TGCAGAGGCC GATTCAGGTG GCCATACTGA TAACCGTCCA 31560

TTAGTAACAT TGCTGCCAAC CATTTTAGCG CTGAAAGAAG AAATTCAAGC TAAATACCAA 31620

TACGACACTC CTATTCGTGT CGGTTGTGGT GGCGGTGTGG GTACGCCTGA TGCAGCGCTG 31680

GCAACGTTTA ACATGGGCGC GGCGTATATT GTTACCGGCT CTATCAACCA AGCTTGTGTT 31740

GAAGCGGGCG CAAGTGATCA CACTCGTAAA TTACTTGCCA CCACTGAAAT GGCCGATGTG 31800

ACTATGGCAC CAGCTGCAGA TATGTTCGAG ATGGGCGTAA AACTGCAGGT GGTTAAGCGC 31860
GGCACGCTAT TCCCAATGCG CGCTAACAAG CTATATGAGA TCTACACCCG TTACGATTCA 31920
ATCGAAGCGA TCCCATTAGA CGAGCGTGAA AAGCTTGAGA AACAAGTATT CCGCTCAAGC 31980
CTAGATGAAA TATGGGCAGG TACAGTGGCG CACTTTAACG AGCGCGACCC TAAGCAAATC 32040
GAACGCGCAG AGGGTAACCC TAAGCGTAAA ATGGCATTGA TTTTCCGTTG GTACTTAGGT 32100
CTTTCTAGTC GCTGGTCAAA CTCAGGCGAA GTGGGTCGTG AAATGGATTA TCAAATTTGG 32160
GCTGGCCCTG CTCTCGGTGC ATTTAACCAA TGGGCAAAAG GCAGTTACTT AGATAACTAT 32220
CAAGACCGAA ATGCCGTCGA TTTGGCAAAG CACTTAATGT ACGGCGCGGC TTACTTAAAT 32280
CGTATTAACT CGCTAACGGC TCAAGGCGTT AAAGTGCCAG CACAGTTACT TCGCTGGAAG 32340
CCAAACCAAA GAATGGCCTA ATACACTTAC AAAGCACCAG TCTAAAAAGC CACTAATCTT 32400
GATTAGTGGC TTTTTTTATT GTGGTCAATA TGAGGCTATT TAGCCTGTAA GCCTGAAAAT 32460
ATCAGCACTC TGACTTTACA AGCAAATTAT AATTAAGGCA GGGCTCTACT CATTTATACT 32520
GCTAGCAAAC AAGCAAGTTG CCCAGTAAAA CAACAAGGTA CCTGATTTAT ATCGTCATAA 32580
AAGTTGGCTA GAGATTCGTT ATTGATCTTT ACTGATTAGA GTCGCTCTGT TTGGAAAAAG 32640
GTTTCTCGTT ATCATCAAAA TACACTCTCA AACCTTTAAT CAATTACAAC TTAGGCTTTC 32700
TGCGGGCATT TTTATCTTAT TTGCCACAGC TGTATTTGCC TTTAGGTTTT GGGTGCAACT 32760
ACCATTAATT GAGGCCTCAT TAGTTAAATT ATCTGAGCAA GAGCTCACCT CTTTAAATTA 32820
CGCTTTTCAG CAAATGAGAA AGCCACTACA AACCATTAAT TACGACTATG CGGTGTGGGA 32880
CAGAACCTAC AGCTATATGA AATCAAACTC AGCGAGCGCT AAAAGGTACT ATGAAAAACA 32940
TGAGTACCCA GATGATACGT TCAAGAGTTT AAAAGTCGAC GGAGTATTTA TATTCAACCG 33000
TACAAATCAG CCAGTTTTTA GTAAAGGTTT TAATCATAGA AATGATATAC CGCTGGTCTT 33060
TGAATTAACT GACTTTAAAC AACATCCACA AAACATCGCA TTATCTCCAC AAACCAAACA 33120
GGCACACCCA CCGGCAAGTA AGCCGTTAGA CTCCCCTGAT GATGTGCCTT CTACCCATGG 33180
GGTTATCGCC ACACGATACG GTCCAGCAAT TTATAGCTCT ACCAGCATTT TAAAATCTGA 33240
TCGTAGCGGC TCCCAACTTG GTTATTTAGT CTTCATTAGG TTAATTGATG AATGGTTCAT 33300
CGCTGAGCTA TCGCAATACA CTGCCGCAGG TGTTGAAATC GCTATGGCTG ATGCCGCAGA 33360
CGCACAATTA GCGAGATTAG GCGCAAACAC TAAGCTTAAT AAAGTAACCG CTACATCCGA 33420
ACGGTTAATA ACTAATGTCG ATGGTAAGCC TCTGTTGAAG TTAGTGCTTT ACCATACCAA 33480
TAACCAACCG CCGCCGATGC TAGATTACAG TATAATAATT CTATTAGTTG AGATGTCATT 33540
TTTACTGATC CTCGCTTATT TCCTTTACTC CTACTTCTTA GTCAGGCCAG TTAGAAAGCT 33600
GGCTTCAGAT ATTAAAAAAA TGGATAAAAG TCGTGAAATT AAAAAGCTAA GGTATCACTA 33660
CCCTATTACT GAGCTAGTCA AAGTTGCGAC TCACTTCAAC GCCCTAATGG GGACGATTCA 33720
GGAACAAACT AAACAGCTTA ATGAACAAGT TTTTATTGAT AAATTAACCA ATATTCCCAA 33780
TCGTCGCGCT TTTGAGCAGC GACTTGAAAC CTATTGCCAA CTGCTAGCCC GGCAACAAAT 33840
TGGCTTTACT CTCATCATTG CCGATGTGGA TCATTTTAAA GAGTACAACG ATACTCTTGG 33900
GCACCTTGCT GGGGATGAAG CATTAATAAA AGTGGCACAA ACACTATCGC AACAGTTTTA 33960
CCGTGCAGAA GATATTTGTG CCCGTTTTGG TGGTGAAGAA TTTATTATGT TATTTCGAGA 34020
CATACCTGAT GAGCCCTTGC AGAGAAAGCT CGATGCGATG CTGCACTCTT TTGCAGAGCT 34080
CAACCTACCT CATCCAAACT CATCAACCGC TAATTACGTT ACTGTGAGCC TTGGGGTTTG 34140
CACAGTTGTT GCTGTTGATG ATTTTGAATT TAAAAGTGAG TCGCATATTA TTGGCAGTCA 34200

```
GGCTGCATTA ATCGCAGATA AGGCGCTTTA TCATGCTAAA GCCTGTGGTC GTAACCAGTT 34260
GTCAAAAACT ACTATTACTG TTGATGAGAT TGAGCAATTA GAAGCAAATA AAATCGGTCA 34320
TCAAGCCTAA ACTCGTTCGA GTACTTTCCC CTAAGTCAGA GCTATTTGCC ACTTCAAGAT 34380
GTGGCTACAA GGCTTACTCT TTCAAAACCT GCATCAATAG AACACAGCAA AATACAATAA 34440
TTTAAGTCAA TTTAGCCTAT TAAACAGAGT TAATGACAGC TCATGGTCGC AACTTATTAG 34500
CTATTTCTAG CAATATAAAA ACTTATCCAT TAGTAGTAAC CAATAAAAAA ACTAATATAT 34560
AAAACTATTT AATCATTATT TTACAGATGA TTAGCTACCA CCCACCTTAA GCTGGCTATA 34620
TTCGCACTAG TAAAAATAAA CATTAGATCG GGTTCAGATC AATTTACGAG TCTCGTATAA 34680
AATGTACAAT AATTCACTTA ATTTAATACT GCATATTTTT ACAAGTAGAG AGCGGTGATG 34740
AAACAAAATA CGAAAGGCTT TACATTAATT GAATTAGTCA TCGTGATTAT TATTCTCGGT 34800
ATACTTGCTG CTGTGGCACT GCCGAAATTC ATCAATGTTC AAGATGACGC TAGGATCTCT 34860
GCGATGAGCG GTCAGTTTTC ATCATTTGAA AGTGCCGTAA AACTATACCA TAGCGGTTGG 34920
TTAGCCAAAG GCTACAACAC TGCGGTTGAA AAGCTCTCAG GCTTTGGCCA AGGTAATGTT 34980
GCATCAAGTG ACACAGGTTT TCCGTACTCA ACATCAGGCA CGAGTACTGA TGTGCATAAA 35040
GCTTGTGGTG AACTATGGCA TGGCATTACC GATACAGACT TCACAATTGG TGCGGTTAGT 35100
GATGGCGATC TAATGACTGC AGATGTCGAT ATTGCTTACA CCTATCGTGG TGATATGTGT 35160
ATCTATCGCG ATCTGTATTT TATTCAGCGC TCATTACCTA CTAAGGTGAT GAACTACAAA 35220
TTTAAAACTG GTGAAATAGA AATTATTGAT GCTTTCTACA ACCCTGACGG CTCAACTGGT 35280
CAATTACCAT AAATTTGGCG CTTATCTAAG TTGTACTTGC TCTGACCGAC ACAAATAATG 35340
TCGTTTCTCA GCATATATCA AAATACACAG CAAAAATTTG GGGTTAGCTA TATAGCTAAC 35400
CCCAAATCAT ATCTAACTTT ACACTGCATC TAATTCCAAA CAGTATCCAG CCAAAAGCCT 35460
AAACTATTGT TGACTCAGCG CTAAAATATG CGATGCAACA AACAAGTCTT GGATCGCAAT 35520
ACCTGAGCTA TCAAAAATGG TCACCTCATC AGCACTTTGA CGTCCTGTTG CGGACTCGTT 35580
TATCACCTGA CCAATCTCAA TTATCGGCGT ATTTCTGCTA TGTTGAAACT CACCAATAAC 35640
AATAGATTGA GAAGCAAAGT CGCAAAACAA GCGAGCATGA CTATATAGGT CAGTTGGCAA 35700
CTCTTGCTTA CCCACTTTAT CAGCGCCCAT TGCAGAAATA TGCGTTCCTG CTTGTACCCA 35760
CTGCGCTTCA AATAAAGGCG CTTGAGCTGT GGTTGCTGTG ATAATAATAT CTGCTTGTTC 35820
ACAAGCAGCT TGTGCATCAC AAGCTTCGGC ATTAATGCCT TTTTCTAATA AACGCTTAAC 35880
CAAGTTTTCA GTTTTGCTAG CACTACGGCC AACTACCAAT ACCTTAGTTA ATGAACGAAC 35940
CTTGCTCACT GCTAGCACTT CATATTCAGC CTGATGACCG GTACCAAAAA CAGTTAATAC 36000
CGTAGCATCT TCTCTCGCGA GGTAACTCAC TGCTACTGCA TCGGCAGCAC CAGTGCGGTA 36060
AGCATTAACG GTAGTGGCAG CAATCACCGN CTGCAACATA CCGGTTAATG GATCGAGTAA 36120
AAATACGTTA GTGCCGTGGC ATGGTAAACC ATGTTTATGG TTATCAGGCC AATAGCTGCC 36180
TGTTTTCCAG CCGACAAGGT TTGGCGTTGA AGCCGACTTT AATGAGAACA TTTCATTAAG 36240
GTTCGCGCCC TGTGCATTAA CTACCGGGAA CAAGGTTGCT TTATCATCTA CGGCAGCGAC 36300
AAACGCTTCT TTAACAGCGA TATAAGCCAG CTCATGGGAG ATGAGCTTTG ATGTTTGCGC 36360
TTCAGTTAAA TAGATCATAT TACCACCCCT GCACTCGATT CCAGATCTCA TAGCCACCAT 36420
TATCACCATC AGTATCAAAT ACATGGTACT GAGCGTGCAT TGAAGCTGTT GCACAGGCGT 36480
GGTTCGGCAA AATATGTAGA CGACTACCTA CCGGGAACTG CGCTAAATCA ATAACGCCGC 36540
CATCAACTGC TTCAATAATG CCGTGCTCTT GATTAACAGT TATAACCTGT AGACCTGATA 36600
```

-continued

```
ACACGTGACC GCTGTCGTCA CACACTAAAC CATAACCACA ATCTTTTGGC TGCTCTGCAG 36660
TACCTCTATC ACCCGAAAGA GCCATCCAAC CCGCATCAAT GAAAATCCAG TTTTTATCAG 36720
GATTATGACC AATAACACTG GTCACTACCG TTGCGGCAAT ATCAGTTAAC TGACACACGT 36780
TTAGCCCTGC CATGACTAAA TCGAAGAAGG TGTACACACC CGCTCTAACC TCGGTGATCC 36840
CATCAAGGTT TTGATAGCTT TGCGCTGTTG GTGTTGAACC AATACTAACG ATGTCACATT 36900
GCATACCCGC TGCGCGAATG CGTCAGCAGC TTGTACAGCC GCTGCAACTT CATTTTGCGC 36960
CGCATCAATT AATTGCTGTT TTTCAAAACA TTGATATGAC TCACCAGCGT GAGTGAGTAC 37020
GCCGTGAAAA CTCGCTGCGC CAGACGTTAG TATCTGAGCA ATTTCAATCA ACTTATCGGC 37080
TTCCGGTGGA ATACCACCAC GATGGCCATC ACAATCAATT TCAATTAATG CTGGTATTTG 37140
GCAGTCATAA GAACCACAGA AATGATTTAG CTGATGCGCT TGCTCAACAC TATCAAGTAA 37200
AACTCTTGCA TTAATACCTT GGTCCAACAT TTTAGCAATA CGCGGCAACT TACCATCGGC 37260
AATACCTACT GCATAAATAA TGTCTGTGTA ACCTTTAGAT GCTAAGGCCT CGGCCTCTTT 37320
TACCGTTGAT ACAGTGACTG GTGAGTTTTT AGTGGGTAAT AAAAACTCGG CTGCTTCAAG 37380
TGATCTTAAC GTTTTAAAAT GCGGTCTTAG GTTTGCACCT AATCCTTCAA TTTTTTGGCG 37440
TAGTTGACTG AGGTTATTAA TAAATACTGG CTTATTTACA TATAAAAACG GTGTATCAAT 37500
TGCTTGATAC TGACTTTGCT GAGTCGTGGA AAGTATTTGA GTAGATGGCA TCTTTAATAT 37560
CCTAGTTCAT CAATCAATCT AACAAGTTTG ATGCCTAGCC ACAGTGGCTT GTATTCATGA 37620
TGCTTTGGAA AATGCTTATA TTCAAAGTAT TTGAAAGACA TCAAACTTCT TGTTTAATGC 37680
TCAGTATCCA CCAGCACGCA TTTATTTTAT ATTAACTATT ATCAAGATAT AGATTAGGTT 37740
CAAACCAAAT GATTAGTACT GAAGATCTAC GTTTTATCAG CGTAATCGCC AGTCATCGCA 37800
CCTTAGCTGA TGCCGCTAGA ACACTAAATA TCACGCCACC ATCAGTGACA TTAAGGTTGC 37860
AGCATATTGA AAAGAAACTA TCGATTAGCC TGATC                            37895
```

( 2 ) INFORMATION FOR SEQ ID NO:2:

( i ) SEQUENCE CHARACTERISTICS:
( A ) LENGTH: 1983 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( A ) ORGANISM: Shewanella putrefaciens SCRC-2874 (FERM BP- 1625)

( i x ) FEATURE:
( A ) NAME/KEY: CDS
( B ) LOCATION: 1..1983

( i x ) FEATURE:
( A ) NAME/KEY: mat_peptide
( B ) LOCATION: 1..1983

( x i ) SEQUENCE DESCRIPTION: SEQ ID NO:2:

```
ATG AAA CAG ACT CTA ATG GCT ATC TCA ATC ATG TCG CTT TTT TCA TTC      48
Met Lys Gln Thr Leu Met Ala Ile Ser Ile Met Ser Leu Phe Ser Phe
  1               5                  10                  15

AAT GCG CTA GCA GCG CAA CAT GAA CAT GAC CAC ATC ACT GTT GAT TAC      96
Asn Ala Leu Ala Ala Gln His Glu His Asp His Ile Thr Val Asp Tyr
             20                  25                  30

GAA GGG AAA GCC GCA ACA GAA CAC ACC ATA GCT CAC AAC CAA GCT GTA     144
Glu Gly Lys Ala Ala Thr Glu His Thr Ile Ala His Asn Gln Ala Val
```

-continued

```
        35                  40                  45

GCT AAA ACA CTT AAC TTT GCC GAC ACG CGT GCA TTT GAG CAA TCG TCT     192
Ala Lys Thr Leu Asn Phe Ala Asp Thr Arg Ala Phe Glu Gln Ser Ser
    50                  55                  60

AAA AAT CTA GTC GCC AAG TTT GAT AAA GCA ACT GCC GAT ATA TTA CGT     240
Lys Asn Leu Val Ala Lys Phe Asp Lys Ala Thr Ala Asp Ile Leu Arg
65                  70                  75                  80

GCC GAA TTT GCT TTT ATT AGC GAT GAA ATC CCT GAC TCG GTT AAC CCG     288
Ala Glu Phe Ala Phe Ile Ser Asp Glu Ile Pro Asp Ser Val Asn Pro
                85                  90                  95

TCT CTC TAC CGT CAG GCT CAG CTT AAT ATG GTG CCT AAT GGT CTG TAT     336
Ser Leu Tyr Arg Gln Ala Gln Leu Asn Met Val Pro Asn Gly Leu Tyr
            100                 105                 110

AAA GTG AGC GAT GGC ATT TAC CAG GTC CGC GGT ACC GAC TTA TCT AAC     384
Lys Val Ser Asp Gly Ile Tyr Gln Val Arg Gly Thr Asp Leu Ser Asn
        115                 120                 125

CTT ACA CTT ATC CGC AGT GAT AAC GGT TGG ATA GCA TAC GAT GTT TTG     432
Leu Thr Leu Ile Arg Ser Asp Asn Gly Trp Ile Ala Tyr Asp Val Leu
    130                 135                 140

TTA ACC AAA GAA GCA GCA AAA GCC TCA CTA CAA TTT GCG TTA AAG AAT     480
Leu Thr Lys Glu Ala Ala Lys Ala Ser Leu Gln Phe Ala Leu Lys Asn
145                 150                 155                 160

CTA CCT AAA GAT GGC GAT TTA CCC GTT GTT GCG ATG ATT TAC TCC CAT     528
Leu Pro Lys Asp Gly Asp Leu Pro Val Val Ala Met Ile Tyr Ser His
                165                 170                 175

AGC CAT GCG GAC CAC TTT GGC GGA GCT CGC GGT GTT CAA GAG ATG TTC     576
Ser His Ala Asp His Phe Gly Gly Ala Arg Gly Val Gln Glu Met Phe
            180                 185                 190

CCT GAT GTC AAA GTC TAC GGC TCA GAT AAC ATC ACT AAA GAA ATT GTC     624
Pro Asp Val Lys Val Tyr Gly Ser Asp Asn Ile Thr Lys Glu Ile Val
        195                 200                 205

GAT GAG AAC GTA CTT GCC GGT AAC GCC ATG AGC CGC CGC GCA GCT TAT     672
Asp Glu Asn Val Leu Ala Gly Asn Ala Met Ser Arg Arg Ala Ala Tyr
    210                 215                 220

CAA TAC GGC GCA ACA CTG GGC AAA CAT GAC CAC GGT ATT GTT GAT GCT     720
Gln Tyr Gly Ala Thr Leu Gly Lys His Asp His Gly Ile Val Asp Ala
225                 230                 235                 240

GCG CTA GGT AAA GGT CTA TCA AAA GGT GAA ATC ACT TAC GTC GCC CCA     768
Ala Leu Gly Lys Gly Leu Ser Lys Gly Glu Ile Thr Tyr Val Ala Pro
                245                 250                 255

GAC TAC ACC TTA AAC AGT GAA GGC AAA TGG GAA ACG CTG ACG ATT GAT     816
Asp Tyr Thr Leu Asn Ser Glu Gly Lys Trp Glu Thr Leu Thr Ile Asp
            260                 265                 270

GGT CTA GAG ATG GTG TTT ATG GAT GCC TCG GGC ACC GAA GCT GAG TCA     864
Gly Leu Glu Met Val Phe Met Asp Ala Ser Gly Thr Glu Ala Glu Ser
        275                 280                 285

GAA ATG ATC ACT TAT ATT CCC TCT AAA AAA GCG CTC TGG ACG GCG GAG     912
Glu Met Ile Thr Tyr Ile Pro Ser Lys Lys Ala Leu Trp Thr Ala Glu
    290                 295                 300

CTT ACC TAT CAA GGT ATG CAC AAC ATT TAT ACG CTG CGC GGC GCT AAA     960
Leu Thr Tyr Gln Gly Met His Asn Ile Tyr Thr Leu Arg Gly Ala Lys
305                 310                 315                 320

GTA CGT GAT GCG CTC AAG TGG TCA AAA GAT ATC AAC GAA ATG ATC AAT    1008
Val Arg Asp Ala Leu Lys Trp Ser Lys Asp Ile Asn Glu Met Ile Asn
                325                 330                 335

GCC TTT GGT CAA GAT GTC GAA GTG CTG TTT GCC TCG CAC TCT GCG CCA    1056
Ala Phe Gly Gln Asp Val Glu Val Leu Phe Ala Ser His Ser Ala Pro
            340                 345                 350

GTG TGG GGT AAC CAA GCG ATC AAC GAT TTC TTA CGC CTA CAG CGT GAT    1104
Val Trp Gly Asn Gln Ala Ile Asn Asp Phe Leu Arg Leu Gln Arg Asp
```

-continued

```
        355                                  360                                  365

AAC TAC GGC CTA GTG CAC AAT CAA ACC TTG AGA CTT GCC AAC GAT GGT      1152
Asn Tyr Gly Leu Val His Asn Gln Thr Leu Arg Leu Ala Asn Asp Gly
    370                     375                     380

GTC GGT ATA CAA GAT ATT GGC GAT GCG ATT CAA GAC ACG ATT CCA GAG      1200
Val Gly Ile Gln Asp Ile Gly Asp Ala Ile Gln Asp Thr Ile Pro Glu
385                     390                     395                     400

TCT ATC TAC AAG ACG TGG CAT ACC AAT GGT TAC CAC GGC ACT TAT AGC      1248
Ser Ile Tyr Lys Thr Trp His Thr Asn Gly Tyr His Gly Thr Tyr Ser
                405                     410                     415

CAT AAC GCT AAA GCG GTT TAT AAC AAG TAT CTA GGC TAC TTC GAT ATG      1296
His Asn Ala Lys Ala Val Tyr Asn Lys Tyr Leu Gly Tyr Phe Asp Met
            420                     425                     430

AAC CCA GCC AAC CTT AAT CCG CTG CCA ACC AAG CAA GAA TCT GCC AAG      1344
Asn Pro Ala Asn Leu Asn Pro Leu Pro Thr Lys Gln Glu Ser Ala Lys
        435                     440                     445

TTT GTC GAA TAC ATG GGC GGC GCA GAT GCC GCA ATT AAG CGC GCT AAA      1392
Phe Val Glu Tyr Met Gly Gly Ala Asp Ala Ala Ile Lys Arg Ala Lys
    450                     455                     460

GAT GAT TAC GCT CAA GGT GAA TAC CGC TTT GTT GCA ACG GCA TTA AAT      1440
Asp Asp Tyr Ala Gln Gly Glu Tyr Arg Phe Val Ala Thr Ala Leu Asn
465                     470                     475                     480

AAG GTG GTG ATG GCC GAG CCA GAA AAT GAC TCC GCT CGT CAA TTG CTA      1488
Lys Val Val Met Ala Glu Pro Glu Asn Asp Ser Ala Arg Gln Leu Leu
                485                     490                     495

GCC GAT ACC TAT GAG CAA CTT GGT TAT CAA GCA GAA GGG GCT GGC TGG      1536
Ala Asp Thr Tyr Glu Gln Leu Gly Tyr Gln Ala Glu Gly Ala Gly Trp
            500                     505                     510

AGA AAC ATT TAC TTA ACT GGC GCA CAA GAG CTA CGA GTA GGT ATT CAA      1584
Arg Asn Ile Tyr Leu Thr Gly Ala Gln Glu Leu Arg Val Gly Ile Gln
        515                     520                     525

GCT GGC GCG CCT AAA ACC GCA TCG GCA GAT GTC ATC AGT GAA ATG GAC      1632
Ala Gly Ala Pro Lys Thr Ala Ser Ala Asp Val Ile Ser Glu Met Asp
    530                     535                     540

ATG CCG ACT CTA TTT GAC TTC CTC GCG GTG AAG ATT GAT AGT CAA CAG      1680
Met Pro Thr Leu Phe Asp Phe Leu Ala Val Lys Ile Asp Ser Gln Gln
545                     550                     555                     560

GCG GCT AAG CAC GGC TTA GTT AAG ATG AAT GTT ATC ACC CCT GAT ACT      1728
Ala Ala Lys His Gly Leu Val Lys Met Asn Val Ile Thr Pro Asp Thr
                565                     570                     575

AAA GAT ATT CTC TAT ATT GAG CTA AGC AAC GGT AAC TTA AGC AAC GCA      1776
Lys Asp Ile Leu Tyr Ile Glu Leu Ser Asn Gly Asn Leu Ser Asn Ala
            580                     585                     590

GTG GTC GAC AAA GAG CAA GCA GCT GAC GCA AAC CTT ATG GTT AAT AAA      1824
Val Val Asp Lys Glu Gln Ala Ala Asp Ala Asn Leu Met Val Asn Lys
        595                     600                     605

GCT GAC GTT AAC CGC ATC TTA CTT GGC CAA GTA ACC CTA AAA GCG TTA      1872
Ala Asp Val Asn Arg Ile Leu Leu Gly Gln Val Thr Leu Lys Ala Leu
    610                     615                     620

TTA GCC AGC GGC GAT GCC AAG CTC ACT GGT GAT AAA ACG GCA TTT AGT      1920
Leu Ala Ser Gly Asp Ala Lys Leu Thr Gly Asp Lys Thr Ala Phe Ser
625                     630                     635                     640

AAA ATA GCC GAT AGC ATG GTC GAG TTT ACA CCT GAC TTC GAA ATC GTA      1968
Lys Ile Ala Asp Ser Met Val Glu Phe Thr Pro Asp Phe Glu Ile Val
                645                     650                     655

CCA ACG CCT GTT AAA                                                  1983
Pro Thr Pro Val Lys
            660
```

( 2 ) INFORMATION FOR SEQ ID NO:3:

(i) SEQUENCE CHARACTERISTICS:
(A) LENGTH: 661 amino acids
(B) TYPE: amino acid
(D) TOPOLOGY: linear (ii) MOLECULE TYPE: protein (xi) SEQUENCE DESCRIPTION: SEQ ID NO:3:

Met Lys Gln Thr Leu Met Ala Ile Ser Ile Met Ser Leu Phe Ser Phe
1 5 10 15

Asn Ala Leu Ala Ala Gln His Glu His Asp His Ile Thr Val Asp Tyr
20 25 30

Glu Gly Lys Ala Ala Thr Glu His Thr Ile Ala His Asn Gln Ala Val
35 40 45

Ala Lys Thr Leu Asn Phe Ala Asp Thr Arg Ala Phe Glu Gln Ser Ser
50 55 60

Lys Asn Leu Val Ala Lys Phe Asp Lys Ala Thr Ala Asp Ile Leu Arg
65 70 75 80

Ala Glu Phe Ala Phe Ile Ser Asp Glu Ile Pro Asp Ser Val Asn Pro
85 90 95

Ser Leu Tyr Arg Gln Ala Gln Leu Asn Met Val Pro Asn Gly Leu Tyr
100 105 110

Lys Val Ser Asp Gly Ile Tyr Gln Val Arg Gly Thr Asp Leu Ser Asn
115 120 125

Leu Thr Leu Ile Arg Ser Asp Asn Gly Trp Ile Ala Tyr Asp Val Leu
130 135 140

Leu Thr Lys Glu Ala Ala Lys Ala Ser Leu Gln Phe Ala Leu Lys Asn
145 150 155 160

Leu Pro Lys Asp Gly Asp Leu Pro Val Val Ala Met Ile Tyr Ser His
165 170 175

Ser His Ala Asp His Phe Gly Gly Ala Arg Gly Val Gln Glu Met Phe
180 185 190

Pro Asp Val Lys Val Tyr Gly Ser Asp Asn Ile Thr Lys Glu Ile Val
195 200 205

Asp Glu Asn Val Leu Ala Gly Asn Ala Met Ser Arg Arg Ala Ala Tyr
210 215 220

Gln Tyr Gly Ala Thr Leu Gly Lys His Asp His Gly Ile Val Asp Ala
225 230 235 240

Ala Leu Gly Lys Gly Leu Ser Lys Gly Glu Ile Thr Tyr Val Ala Pro
245 250 255

Asp Tyr Thr Leu Asn Ser Glu Gly Lys Trp Glu Thr Leu Thr Ile Asp
260 265 270

Gly Leu Glu Met Val Phe Met Asp Ala Ser Gly Thr Glu Ala Glu Ser
275 280 285

Glu Met Ile Thr Tyr Ile Pro Ser Lys Lys Ala Leu Trp Thr Ala Glu
290 295 300

Leu Thr Tyr Gln Gly Met His Asn Ile Tyr Thr Leu Arg Gly Ala Lys
305 310 315 320

Val Arg Asp Ala Leu Lys Trp Ser Lys Asp Ile Asn Glu Met Ile Asn
325 330 335

Ala Phe Gly Gln Asp Val Glu Val Leu Phe Ala Ser His Ser Ala Pro
340 345 350

Val Trp Gly Asn Gln Ala Ile Asn Asp Phe Leu Arg Leu Gln Arg Asp
355 360 365

Asn Tyr Gly Leu Val His Asn Gln Thr Leu Arg Leu Ala Asn Asp Gly

-continued

```
    370                 375                 380

Val Gly Ile Gln Asp Ile Gly Asp Ala Ile Gln Asp Thr Ile Pro Glu
385                 390                 395                 400

Ser Ile Tyr Lys Thr Trp His Thr Asn Gly Tyr His Gly Thr Tyr Ser
                405                 410                 415

His Asn Ala Lys Ala Val Tyr Asn Lys Tyr Leu Gly Tyr Phe Asp Met
            420                 425                 430

Asn Pro Ala Asn Leu Asn Pro Leu Pro Thr Lys Gln Glu Ser Ala Lys
        435                 440                 445

Phe Val Glu Tyr Met Gly Gly Ala Asp Ala Ala Ile Lys Arg Ala Lys
    450                 455                 460

Asp Asp Tyr Ala Gln Gly Glu Tyr Arg Phe Val Ala Thr Ala Leu Asn
465                 470                 475                 480

Lys Val Val Met Ala Glu Pro Glu Asn Asp Ser Ala Arg Gln Leu Leu
                485                 490                 495

Ala Asp Thr Tyr Glu Gln Leu Gly Tyr Gln Ala Glu Gly Ala Gly Trp
            500                 505                 510

Arg Asn Ile Tyr Leu Thr Gly Ala Gln Glu Leu Arg Val Gly Ile Gln
        515                 520                 525

Ala Gly Ala Pro Lys Thr Ala Ser Ala Asp Val Ile Ser Glu Met Asp
    530                 535                 540

Met Pro Thr Leu Phe Asp Phe Leu Ala Val Lys Ile Asp Ser Gln Gln
545                 550                 555                 560

Ala Ala Lys His Gly Leu Val Lys Met Asn Val Ile Thr Pro Asp Thr
                565                 570                 575

Lys Asp Ile Leu Tyr Ile Glu Leu Ser Asn Gly Asn Leu Ser Asn Ala
            580                 585                 590

Val Val Asp Lys Glu Gln Ala Ala Asp Ala Asn Leu Met Val Asn Lys
        595                 600                 605

Ala Asp Val Asn Arg Ile Leu Leu Gly Gln Val Thr Leu Lys Ala Leu
    610                 615                 620

Leu Ala Ser Gly Asp Ala Lys Leu Thr Gly Asp Lys Thr Ala Phe Ser
625                 630                 635                 640

Lys Ile Ala Asp Ser Met Val Glu Phe Thr Pro Asp Phe Glu Ile Val
                645                 650                 655

Pro Thr Pro Val Lys
            660
```

( 2 ) INFORMATION FOR SEQ ID NO:4:

( i ) SEQUENCE CHARACTERISTICS:
( A ) LENGTH: 831 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( A ) ORGANISM: Shewanella putrefaciens SCRC-2874 (FERM BP- 1625)

( i x ) FEATURE:
( A ) NAME/KEY: CDS
( B ) LOCATION: 1..831

( i x ) FEATURE:
( A ) NAME/KEY: mat_peptide
( B ) LOCATION: 1..831

( x i ) SEQUENCE DESCRIPTION: SEQ ID NO:4:

```
ATG GTA AGA GGC TAT TTG CGC GCT TTA TTG TCA CAA CAT AGT GAA ATA     48
Met Val Arg Gly Tyr Leu Arg Ala Leu Leu Ser Gln His Ser Glu Ile
  1               5                  10                  15

CGC CCC AAT GAA TGG CGC TTT GAA TAT GGC GAC AAA GGT AAG CCT AGA     96
Arg Pro Asn Glu Trp Arg Phe Glu Tyr Gly Asp Lys Gly Lys Pro Arg
             20                  25                  30

TTG AGT GAT GCG CAA TTT GCT CAA ACC GGG GTC CAC TTT AAT GTG AGT    144
Leu Ser Asp Ala Gln Phe Ala Gln Thr Gly Val His Phe Asn Val Ser
         35                  40                  45

CAT AGT GGA GAT TGG CTA TTA GTA GGC ATT TGC ACT GCT GAT AAT AAA    192
His Ser Gly Asp Trp Leu Leu Val Gly Ile Cys Thr Ala Asp Asn Lys
     50                  55                  60

GGC GCC AGT CAG GCA AGC AAG GAG GAA ACT GAC TCT GCT AGT ATT GAG    240
Gly Ala Ser Gln Ala Ser Lys Glu Glu Thr Asp Ser Ala Ser Ile Glu
 65                  70                  75                      80

TTT GGC GTC GAC ATT GAG CGT TGC CGT AAC AGC ACC AAT ATC CAC TCT    288
Phe Gly Val Asp Ile Glu Arg Cys Arg Asn Ser Thr Asn Ile His Ser
                 85                  90                  95

ATT CTT AGT CAT TAT TTC TCT GAA TCA GAA AAG CGA GCC TTG TTA GCG    336
Ile Leu Ser His Tyr Phe Ser Glu Ser Glu Lys Arg Ala Leu Leu Ala
            100                 105                 110

TTA CCA GAG GCC TTG CAG CGA GAC CGC TTT TTT GAT TTG TGG GCG CTC    384
Leu Pro Glu Ala Leu Gln Arg Asp Arg Phe Phe Asp Leu Trp Ala Leu
        115                 120                 125

AAG GAG TCT TAC ATT AAA GCG AAA GGA CTT GGG CTG GCA TTA TCG CTA    432
Lys Glu Ser Tyr Ile Lys Ala Lys Gly Leu Gly Leu Ala Leu Ser Leu
    130                 135                 140

AAA TCT TTT GCG TTT GAC TTC TCT GCA CTG AGC GAA ACT TTT CTT GGA    480
Lys Ser Phe Ala Phe Asp Phe Ser Ala Leu Ser Glu Thr Phe Leu Gly
145                 150                 155                     160

GTT AAT GCA CCT AAA AGC TTG AGC CAT TGT GTT GAT ATT TCC GAT GCT    528
Val Asn Ala Pro Lys Ser Leu Ser His Cys Val Asp Ile Ser Asp Ala
                165                 170                 175

ATT GCG GAT CAC AAG GTT GAG CAT CAA CTT AAT CAG CGA CAG GTT TTG    576
Ile Ala Asp His Lys Val Glu His Gln Leu Asn Gln Arg Gln Val Leu
            180                 185                 190

TTA AAA CAA GAT ATT GGT CTT GCT TTA CTA GAG TCG AGT TCT AAT AAG    624
Leu Lys Gln Asp Ile Gly Leu Ala Leu Leu Glu Ser Ser Ser Asn Lys
        195                 200                 205

CCT AAC GCT GAG CCA CAA AAG TCT GGT TTA GGT TTG ATT GAG GCT AAA    672
Pro Asn Ala Glu Pro Gln Lys Ser Gly Leu Gly Leu Ile Glu Ala Lys
    210                 215                 220

GAA CAG CAA ATG AAC GCT GCT GAT AAT TGG CAT TGT TTA CTG GGC CAT    720
Glu Gln Gln Met Asn Ala Ala Asp Asn Trp His Cys Leu Leu Gly His
225                 230                 235                     240

CTT GAT GAT AGT TAT CGT TTT GCA CTG AGT ATT GGT CAG TGT CAG CAA    768
Leu Asp Asp Ser Tyr Arg Phe Ala Leu Ser Ile Gly Gln Cys Gln Gln
                245                 250                 255

ATA AGT ATT GCA GCA GAA GAA GTG AAT TTT AAA GCT GTT GTT CGA GCT    816
Ile Ser Ile Ala Ala Glu Glu Val Asn Phe Lys Ala Val Val Arg Ala
            260                 265                 270

TCA GCT AAG ACT AGC                                                831
Ser Ala Lys Thr Ser
        275
```

( 2 ) INFORMATION FOR SEQ ID NO:5:

( i ) SEQUENCE CHARACTERISTICS:

( A ) LENGTH: 277 amino acids ( B ) TYPE: amino acid ( D ) TOPOLOGY: linear ( i i ) MOLECULE TYPE: protein ( x i ) SEQUENCE DESCRIPTION: SEQ ID NO:5:

```
Met Val Arg Gly Tyr Leu Arg Ala Leu Leu Ser Gln His Ser Glu Ile
 1               5                  10                  15

Arg Pro Asn Glu Trp Arg Phe Glu Tyr Gly Asp Lys Gly Lys Pro Arg
            20                  25                  30

Leu Ser Asp Ala Gln Phe Ala Gln Thr Gly Val His Phe Asn Val Ser
        35                  40                  45

His Ser Gly Asp Trp Leu Leu Val Gly Ile Cys Thr Ala Asp Asn Lys
    50                  55                  60

Gly Ala Ser Gln Ala Ser Lys Glu Glu Thr Asp Ser Ala Ser Ile Glu
65                  70                  75                  80

Phe Gly Val Asp Ile Glu Arg Cys Arg Asn Ser Thr Asn Ile His Ser
                85                  90                  95

Ile Leu Ser His Tyr Phe Ser Glu Ser Glu Lys Arg Ala Leu Leu Ala
            100                 105                 110

Leu Pro Glu Ala Leu Gln Arg Asp Arg Phe Phe Asp Leu Trp Ala Leu
        115                 120                 125

Lys Glu Ser Tyr Ile Lys Ala Lys Gly Leu Gly Leu Ala Leu Ser Leu
    130                 135                 140

Lys Ser Phe Ala Phe Asp Phe Ser Ala Leu Ser Glu Thr Phe Leu Gly
145                 150                 155                 160

Val Asn Ala Pro Lys Ser Leu Ser His Cys Val Asp Ile Ser Asp Ala
                165                 170                 175

Ile Ala Asp His Lys Val Glu His Gln Leu Asn Gln Arg Gln Val Leu
            180                 185                 190

Leu Lys Gln Asp Ile Gly Leu Ala Leu Leu Glu Ser Ser Ser Asn Lys
        195                 200                 205

Pro Asn Ala Glu Pro Gln Lys Ser Gly Leu Gly Leu Ile Glu Ala Lys
    210                 215                 220

Glu Gln Gln Met Asn Ala Ala Asp Asn Trp His Cys Leu Leu Gly His
225                 230                 235                 240

Leu Asp Asp Ser Tyr Arg Phe Ala Leu Ser Ile Gly Gln Cys Gln Gln
                245                 250                 255

Ile Ser Ile Ala Ala Glu Glu Val Asn Phe Lys Ala Val Val Arg Ala
            260                 265                 270

Ser Ala Lys Thr Ser
        275
```

( 2 ) INFORMATION FOR SEQ ID NO:6:

( i ) SEQUENCE CHARACTERISTICS:
( A ) LENGTH: 2910 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( A ) ORGANISM: Shewanella putrefaciens SCRC-2874 (FERM BP- 1625)

( i x ) FEATURE:
( A ) NAME/KEY: CDS
( B ) LOCATION: 1..2910

( i x ) FEATURE:
( A ) NAME/KEY: mat_peptide ( B ) LOCATION: 1..2910

( x i ) SEQUENCE DESCRIPTION: SEQ ID NO:6:

```
ATG AGT ATG TTT TTA AAT TCA AAA CTT TCG CGC TCA GTC AAA CTT GCC    48
Met Ser Met Phe Leu Asn Ser Lys Leu Ser Arg Ser Val Lys Leu Ala
 1               5                  10                  15

ATA TCC GCA GGC TTA ACA GCC TCG CTA GCT ATG CCT GTT TTT GCA GAA    96
Ile Ser Ala Gly Leu Thr Ala Ser Leu Ala Met Pro Val Phe Ala Glu
            20                  25                  30

GAA ACT GCT GCT GAA GAA CAA ATA GAA AGA GTC GCA GTG ACC GGA TCG   144
Glu Thr Ala Ala Glu Glu Gln Ile Glu Arg Val Ala Val Thr Gly Ser
        35                  40                  45

CGA ATC GCT AAA GCA GAG CTA ACT CAA CCA GCT CCA GTC GTC AGC CTT   192
Arg Ile Ala Lys Ala Glu Leu Thr Gln Pro Ala Pro Val Val Ser Leu
    50                  55                  60

TCA GCC GAA GAA CTG ACA AAA TTT GGT AAT CAA GAT TTA GGT AGC GTA   240
Ser Ala Glu Glu Leu Thr Lys Phe Gly Asn Gln Asp Leu Gly Ser Val
 65                  70                  75                  80

CTA GCA GAA TTA CCT GCT ATT GGT GCA ACC AAC ACT ATT ATT GGT AAT   288
Leu Ala Glu Leu Pro Ala Ile Gly Ala Thr Asn Thr Ile Ile Gly Asn
                 85                  90                  95

AAC AAT AGC AAC TCA AGC GCA GGT GTT AGC TCA GCA GAC TTG CGT CGT   336
Asn Asn Ser Asn Ser Ser Ala Gly Val Ser Ser Ala Asp Leu Arg Arg
            100                 105                 110

CTA GGT GCT AAC AGA ACC TTA GTA TTA GTC AAC GGT AAG CGC TAC GTT   384
Leu Gly Ala Asn Arg Thr Leu Val Leu Val Asn Gly Lys Arg Tyr Val
        115                 120                 125

GCC GGC CAA CCG GGC TCA GCT GAG GTA GAT TTG TCA ACT ATA CCA ACT   432
Ala Gly Gln Pro Gly Ser Ala Glu Val Asp Leu Ser Thr Ile Pro Thr
    130                 135                 140

AGC ATG ATC TCG CGA GTT GAG ATT GTA ACC GGC GGT GCT TCA GCA ATT   480
Ser Met Ile Ser Arg Val Glu Ile Val Thr Gly Gly Ala Ser Ala Ile
145                 150                 155                 160

TAT GGT TCG GAC GCT GTA TCA GGT GTT ATC AAC GTT ATC CTT AAA GAA   528
Tyr Gly Ser Asp Ala Val Ser Gly Val Ile Asn Val Ile Leu Lys Glu
                165                 170                 175

GAC TTT GAA GGC TTT GAG TTT AAC GCA CGT ACT AGC GGT TCT ACT GAA   576
Asp Phe Glu Gly Phe Glu Phe Asn Ala Arg Thr Ser Gly Ser Thr Glu
            180                 185                 190

AGT GTA GGC ACT CAA GAG CAC TCT TTT GAC ATT TTG GGT GGT GCA AAC   624
Ser Val Gly Thr Gln Glu His Ser Phe Asp Ile Leu Gly Gly Ala Asn
        195                 200                 205

GTT GCA GAT GGA CGT GGT AAT GTA ACC TTC TAC GCA GGT TAT GAA CGT   672
Val Ala Asp Gly Arg Gly Asn Val Thr Phe Tyr Ala Gly Tyr Glu Arg
    210                 215                 220

ACA AAA GAA GTC ATG GCT ACC GAC ATT CGC CAA TTC GAT GCT TGG GGA   720
Thr Lys Glu Val Met Ala Thr Asp Ile Arg Gln Phe Asp Ala Trp Gly
225                 230                 235                 240

ACA ATT AAA AAC GAA GCC GAT GGT GGT GAA GAT GAT GGT ATT CCA GAC   768
Thr Ile Lys Asn Glu Ala Asp Gly Gly Glu Asp Asp Gly Ile Pro Asp
                245                 250                 255

AGA CTA CGT GTA CCA CGA GTT TAT TCT GAA ATG ATT AAT GCT ACC GGT   816
Arg Leu Arg Val Pro Arg Val Tyr Ser Glu Met Ile Asn Ala Thr Gly
            260                 265                 270

GTT ATC AAT GCA TTT GGT GGT GGA ATT GGT CGC TCA ACC TTT GAC AGT   864
Val Ile Asn Ala Phe Gly Gly Gly Ile Gly Arg Ser Thr Phe Asp Ser
        275                 280                 285

AAC GGC AAT CCT ATT GCA CAA CAA GAA CGT GAT GGG ACT AAC AGC TTT   912
Asn Gly Asn Pro Ile Ala Gln Gln Glu Arg Asp Gly Thr Asn Ser Phe
    290                 295                 300
```

-continued

```
GCA TTT GGT TCA TTC CCT AAT GGC TGT GAC ACA TGT TTC AAC ACT GAA      960
Ala Phe Gly Ser Phe Pro Asn Gly Cys Asp Thr Cys Phe Asn Thr Glu
305                 310                 315                 320

GCA TAC GAA AAC TAT ATT CCA GGG GTA GAA AGA ATA AAC GTT GGC TCA     1008
Ala Tyr Glu Asn Tyr Ile Pro Gly Val Glu Arg Ile Asn Val Gly Ser
                325                 330                 335

TCA TTC AAC TTT GAT TTT ACC GAT AAC ATT CAA TTT TAC ACT GAC TTC     1056
Ser Phe Asn Phe Asp Phe Thr Asp Asn Ile Gln Phe Tyr Thr Asp Phe
            340                 345                 350

AGA TAT GTA AAG TCA GAT ATT CAG CAA CAA TTT CAG CCT TCA TTC CGT     1104
Arg Tyr Val Lys Ser Asp Ile Gln Gln Gln Phe Gln Pro Ser Phe Arg
        355                 360                 365

TTT GGT AAC ATT AAT ATC AAT GTT GAA GAT AAC GCC TTT TTG AAT GAC     1152
Phe Gly Asn Ile Asn Ile Asn Val Glu Asp Asn Ala Phe Leu Asn Asp
    370                 375                 380

GAC TTG CGT CAG CAA ATG CTC GAT GCG GGT CAA ACC AAT GCT AGT TTT     1200
Asp Leu Arg Gln Gln Met Leu Asp Ala Gly Gln Thr Asn Ala Ser Phe
385                 390                 395                 400

GCC AAG TTT TTT GAT GAA TTA GGA AAT CGC TCA GCA GAA AAT AAA CGC     1248
Ala Lys Phe Phe Asp Glu Leu Gly Asn Arg Ser Ala Glu Asn Lys Arg
                405                 410                 415

GAA CTT TTC CGT TAC GTA GGT GGC TTT AAA GGT GGC TTT GAT ATT AGC     1296
Glu Leu Phe Arg Tyr Val Gly Gly Phe Lys Gly Gly Phe Asp Ile Ser
            420                 425                 430

GAA ACC ATA TTT GAT TAC GAC CTT TAC TAT GTT TAT GGC GAG ACT AAT     1344
Glu Thr Ile Phe Asp Tyr Asp Leu Tyr Tyr Val Tyr Gly Glu Thr Asn
        435                 440                 445

AAC CGT CGT AAA ACC CTT AAT GAC CTA ATT CCT GAT AAC TTT GTC GCA     1392
Asn Arg Arg Lys Thr Leu Asn Asp Leu Ile Pro Asp Asn Phe Val Ala
    450                 455                 460

GCT GTC GAC TCT GTT ATT GAT CCT GAT ACT GGC TTA GCA GCG TGT CGC     1440
Ala Val Asp Ser Val Ile Asp Pro Asp Thr Gly Leu Ala Ala Cys Arg
465                 470                 475                 480

TCA CAA GTA GCA AGC GCT CAA GGC GAT GAC TAT ACA GAT CCC GCG TCT     1488
Ser Gln Val Ala Ser Ala Gln Gly Asp Asp Tyr Thr Asp Pro Ala Ser
                485                 490                 495

GTA AAT GGT AGC GAC TGT GTT GCT TAT AAC CCA TTT GGC ATG GGT CAA     1536
Val Asn Gly Ser Asp Cys Val Ala Tyr Asn Pro Phe Gly Met Gly Gln
            500                 505                 510

GCT TCA GCA GAA GCC CGC GAC TGG GTT TCT GCT GAT GTG ACT CGT GAA     1584
Ala Ser Ala Glu Ala Arg Asp Trp Val Ser Ala Asp Val Thr Arg Glu
        515                 520                 525

GAC AAA ATA ACT CAA CAA GTG ATT GGT GGT ACT CTC GGT ACC GAT TCT     1632
Asp Lys Ile Thr Gln Gln Val Ile Gly Gly Thr Leu Gly Thr Asp Ser
    530                 535                 540

GAA GAA CTA TTT GAG CTT CAA GGT GGT GCA ATC GCT ATG GTT GTT GGT     1680
Glu Glu Leu Phe Glu Leu Gln Gly Gly Ala Ile Ala Met Val Val Gly
545                 550                 555                 560

TTT GAA TAC CGT GAA GAA ACG TCT GGT TCA ACA ACC GAT GAA TTT ACT     1728
Phe Glu Tyr Arg Glu Glu Thr Ser Gly Ser Thr Thr Asp Glu Phe Thr
                565                 570                 575

AAA GCA GGT TTC TTG ACA AGC GCT GCA ACG CCA GAT TCT TAT GGC GAA     1776
Lys Ala Gly Phe Leu Thr Ser Ala Ala Thr Pro Asp Ser Tyr Gly Glu
            580                 585                 590

TAC GAC GTG ACT GAG TAT TTT GTT GAG GTG AAC ATC CCA GTA CTA AAA     1824
Tyr Asp Val Thr Glu Tyr Phe Val Glu Val Asn Ile Pro Val Leu Lys
        595                 600                 605

GAA TTA CCT TTT GCA CAT GAG TTG AGC TTT GAC GGT GCA TAC CGT AAT     1872
Glu Leu Pro Phe Ala His Glu Leu Ser Phe Asp Gly Ala Tyr Arg Asn
    610                 615                 620
```

-continued

```
GCT GAT TAC TCA CAT GCC GGT AAG ACT GAA GCA TGG AAA GCT GGT ATG    1920
Ala Asp Tyr Ser His Ala Gly Lys Thr Glu Ala Trp Lys Ala Gly Met
625                 630                 635                 640

TTC TAC TCA CCA TTA GAG CAA CTT GCA TTA CGT GGT ACG GTA GGT GAA    1968
Phe Tyr Ser Pro Leu Glu Gln Leu Ala Leu Arg Gly Thr Val Gly Glu
                645                 650                 655

GCA GTA CGA GCA CCA AAC ATT GCA GAA GCC TTT AGT CCA CGC TCT CCT    2016
Ala Val Arg Ala Pro Asn Ile Ala Glu Ala Phe Ser Pro Arg Ser Pro
            660                 665                 670

GGT TTT GGC CGC GTT TCA GAT CCA TGT GAT GCA GAT AAC ATT AAT GAC    2064
Gly Phe Gly Arg Val Ser Asp Pro Cys Asp Ala Asp Asn Ile Asn Asp
        675                 680                 685

GAT CCG GAT CGC GTG TCA AAC TGT GCA GCA TTG GGG ATC CCT CCA GGA    2112
Asp Pro Asp Arg Val Ser Asn Cys Ala Ala Leu Gly Ile Pro Pro Gly
    690                 695                 700

TTC CAA GCT AAT GAT AAC GTC AGT GTA GAT ACC TTA TCT GGT GGT AAC    2160
Phe Gln Ala Asn Asp Asn Val Ser Val Asp Thr Leu Ser Gly Gly Asn
705                 710                 715                 720

CCA GAT CTA AAA CCT GAA ACA TCA ACA TCC TTT ACA GGT GGT CTT GTT    2208
Pro Asp Leu Lys Pro Glu Thr Ser Thr Ser Phe Thr Gly Gly Leu Val
                725                 730                 735

TGG ACA CCA ACG TTT GCT GAC AAT CTA TCA TTC ACT GTC GAT TAT TAT    2256
Trp Thr Pro Thr Phe Ala Asp Asn Leu Ser Phe Thr Val Asp Tyr Tyr
            740                 745                 750

GAT ATT CAA ATT GAG GAT GCT ATT TTG TCA GTA GCC ACC CAG ACT GTG    2304
Asp Ile Gln Ile Glu Asp Ala Ile Leu Ser Val Ala Thr Gln Thr Val
        755                 760                 765

GCT GAT AAC TGT GTT GAC TCA ACT GGC GGA CCT GAC ACC GAC TTC TGT    2352
Ala Asp Asn Cys Val Asp Ser Thr Gly Gly Pro Asp Thr Asp Phe Cys
    770                 775                 780

AGT CAA GTT GAT CGT AAT CCA ACG ACC TAT GAT ATT GAA CTT GTT CGC    2400
Ser Gln Val Asp Arg Asn Pro Thr Thr Tyr Asp Ile Glu Leu Val Arg
785                 790                 795                 800

TCT GGT TAT CTA AAT GCC GCG GCA TTG AAT ACC AAA GGT ATT GAA TTT    2448
Ser Gly Tyr Leu Asn Ala Ala Ala Leu Asn Thr Lys Gly Ile Glu Phe
                805                 810                 815

CAA GCT GCA TAC TCA TTA GAT CTA GAG TCT TTC AAC GCG CCT GGT GAA    2496
Gln Ala Ala Tyr Ser Leu Asp Leu Glu Ser Phe Asn Ala Pro Gly Glu
            820                 825                 830

CTA CGC TTC AAC CTA TTG GGG AAC CAA TTA CTT GAA CTA GAA CGT CTT    2544
Leu Arg Phe Asn Leu Leu Gly Asn Gln Leu Leu Glu Leu Glu Arg Leu
        835                 840                 845

GAA TTC CAA AAT CGT CCT GAT GAG ATT AAT GAT GAA AAA GGC GAA GTA    2592
Glu Phe Gln Asn Arg Pro Asp Glu Ile Asn Asp Glu Lys Gly Glu Val
    850                 855                 860

GGT GAT CCA GAG CTG CAG TTC CGC CTA GGC ATC GAT TAC CGT CTA GAT    2640
Gly Asp Pro Glu Leu Gln Phe Arg Leu Gly Ile Asp Tyr Arg Leu Asp
865                 870                 875                 880

GAT CTA AGT GTT AGC TGG AAC ACG CGT TAT ATT GAT AGC GTA GTA ACT    2688
Asp Leu Ser Val Ser Trp Asn Thr Arg Tyr Ile Asp Ser Val Val Thr
                885                 890                 895

TAT GAT GTC TCT GAA AAT GGT GGC TCT CCT GAA GAT TTA TAT CCA GGC    2736
Tyr Asp Val Ser Glu Asn Gly Gly Ser Pro Glu Asp Leu Tyr Pro Gly
            900                 905                 910

CAC ATA GGC TCA ATG ACA ACT CAT GAC TTG AGC GCT ACA TAC TAC ATC    2784
His Ile Gly Ser Met Thr Thr His Asp Leu Ser Ala Thr Tyr Tyr Ile
        915                 920                 925

AAT GAG AAC TTC ATG ATT AAC GGT GGT GTA CGT AAC CTA TTT GAC GCA    2832
Asn Glu Asn Phe Met Ile Asn Gly Gly Val Arg Asn Leu Phe Asp Ala
    930                 935                 940
```

-continued

```
CTT CCA CCT GGA TAC ACT AAC GAT GCG CTA TAT GAT CTA GTT GGT CGC        2880
Leu Pro Pro Gly Tyr Thr Asn Asp Ala Leu Tyr Asp Leu Val Gly Arg
945                 950                 955                 960

CGT GCA TTC CTA GGT ATT AAG GTA ATG ATG                                2910
Arg Ala Phe Leu Gly Ile Lys Val Met Met
                965                 970
```

( 2 ) INFORMATION FOR SEQ ID NO:7:

( i ) SEQUENCE CHARACTERISTICS:
( A ) LENGTH: 970 amino acids
( B ) TYPE: amino acid
( D ) TOPOLOGY: linear ( i i ) MOLECULE TYPE: protein ( x i ) SEQUENCE DESCRIPTION: SEQ ID NO:7:

```
Met Ser Met Phe Leu Asn Ser Lys Leu Ser Arg Ser Val Lys Leu Ala
  1               5                  10                  15

Ile Ser Ala Gly Leu Thr Ala Ser Leu Ala Met Pro Val Phe Ala Glu
             20                  25                  30

Glu Thr Ala Ala Glu Glu Gln Ile Glu Arg Val Ala Val Thr Gly Ser
         35                  40                  45

Arg Ile Ala Lys Ala Glu Leu Thr Gln Pro Ala Pro Val Val Ser Leu
     50                  55                  60

Ser Ala Glu Glu Leu Thr Lys Phe Gly Asn Gln Asp Leu Gly Ser Val
 65                  70                  75                  80

Leu Ala Glu Leu Pro Ala Ile Gly Ala Thr Asn Thr Ile Ile Gly Asn
                 85                  90                  95

Asn Asn Ser Asn Ser Ser Ala Gly Val Ser Ser Ala Asp Leu Arg Arg
            100                 105                 110

Leu Gly Ala Asn Arg Thr Leu Val Leu Val Asn Gly Lys Arg Tyr Val
        115                 120                 125

Ala Gly Gln Pro Gly Ser Ala Glu Val Asp Leu Ser Thr Ile Pro Thr
    130                 135                 140

Ser Met Ile Ser Arg Val Glu Ile Val Thr Gly Gly Ala Ser Ala Ile
145                 150                 155                 160

Tyr Gly Ser Asp Ala Val Ser Gly Val Ile Asn Val Ile Leu Lys Glu
                165                 170                 175

Asp Phe Glu Gly Phe Glu Phe Asn Ala Arg Thr Ser Gly Ser Thr Glu
            180                 185                 190

Ser Val Gly Thr Gln Glu His Ser Phe Asp Ile Leu Gly Gly Ala Asn
        195                 200                 205

Val Ala Asp Gly Arg Gly Asn Val Thr Phe Tyr Ala Gly Tyr Glu Arg
    210                 215                 220

Thr Lys Glu Val Met Ala Thr Asp Ile Arg Gln Phe Asp Ala Trp Gly
225                 230                 235                 240

Thr Ile Lys Asn Glu Ala Asp Gly Gly Glu Asp Asp Gly Ile Pro Asp
                245                 250                 255

Arg Leu Arg Val Pro Arg Val Tyr Ser Glu Met Ile Asn Ala Thr Gly
            260                 265                 270

Val Ile Asn Ala Phe Gly Gly Gly Ile Gly Arg Ser Thr Phe Asp Ser
        275                 280                 285

Asn Gly Asn Pro Ile Ala Gln Gln Glu Arg Asp Gly Thr Asn Ser Phe
    290                 295                 300

Ala Phe Gly Ser Phe Pro Asn Gly Cys Asp Thr Cys Phe Asn Thr Glu
305                 310                 315                 320
```

-continued

```
Ala Tyr Glu Asn Tyr Ile Pro Gly Val Glu Arg Ile Asn Val Gly Ser
                325                 330                 335

Ser Phe Asn Phe Asp Phe Thr Asp Asn Ile Gln Phe Tyr Thr Asp Phe
            340                 345                 350

Arg Tyr Val Lys Ser Asp Ile Gln Gln Gln Phe Gln Pro Ser Phe Arg
        355                 360                 365

Phe Gly Asn Ile Asn Ile Asn Val Glu Asp Asn Ala Phe Leu Asn Asp
    370                 375                 380

Asp Leu Arg Gln Gln Met Leu Asp Ala Gly Gln Thr Asn Ala Ser Phe
385                 390                 395                 400

Ala Lys Phe Phe Asp Glu Leu Gly Asn Arg Ser Ala Glu Asn Lys Arg
                405                 410                 415

Glu Leu Phe Arg Tyr Val Gly Gly Phe Lys Gly Gly Phe Asp Ile Ser
            420                 425                 430

Glu Thr Ile Phe Asp Tyr Asp Leu Tyr Tyr Val Tyr Gly Glu Thr Asn
        435                 440                 445

Asn Arg Arg Lys Thr Leu Asn Asp Leu Ile Pro Asp Asn Phe Val Ala
    450                 455                 460

Ala Val Asp Ser Val Ile Asp Pro Asp Thr Gly Leu Ala Ala Cys Arg
465                 470                 475                 480

Ser Gln Val Ala Ser Ala Gln Gly Asp Asp Tyr Thr Asp Pro Ala Ser
                485                 490                 495

Val Asn Gly Ser Asp Cys Val Ala Tyr Asn Pro Phe Gly Met Gly Gln
            500                 505                 510

Ala Ser Ala Glu Ala Arg Asp Trp Val Ser Ala Asp Val Thr Arg Glu
        515                 520                 525

Asp Lys Ile Thr Gln Gln Val Ile Gly Gly Thr Leu Gly Thr Asp Ser
    530                 535                 540

Glu Glu Leu Phe Glu Leu Gln Gly Gly Ala Ile Ala Met Val Val Gly
545                 550                 555                 560

Phe Glu Tyr Arg Glu Glu Thr Ser Gly Ser Thr Thr Asp Glu Phe Thr
                565                 570                 575

Lys Ala Gly Phe Leu Thr Ser Ala Ala Thr Pro Asp Ser Tyr Gly Glu
            580                 585                 590

Tyr Asp Val Thr Glu Tyr Phe Val Glu Val Asn Ile Pro Val Leu Lys
        595                 600                 605

Glu Leu Pro Phe Ala His Glu Leu Ser Phe Asp Gly Ala Tyr Arg Asn
    610                 615                 620

Ala Asp Tyr Ser His Ala Gly Lys Thr Glu Ala Trp Lys Ala Gly Met
625                 630                 635                 640

Phe Tyr Ser Pro Leu Glu Gln Leu Ala Leu Arg Gly Thr Val Gly Glu
                645                 650                 655

Ala Val Arg Ala Pro Asn Ile Ala Glu Ala Phe Ser Pro Arg Ser Pro
            660                 665                 670

Gly Phe Gly Arg Val Ser Asp Pro Cys Asp Ala Asp Asn Ile Asn Asp
        675                 680                 685

Asp Pro Asp Arg Val Ser Asn Cys Ala Ala Leu Gly Ile Pro Pro Gly
    690                 695                 700

Phe Gln Ala Asn Asp Asn Val Ser Val Asp Thr Leu Ser Gly Gly Asn
705                 710                 715                 720

Pro Asp Leu Lys Pro Glu Thr Ser Thr Ser Phe Thr Gly Gly Leu Val
                725                 730                 735

Trp Thr Pro Thr Phe Ala Asp Asn Leu Ser Phe Thr Val Asp Tyr Tyr
            740                 745                 750
```

```
Asp Ile Gln Ile Glu Asp Ala Ile Leu Ser Val Ala Thr Gln Thr Val
        755                 760                 765

Ala Asp Asn Cys Val Asp Ser Thr Gly Gly Pro Asp Thr Asp Phe Cys
    770                 775                 780

Ser Gln Val Asp Arg Asn Pro Thr Thr Tyr Asp Ile Glu Leu Val Arg
785                 790                 795                     800

Ser Gly Tyr Leu Asn Ala Ala Ala Leu Asn Thr Lys Gly Ile Glu Phe
                805                 810                     815

Gln Ala Ala Tyr Ser Leu Asp Leu Glu Ser Phe Asn Ala Pro Gly Glu
            820                 825                 830

Leu Arg Phe Asn Leu Leu Gly Asn Gln Leu Leu Glu Leu Glu Arg Leu
        835                 840                 845

Glu Phe Gln Asn Arg Pro Asp Glu Ile Asn Asp Glu Lys Gly Glu Val
    850                 855                 860

Gly Asp Pro Glu Leu Gln Phe Arg Leu Gly Ile Asp Tyr Arg Leu Asp
865                 870                 875                     880

Asp Leu Ser Val Ser Trp Asn Thr Arg Tyr Ile Asp Ser Val Val Thr
                885                 890                     895

Tyr Asp Val Ser Glu Asn Gly Gly Ser Pro Glu Asp Leu Tyr Pro Gly
            900                 905                 910

His Ile Gly Ser Met Thr Thr His Asp Leu Ser Ala Thr Tyr Tyr Ile
        915                 920                 925

Asn Glu Asn Phe Met Ile Asn Gly Gly Val Arg Asn Leu Phe Asp Ala
    930                 935                 940

Leu Pro Pro Gly Tyr Thr Asn Asp Ala Leu Tyr Asp Leu Val Gly Arg
945                 950                 955                     960

Arg Ala Phe Leu Gly Ile Lys Val Met Met
                965                 970
```

( 2 ) INFORMATION FOR SEQ ID NO:8:

( i ) SEQUENCE CHARACTERISTICS:
( A ) LENGTH: 864 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( A ) ORGANISM: Shewanella putrefaciens SCRC-2874 (FERM BP- 1625)

( i x ) FEATURE:
( A ) NAME/KEY: CDS
( B ) LOCATION: 1..864

( i x ) FEATURE:
( A ) NAME/KEY: mat_peptide
( B ) LOCATION: 1..864

( x i ) SEQUENCE DESCRIPTION: SEQ ID NO:8:

```
ATG GCA AAA ATA AAT AGT GAA CAC TTG GAT GAA GCT ACT ATT ACT TCG      48
Met Ala Lys Ile Asn Ser Glu His Leu Asp Glu Ala Thr Ile Thr Ser
  1               5                  10                  15

AAT AAG TGT ACG CAA ACA GAG ACT GAG GCT CGG CAT AGA AAT GCC ACT      96
Asn Lys Cys Thr Gln Thr Glu Thr Glu Ala Arg His Arg Asn Ala Thr
             20                  25                  30

ACA ACA CCT GAG ATG CGC CGA TTC ATA CAA GAG TCG GAT CTC AGT GTT     144
Thr Thr Pro Glu Met Arg Arg Phe Ile Gln Glu Ser Asp Leu Ser Val
         35                  40                  45
```

-continued

```
AGC CAA CTG TCT AAA ATA TTA AAT ATC AGT GAA GCT ACC GTA CGT AAG      192
Ser Gln Leu Ser Lys Ile Leu Asn Ile Ser Glu Ala Thr Val Arg Lys
     50                  55                  60

TGG CGC AAG CGT GAC TCT GTC GAA AAC TGT CCT AAT ACC CCG CAC CAT      240
Trp Arg Lys Arg Asp Ser Val Glu Asn Cys Pro Asn Thr Pro His His
 65                  70                  75                  80

CTC AAT ACC ACG CTA ACC CCT TTG CAA GAA TAT GTG GTT GTG GGC CTG      288
Leu Asn Thr Thr Leu Thr Pro Leu Gln Glu Tyr Val Val Val Gly Leu
                 85                  90                  95

CGT TAT CAA TTG AAA ATG CCA TTA GAC AGA TTG CTC AAA GCA ACC CAA      336
Arg Tyr Gln Leu Lys Met Pro Leu Asp Arg Leu Leu Lys Ala Thr Gln
            100                 105                 110

GAG TTT ATC AAT CCA AAC GTG TCG CGC TCA GGT TTA GCA AGA TGT TTG      384
Glu Phe Ile Asn Pro Asn Val Ser Arg Ser Gly Leu Ala Arg Cys Leu
        115                 120                 125

AAG CGT TAT GGC GTT TCA CGG GTG AGT GAT ATC CAA AGC CCA CAC GTA      432
Lys Arg Tyr Gly Val Ser Arg Val Ser Asp Ile Gln Ser Pro His Val
    130                 135                 140

CCA ATG CGC TAC TTT AAT CAA ATT CCA GTC ACT CAA GGC AGC GAT GTG      480
Pro Met Arg Tyr Phe Asn Gln Ile Pro Val Thr Gln Gly Ser Asp Val
145                 150                 155                 160

CAA ACC TAC ACC CTG CAC TAT GAA ACG CTG GCA AAA ACC TTA GCC TTA      528
Gln Thr Tyr Thr Leu His Tyr Glu Thr Leu Ala Lys Thr Leu Ala Leu
                165                 170                 175

CCT AGT ACC GAT GGT GAC AAT GTG GTG CAA GTG GTG TCT CTC ACC ATT      576
Pro Ser Thr Asp Gly Asp Asn Val Val Gln Val Val Ser Leu Thr Ile
            180                 185                 190

CCA CCA AAG TTA ACC GAA GAA GCA CCC AGT TCA ATT TTG CTC GGC ATT      624
Pro Pro Lys Leu Thr Glu Glu Ala Pro Ser Ser Ile Leu Leu Gly Ile
        195                 200                 205

GAT CCT CAT AGC GAC TGG ATC TAT CTC GAC ATA TAC CAA GAT GGC AAT      672
Asp Pro His Ser Asp Trp Ile Tyr Leu Asp Ile Tyr Gln Asp Gly Asn
    210                 215                 220

ACA CAA GCC ACG AAT AGA TAT ATG GCT TAT GTG CTA AAA CAC GGG CCA      720
Thr Gln Ala Thr Asn Arg Tyr Met Ala Tyr Val Leu Lys His Gly Pro
225                 230                 235                 240

TTC CAT TTA CGA AAG TTA CTC GTG CGT AAC TAT CAC ACC TTT TTA CAG      768
Phe His Leu Arg Lys Leu Leu Val Arg Asn Tyr His Thr Phe Leu Gln
                245                 250                 255

CGC TTT CCT GGA GCG ACG CAA AAT CGC CGC CCC TCT AAA GAT ATG CCT      816
Arg Phe Pro Gly Ala Thr Gln Asn Arg Arg Pro Ser Lys Asp Met Pro
            260                 265                 270

GAA ACA ATC AAC AAG ACG CCT GAA ACA CAG GCA CCC AGT GGA GAC TCA      864
Glu Thr Ile Asn Lys Thr Pro Glu Thr Gln Ala Pro Ser Gly Asp Ser
        275                 280                 285
```

( 2 ) INFORMATION FOR SEQ ID NO:9:

( i ) SEQUENCE CHARACTERISTICS:
( A ) LENGTH: 288 amino acids
( B ) TYPE: amino acid
( D ) TOPOLOGY: linear ( i i ) MOLECULE TYPE: protein ( x i ) SEQUENCE DESCRIPTION: SEQ ID NO:9:

```
Met Ala Lys Ile Asn Ser Glu His Leu Asp Glu Ala Thr Ile Thr Ser
  1               5                  10                  15

Asn Lys Cys Thr Gln Thr Glu Thr Glu Ala Arg His Arg Asn Ala Thr
             20                  25                  30

Thr Thr Pro Glu Met Arg Arg Phe Ile Gln Glu Ser Asp Leu Ser Val
         35                  40                  45
```

Ser Gln Leu Ser Lys Ile Leu Asn Ile Ser Glu Ala Thr Val Arg Lys
50 55 60

Trp Arg Lys Arg Asp Ser Val Glu Asn Cys Pro Asn Thr Pro His His
65 70 75 80

Leu Asn Thr Thr Leu Thr Pro Leu Gln Glu Tyr Val Val Val Gly Leu
85 90 95

Arg Tyr Gln Leu Lys Met Pro Leu Asp Arg Leu Leu Lys Ala Thr Gln
100 105 110

Glu Phe Ile Asn Pro Asn Val Ser Arg Ser Gly Leu Ala Arg Cys Leu
115 120 125

Lys Arg Tyr Gly Val Ser Arg Val Ser Asp Ile Gln Ser Pro His Val
130 135 140

Pro Met Arg Tyr Phe Asn Gln Ile Pro Val Thr Gln Gly Ser Asp Val
145 150 155 160

Gln Thr Tyr Thr Leu His Tyr Glu Thr Leu Ala Lys Thr Leu Ala Leu
165 170 175

Pro Ser Thr Asp Gly Asp Asn Val Val Gln Val Val Ser Leu Thr Ile
180 185 190

Pro Pro Lys Leu Thr Glu Glu Ala Pro Ser Ser Ile Leu Leu Gly Ile
195 200 205

Asp Pro His Ser Asp Trp Ile Tyr Leu Asp Ile Tyr Gln Asp Gly Asn
210 215 220

Thr Gln Ala Thr Asn Arg Tyr Met Ala Tyr Val Leu Lys His Gly Pro
225 230 235 240

Phe His Leu Arg Lys Leu Leu Val Arg Asn Tyr His Thr Phe Leu Gln
245 250 255

Arg Phe Pro Gly Ala Thr Gln Asn Arg Arg Pro Ser Lys Asp Met Pro
260 265 270

Glu Thr Ile Asn Lys Thr Pro Glu Thr Gln Ala Pro Ser Gly Asp Ser
275 280 285

( 2 ) INFORMATION FOR SEQ ID NO:10:

( i ) SEQUENCE CHARACTERISTICS:
( A ) LENGTH: 8268 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( A ) ORGANISM: Shewanella putrefaciens SCRC-2874 (FERM BP- 1625)

( i x ) FEATURE:
( A ) NAME/KEY: CDS
( B ) LOCATION: 1..8268

( i x ) FEATURE:
( A ) NAME/KEY: mat_peptide
( B ) LOCATION: 1..8268

( x i ) SEQUENCE DESCRIPTION: SEQ ID NO:10:

ATG AGC CAG ACC TCT AAA CCT ACA AAC TCA GCA ACT GAG CAA GCA CAA 48
Met Ser Gln Thr Ser Lys Pro Thr Asn Ser Ala Thr Glu Gln Ala Gln
1 5 10 15

GAC TCA CAA GCT GAC TCT CGT TTA AAT AAA CGA CTA AAA GAT ATG CCA 96
Asp Ser Gln Ala Asp Ser Arg Leu Asn Lys Arg Leu Lys Asp Met Pro
20 25 30

ATT GCT ATT GTT GGC ATG GCG AGT ATT TTT GCA AAC TCT CGC TAT TTG 144

-continued

```
Ile Ala Ile Val Gly Met Ala Ser Ile Phe Ala Asn Ser Arg Tyr Leu
        35                  40                  45

AAT AAG TTT TGG GAC TTA ATC AGC GAA AAA ATT GAT GCG ATT ACT GAA     192
Asn Lys Phe Trp Asp Leu Ile Ser Glu Lys Ile Asp Ala Ile Thr Glu
    50                  55                  60

TTA CCA TCA ACT CAC TGG CAG CCT GAA GAA TAT TAC GAC GCA GAT AAA     240
Leu Pro Ser Thr His Trp Gln Pro Glu Glu Tyr Tyr Asp Ala Asp Lys
65                  70                  75                  80

ACC GCA GCA GAC AAA AGC TAC TGT AAA CGT GGT GGC TTT TTG CCA GAT     288
Thr Ala Ala Asp Lys Ser Tyr Cys Lys Arg Gly Gly Phe Leu Pro Asp
                85                  90                  95

GTA GAC TTC AAC CCA ATG GAG TTT GGC CTG CCG CCA AAC ATT TTG GAA     336
Val Asp Phe Asn Pro Met Glu Phe Gly Leu Pro Pro Asn Ile Leu Glu
            100                 105                 110

CTG ACC GAT TCA TCG CAA CTA TTA TCA CTC ATC GTT GCT AAA GAA GTG     384
Leu Thr Asp Ser Ser Gln Leu Leu Ser Leu Ile Val Ala Lys Glu Val
        115                 120                 125

TTG GCT GAT GCT AAC TTA CCT GAG AAT TAC GAC CGC GAT AAA ATT GGT     432
Leu Ala Asp Ala Asn Leu Pro Glu Asn Tyr Asp Arg Asp Lys Ile Gly
    130                 135                 140

ATC ACC TTA GGT GTC GGC GGT GGT CAA AAA ATT AGC CAC AGC CTA ACA     480
Ile Thr Leu Gly Val Gly Gly Gly Gln Lys Ile Ser His Ser Leu Thr
145                 150                 155                 160

GCG CGT CTG CAA TAC CCA GTA TTG AAG AAA GTA TTC GCC AAT AGC GGC     528
Ala Arg Leu Gln Tyr Pro Val Leu Lys Lys Val Phe Ala Asn Ser Gly
                165                 170                 175

ATT AGT GAC ACC GAC AGC GAA ATG CTT ATC AAG AAA TTC CAA GAC CAA     576
Ile Ser Asp Thr Asp Ser Glu Met Leu Ile Lys Lys Phe Gln Asp Gln
            180                 185                 190

TAT GTA CAC TGG GAA GAA AAC TCG TTC CCA GGT TCA CTT GGT AAC GTT     624
Tyr Val His Trp Glu Glu Asn Ser Phe Pro Gly Ser Leu Gly Asn Val
        195                 200                 205

ATT GCG GGC CGT ATC GCC AAC CGC TTC GAT TTT GGC GGC ATG AAC TGT     672
Ile Ala Gly Arg Ile Ala Asn Arg Phe Asp Phe Gly Gly Met Asn Cys
    210                 215                 220

GTG GTT GAT GCT GCC TGT GCT GGA TCA CTT GCT GCT ATG CGT ATG GCG     720
Val Val Asp Ala Ala Cys Ala Gly Ser Leu Ala Ala Met Arg Met Ala
225                 230                 235                 240

CTA ACA GAG CTA ACT GAA GGT CGC TCT GAA ATG ATG ATC ACC GGT GGT     768
Leu Thr Glu Leu Thr Glu Gly Arg Ser Glu Met Met Ile Thr Gly Gly
                245                 250                 255

GTG TGT ACT GAT AAC TCA CCC TCT ATG TAT ATG AGC TTT TCA AAA ACG     816
Val Cys Thr Asp Asn Ser Pro Ser Met Tyr Met Ser Phe Ser Lys Thr
            260                 265                 270

CCC GCC TTT ACC ACT AAC GAA ACC ATT CAG CCA TTT GAT ATC GAC TCA     864
Pro Ala Phe Thr Thr Asn Glu Thr Ile Gln Pro Phe Asp Ile Asp Ser
        275                 280                 285

AAA GGC ATG ATG ATT GGT GAA GGT ATT GGC ATG GTG GCG CTA AAG CGT     912
Lys Gly Met Met Ile Gly Glu Gly Ile Gly Met Val Ala Leu Lys Arg
    290                 295                 300

CTT GAA GAT GCA GAG CGC GAT GGC GAC CGC ATT TAC TCT GTA ATT AAA     960
Leu Glu Asp Ala Glu Arg Asp Gly Asp Arg Ile Tyr Ser Val Ile Lys
305                 310                 315                 320

GGT GTG GGT GCA TCA TCT GAC GGT AAG TTT AAA TCA ATC TAT GCC CCT    1008
Gly Val Gly Ala Ser Ser Asp Gly Lys Phe Lys Ser Ile Tyr Ala Pro
                325                 330                 335

CGC CCA TCA GGC CAA GCT AAA GCA CTT AAC CGT GCC TAT GAT GAC GCA    1056
Arg Pro Ser Gly Gln Ala Lys Ala Leu Asn Arg Ala Tyr Asp Asp Ala
            340                 345                 350

GGT TTT GCG CCG CAT ACC TTA GGT CTA ATT GAA GCT CAC GGA ACA GGT    1104
```

-continued

```
Gly Phe Ala Pro His Thr Leu Gly Leu Ile Glu Ala His Gly Thr Gly
        355                 360                 365

ACT GCA GCA GGT GAC GCG GCA GAG TTT GCC GGC CTT TGC TCA GTA TTT     1152
Thr Ala Ala Gly Asp Ala Ala Glu Phe Ala Gly Leu Cys Ser Val Phe
    370                 375                 380

GCT GAA GGC AAC GAT ACC AAG CAA CAC ATT GCG CTA GGT TCA GTT AAA     1200
Ala Glu Gly Asn Asp Thr Lys Gln His Ile Ala Leu Gly Ser Val Lys
385                 390                 395                     400

TCA CAA ATT GGT CAT ACT AAA TCA ACT GCA GGT ACA GCA GGT TTA ATT     1248
Ser Gln Ile Gly His Thr Lys Ser Thr Ala Gly Thr Ala Gly Leu Ile
                405                 410                 415

AAA GCT GCT CTT GCT TTG CAT CAC AAG GTA CTG CCG CCG ACC ATT AAC     1296
Lys Ala Ala Leu Ala Leu His His Lys Val Leu Pro Pro Thr Ile Asn
            420                 425                 430

GTT AGT CAG CCA AGC CCT AAA CTT GAT ATC GAA AAC TCA CCG TTT TAT     1344
Val Ser Gln Pro Ser Pro Lys Leu Asp Ile Glu Asn Ser Pro Phe Tyr
        435                 440                 445

CTA AAC ACT GAG ACT CGT CCA TGG TTA CCA CGT GTT GAT GGT ACG CCG     1392
Leu Asn Thr Glu Thr Arg Pro Trp Leu Pro Arg Val Asp Gly Thr Pro
    450                 455                 460

CGC CGC GCG GGT ATT AGC TCA TTT GGT TTT GGT GGC ACT AAC TTC CAT     1440
Arg Arg Ala Gly Ile Ser Ser Phe Gly Phe Gly Gly Thr Asn Phe His
465                 470                 475                     480

TTT GTA CTA GAA GAG TAC AAC CAA GAA CAC AGC CGT ACT GAT AGC GAA     1488
Phe Val Leu Glu Glu Tyr Asn Gln Glu His Ser Arg Thr Asp Ser Glu
                485                 490                 495

AAA GCT AAG TAT CGT CAA CGC CAA GTG GCG CAA AGC TTC CTT GTT AGC     1536
Lys Ala Lys Tyr Arg Gln Arg Gln Val Ala Gln Ser Phe Leu Val Ser
            500                 505                 510

GCA AGC GAT AAA GCA TCG CTA ATT AAC GAG TTA AAC GTA CTA GCA GCA     1584
Ala Ser Asp Lys Ala Ser Leu Ile Asn Glu Leu Asn Val Leu Ala Ala
        515                 520                 525

TCT GCA AGC CAA GCT GAG TTT ATC CTC AAA GAT GCA GCA GCA AAC TAT     1632
Ser Ala Ser Gln Ala Glu Phe Ile Leu Lys Asp Ala Ala Ala Asn Tyr
    530                 535                 540

GGC GTA CGT GAG CTT GAT AAA AAT GCA CCA CGG ATC GGT TTA GTT GCA     1680
Gly Val Arg Glu Leu Asp Lys Asn Ala Pro Arg Ile Gly Leu Val Ala
545                 550                 555                     560

AAC ACA GCT GAA GAG TTA GCA GGC CTA ATT AAG CAA GCA CTT GCC AAA     1728
Asn Thr Ala Glu Glu Leu Ala Gly Leu Ile Lys Gln Ala Leu Ala Lys
                565                 570                 575

CTA GCA GCT AGC GAT GAT AAC GCA TGG CAG CTA CCT GGT GGC ACT AGC     1776
Leu Ala Ala Ser Asp Asp Asn Ala Trp Gln Leu Pro Gly Gly Thr Ser
            580                 585                 590

TAC CGC GCC GCT GCA GTA GAA GGT AAA GTT GCC GCA CTG TTT GCT GGC     1824
Tyr Arg Ala Ala Ala Val Glu Gly Lys Val Ala Ala Leu Phe Ala Gly
        595                 600                 605

CAA GGT TCA CAA TAT CTC AAT ATG GGC CGT GAC CTT ACT TGT TAT TAC     1872
Gln Gly Ser Gln Tyr Leu Asn Met Gly Arg Asp Leu Thr Cys Tyr Tyr
    610                 615                 620

CCA GAG ATG CGT CAG CAA TTT GTA ACT GCA GAT AAA GTA TTT GCC GCA     1920
Pro Glu Met Arg Gln Gln Phe Val Thr Ala Asp Lys Val Phe Ala Ala
625                 630                 635                     640

AAT GAT AAA ACG CCG TTA TCG CAA ACT CTG TAT CCA AAG CCT GTA TTT     1968
Asn Asp Lys Thr Pro Leu Ser Gln Thr Leu Tyr Pro Lys Pro Val Phe
                645                 650                 655

AAT AAA GAT GAA TTA AAG GCT CAA GAA GCC ATT TTG ACC AAT ACC GCC     2016
Asn Lys Asp Glu Leu Lys Ala Gln Glu Ala Ile Leu Thr Asn Thr Ala
            660                 665                 670

AAT GCC CAA AGC GCA ATT GGT GCG ATT TCA ATG GGT CAA TAC GAT TTG     2064
```

-continued

```
Asn Ala Gln Ser Ala Ile Gly Ala Ile Ser Met Gly Gln Tyr Asp Leu
        675                 680                 685

TTT ACT GCG GCT GGC TTT AAT GCC GAC ATG GTT GCA GGC CAT AGC TTT     2112
Phe Thr Ala Ala Gly Phe Asn Ala Asp Met Val Ala Gly His Ser Phe
    690                 695                 700

GGT GAG CTA AGT GCA CTG TGT GCT GCA GGT GTT ATT TCA GCT GAT GAC     2160
Gly Glu Leu Ser Ala Leu Cys Ala Ala Gly Val Ile Ser Ala Asp Asp
705                 710                 715                 720

TAC TAC AAG CTG GCT TTT GCT CGT GGT GAG GCT ATG GCA ACA AAA GCA     2208
Tyr Tyr Lys Leu Ala Phe Ala Arg Gly Glu Ala Met Ala Thr Lys Ala
                725                 730                 735

CCG GCT AAA GAC GGC GTT GAA GCA GAT GCA GGA GCA ATG TTT GCA ATC     2256
Pro Ala Lys Asp Gly Val Glu Ala Asp Ala Gly Ala Met Phe Ala Ile
            740                 745                 750

ATA ACC AAG AGT GCT GCA GAC CTT GAA ACC GTT GAA GCC ACC ATC GCT     2304
Ile Thr Lys Ser Ala Ala Asp Leu Glu Thr Val Glu Ala Thr Ile Ala
        755                 760                 765

AAA TTT GAT GGG GTG AAA GTC GCT AAC TAT AAC GCG CCA ACG CAA TCA     2352
Lys Phe Asp Gly Val Lys Val Ala Asn Tyr Asn Ala Pro Thr Gln Ser
    770                 775                 780

GTA ATT GCA GGC CCA ACA GCA ACT ACC GCT GAT GCG GCT AAA GCG CTA     2400
Val Ile Ala Gly Pro Thr Ala Thr Thr Ala Asp Ala Ala Lys Ala Leu
785                 790                 795                 800

ACT GAG CTT GGT TAC AAA GCG ATT AAC CTG CCA GTA TCA GGT GCA TTC     2448
Thr Glu Leu Gly Tyr Lys Ala Ile Asn Leu Pro Val Ser Gly Ala Phe
                805                 810                 815

CAC ACT GAA CTT GTT GGT CAC GCT CAA GCG CCA TTT GCT AAA GCG ATT     2496
His Thr Glu Leu Val Gly His Ala Gln Ala Pro Phe Ala Lys Ala Ile
            820                 825                 830

GAC GCA GCC AAA TTT ACT AAA ACA AGC CGA GCA CTT TAC TCA AAT GCA     2544
Asp Ala Ala Lys Phe Thr Lys Thr Ser Arg Ala Leu Tyr Ser Asn Ala
        835                 840                 845

ACT GGC GGA CTT TAT GAA AGC ACT GCT GCA AAG ATT AAA GCC TCG TTT     2592
Thr Gly Gly Leu Tyr Glu Ser Thr Ala Ala Lys Ile Lys Ala Ser Phe
    850                 855                 860

AAG AAA CAT ATG CTT CAA TCA GTG CGC TTT ACT AGC CAG CTA GAA GCC     2640
Lys Lys His Met Leu Gln Ser Val Arg Phe Thr Ser Gln Leu Glu Ala
865                 870                 875                 880

ATG TAC AAC GAC GGC GCC CGT GTA TTT GTT GAA TTT GGT CCA AAG AAC     2688
Met Tyr Asn Asp Gly Ala Arg Val Phe Val Glu Phe Gly Pro Lys Asn
                885                 890                 895

ATC TTA CAA AAA TTA GTT CAA GGC ACG CTT GTC AAC ACT GAA AAT GAA     2736
Ile Leu Gln Lys Leu Val Gln Gly Thr Leu Val Asn Thr Glu Asn Glu
            900                 905                 910

GTT TGC ACT ATC TCT ATC AAC CCT AAT CCT AAA GTT GAT AGT GAT CTG     2784
Val Cys Thr Ile Ser Ile Asn Pro Asn Pro Lys Val Asp Ser Asp Leu
        915                 920                 925

CAG CTT AAG CAA GCA GCA ATG CAG CTA GCG GTT ACT GGT GTG GTA CTC     2832
Gln Leu Lys Gln Ala Ala Met Gln Leu Ala Val Thr Gly Val Val Leu
    930                 935                 940

AGT GAA ATT GAC CCA TAC CAA GCC GAT ATT GCC GCA CCA GCG AAA AAG     2880
Ser Glu Ile Asp Pro Tyr Gln Ala Asp Ile Ala Ala Pro Ala Lys Lys
945                 950                 955                 960

TCG CCA ATG AGC ATT TCG CTT AAT GCT GCT AAC CAT ATC AGC AAA GCA     2928
Ser Pro Met Ser Ile Ser Leu Asn Ala Ala Asn His Ile Ser Lys Ala
                965                 970                 975

ACT CGC GCT AAG ATG GCC AAG TCT TTA GAG ACA GGT ATC GTC ACC TCG     2976
Thr Arg Ala Lys Met Ala Lys Ser Leu Glu Thr Gly Ile Val Thr Ser
            980                 985                 990

CAA ATA GAA CAT GTT ATT GAA GAA AAA ATC GTT GAA GTT GAG AAA CTG     3024
```

-continued

Gln Ile Glu His Val Ile Glu Glu Lys Ile Val Glu Val Glu Lys Leu
995 1000 1005

GTT GAA GTC GAA AAG ATC GTC GAA AAA GTG GTT GAA GTA GAG AAA GTT 3072
Val Glu Val Glu Lys Ile Val Glu Lys Val Val Glu Val Glu Lys Val
1010 1015 1020

GTT GAG GTT GAA GCT CCT GTT AAT TCA GTG CAA GCC AAT GCA ATT CAA 3120
Val Glu Val Glu Ala Pro Val Asn Ser Val Gln Ala Asn Ala Ile Gln
1025 1030 1035 1040

ACC CGT TCA GTT GTC GCT CCA GTA ATA GAG AAC CAA GTC GTG TCT AAA 3168
Thr Arg Ser Val Val Ala Pro Val Ile Glu Asn Gln Val Val Ser Lys
1045 1050 1055

AAC AGT AAG CCA GCA GTC CAG AGC ATT AGT GGT GAT GCA CTC AGC AAC 3216
Asn Ser Lys Pro Ala Val Gln Ser Ile Ser Gly Asp Ala Leu Ser Asn
1060 1065 1070

TTT TTT GCT GCA CAG CAG CAA ACC GCA CAG TTG CAT CAG CAG TTC TTA 3264
Phe Phe Ala Ala Gln Gln Gln Thr Ala Gln Leu His Gln Gln Phe Leu
1075 1080 1085

GCT ATT CCG CAG CAA TAT GGT GAG ACG TTC ACT ACG CTG ATG ACC GAG 3312
Ala Ile Pro Gln Gln Tyr Gly Glu Thr Phe Thr Thr Leu Met Thr Glu
1090 1095 1100

CAA GCT AAA CTG GCA AGT TCT GGT GTT GCA ATT CCA GAG AGT CTG CAA 3360
Gln Ala Lys Leu Ala Ser Ser Gly Val Ala Ile Pro Glu Ser Leu Gln
1105 1110 1115 1120

CGC TCA ATG GAG CAA TTC CAC CAA CTA CAA GCG CAA ACA CTA CAA AGC 3408
Arg Ser Met Glu Gln Phe His Gln Leu Gln Ala Gln Thr Leu Gln Ser
1125 1130 1135

CAC ACC CAG TTC CTT GAG ATG CAA GCG GGT AGC AAC ATT GCA GCG TTA 3456
His Thr Gln Phe Leu Glu Met Gln Ala Gly Ser Asn Ile Ala Ala Leu
1140 1145 1150

AAC CTA CTC AAT AGC AGC CAA GCA ACT TAC GCT CCA GCC ATT CAC AAT 3504
Asn Leu Leu Asn Ser Ser Gln Ala Thr Tyr Ala Pro Ala Ile His Asn
1155 1160 1165

GAA GCG ATT CAA AGC CAA GTG GTT CAA AGC CAA ACT GCA GTC CAG CCA 3552
Glu Ala Ile Gln Ser Gln Val Val Gln Ser Gln Thr Ala Val Gln Pro
1170 1175 1180

GTA ATT TCA ACA CAA GTT AAC CAT GTG TCA GAG CAG CCA ACT CAA GCT 3600
Val Ile Ser Thr Gln Val Asn His Val Ser Glu Gln Pro Thr Gln Ala
1185 1190 1195 1200

CCA GCT CCA AAA GCG CAG CCA GCA CCT GTG ACA ACT GCA GTT CAA ACT 3648
Pro Ala Pro Lys Ala Gln Pro Ala Pro Val Thr Thr Ala Val Gln Thr
1205 1210 1215

GCT CCG GCA CAA GTT GTT CGT CAA GCC GCA CCA GTT CAA GCC GCT ATT 3696
Ala Pro Ala Gln Val Val Arg Gln Ala Ala Pro Val Gln Ala Ala Ile
1220 1225 1230

GAA CCG ATT AAT ACA AGT GTT GCG ACT ACA ACG CCT TCA GCC TTC AGC 3744
Glu Pro Ile Asn Thr Ser Val Ala Thr Thr Thr Pro Ser Ala Phe Ser
1235 1240 1245

GCC GAA ACA GCC CTG AGC GCA ACA AAA GTC CAA GCC ACT ATG CTT GAA 3792
Ala Glu Thr Ala Leu Ser Ala Thr Lys Val Gln Ala Thr Met Leu Glu
1250 1255 1260

GTG GTT GCT GAG AAA ACC GGT TAC CCA ACT GAA ATG CTA GAG CTT GAA 3840
Val Val Ala Glu Lys Thr Gly Tyr Pro Thr Glu Met Leu Glu Leu Glu
1265 1270 1275 1280

ATG GAT ATG GAA GCC GAT TTA GGC ATC GAT TCT ATC AAG CGT GTA GAA 3888
Met Asp Met Glu Ala Asp Leu Gly Ile Asp Ser Ile Lys Arg Val Glu
1285 1290 1295

ATT CTT GGC ACA GTA CAA GAT GAG CTA CCG GGT CTA CCT GAG CTT AGC 3936
Ile Leu Gly Thr Val Gln Asp Glu Leu Pro Gly Leu Pro Glu Leu Ser
1300 1305 1310

CCT GAA GAT CTA GCT GAG TGT CGA ACG CTA GGC GAA ATC GTT GAC TAT 3984

-continued

```
Pro Glu Asp Leu Ala Glu Cys Arg Thr Leu Gly Glu Ile Val Asp Tyr
        1315                1320                1325

ATG GGC AGT AAA CTG CCG GCT GAA GGC TCT ATG AAT TCT CAG CTG TCT      4032
Met Gly Ser Lys Leu Pro Ala Glu Gly Ser Met Asn Ser Gln Leu Ser
    1330                1335                1340

ACA GGT TCC GCA GCT GCG ACT CCT GCA GCG AAT GGT CTT TCT GCG GAG      4080
Thr Gly Ser Ala Ala Ala Thr Pro Ala Ala Asn Gly Leu Ser Ala Glu
1345                1350                1355                1360

AAA GTT CAA GCG ACT ATG ATG TCT GTG GTT GCC GAA AAG ACT GGC TAC      4128
Lys Val Gln Ala Thr Met Met Ser Val Val Ala Glu Lys Thr Gly Tyr
                1365                1370                1375

CCA ACT GAA ATG CTA GAG CTT GAA ATG GAT ATG GAA GCC GAT TTA GGC      4176
Pro Thr Glu Met Leu Glu Leu Glu Met Asp Met Glu Ala Asp Leu Gly
            1380                1385                1390

ATA GAT TCT ATC AAG CGC GTT GAA ATT CTT GGC ACA GTA CAA GAT GAG      4224
Ile Asp Ser Ile Lys Arg Val Glu Ile Leu Gly Thr Val Gln Asp Glu
        1395                1400                1405

CTA CCG GGT CTA CCT GAG CTT AGC CCT GAA GAT CTA GCT GAG TGT CGT      4272
Leu Pro Gly Leu Pro Glu Leu Ser Pro Glu Asp Leu Ala Glu Cys Arg
    1410                1415                1420

ACT CTA GGC GAA ATC GTT GAC TAT ATG AAC TCT AAA CTC GCT GAC GGC      4320
Thr Leu Gly Glu Ile Val Asp Tyr Met Asn Ser Lys Leu Ala Asp Gly
1425                1430                1435                1440

TCT AAG CTG CCG GCT GAA GGC TCT ATG AAT TCT CAG CTG TCT ACA AGT      4368
Ser Lys Leu Pro Ala Glu Gly Ser Met Asn Ser Gln Leu Ser Thr Ser
                1445                1450                1455

GCC GCA GCT GCG ACT CCT GCA GCG AAT GGT CTC TCT GCG GAG AAA GTT      4416
Ala Ala Ala Ala Thr Pro Ala Ala Asn Gly Leu Ser Ala Glu Lys Val
            1460                1465                1470

CAA GCG ACT ATG ATG TCT GTG GTT GCC GAA AAG ACT GGC TAC CCA ACT      4464
Gln Ala Thr Met Met Ser Val Val Ala Glu Lys Thr Gly Tyr Pro Thr
        1475                1480                1485

GAA ATG CTA GAA CTT GAA ATG GAT ATG GAA GCT GAC CTT GGC ATC GAT      4512
Glu Met Leu Glu Leu Glu Met Asp Met Glu Ala Asp Leu Gly Ile Asp
    1490                1495                1500

TCA ATC AAG CGC GTT GAA ATT CTT GGC ACA GTA CAA GAT GAG CTA CCG      4560
Ser Ile Lys Arg Val Glu Ile Leu Gly Thr Val Gln Asp Glu Leu Pro
1505                1510                1515                1520

GGT TTA CCT GAG CTA AAT CCA GAA GAT TTG GCA GAG TGT CGT ACT CTT      4608
Gly Leu Pro Glu Leu Asn Pro Glu Asp Leu Ala Glu Cys Arg Thr Leu
                1525                1530                1535

GGC GAA ATC GTG ACT TAT ATG AAC TCT AAA CTC GCT GAC GGC TCT AAG      4656
Gly Glu Ile Val Thr Tyr Met Asn Ser Lys Leu Ala Asp Gly Ser Lys
            1540                1545                1550

CTG CCA GCT GAA GGC TCT ATG CAC TAT CAG CTG TCT ACA AGT ACC GCT      4704
Leu Pro Ala Glu Gly Ser Met His Tyr Gln Leu Ser Thr Ser Thr Ala
        1555                1560                1565

GCT GCG ACT CCT GTA GCG AAT GGT CTC TCT GCA GAA AAA GTT CAA GCG      4752
Ala Ala Thr Pro Val Ala Asn Gly Leu Ser Ala Glu Lys Val Gln Ala
    1570                1575                1580

ACC ATG ATG TCT GTA GTT GCA GAT AAA ACT GGC TAC CCA ACT GAA ATG      4800
Thr Met Met Ser Val Val Ala Asp Lys Thr Gly Tyr Pro Thr Glu Met
1585                1590                1595                1600

CTT GAA CTT GAA ATG GAT ATG GAA GCC GAT TTA GGT ATC GAT TCT ATC      4848
Leu Glu Leu Glu Met Asp Met Glu Ala Asp Leu Gly Ile Asp Ser Ile
                1605                1610                1615

AAG CGC GTT GAA ATT CTT GGC ACA GTA CAA GAT GAG CTA CCG GGT TTA      4896
Lys Arg Val Glu Ile Leu Gly Thr Val Gln Asp Glu Leu Pro Gly Leu
            1620                1625                1630

CCT GAG CTA AAT CCA GAA GAT CTA GCA GAG TGT CGC ACC CTA GGC GAA      4944
```

-continued

```
Pro Glu Leu Asn Pro Glu Asp Leu Ala Glu Cys Arg Thr Leu Gly Glu
        1635                1640                1645

ATC GTT GAC TAT ATG GGC AGT AAA CTG CCG GCT GAA GGC TCT GCT AAT    4992
Ile Val Asp Tyr Met Gly Ser Lys Leu Pro Ala Glu Gly Ser Ala Asn
    1650                1655                1660

ACA AGT GCC GCT GCG TCT CTT AAT GTT AGT GCC GTT GCG GCG CCT CAA    5040
Thr Ser Ala Ala Ala Ser Leu Asn Val Ser Ala Val Ala Ala Pro Gln
1665                1670                1675                1680

GCT GCT GCG ACT CCT GTA TCG AAC GGT CTC TCT GCA GAG AAA GTG CAA    5088
Ala Ala Ala Thr Pro Val Ser Asn Gly Leu Ser Ala Glu Lys Val Gln
                1685                1690                1695

AGC ACT ATG ATG TCA GTA GTT GCA GAA AAG ACC GGC TAC CCA ACT GAA    5136
Ser Thr Met Met Ser Val Val Ala Glu Lys Thr Gly Tyr Pro Thr Glu
            1700                1705                1710

ATG CTA GAA CTT GGC ATG GAT ATG GAA GCC GAT TTA GGT ATC GAC TCA    5184
Met Leu Glu Leu Gly Met Asp Met Glu Ala Asp Leu Gly Ile Asp Ser
        1715                1720                1725

ATT AAA CGC GTT GAG ATT CTT GGC ACA GTA CAA GAT GAG CTA CCG GGT    5232
Ile Lys Arg Val Glu Ile Leu Gly Thr Val Gln Asp Glu Leu Pro Gly
    1730                1735                1740

CTA CCA GAG CTT AAT CCT GAA GAT TTA GCT GAG TGC CGT ACG CTG GGC    5280
Leu Pro Glu Leu Asn Pro Glu Asp Leu Ala Glu Cys Arg Thr Leu Gly
1745                1750                1755                1760

GAA ATC GTT GAC TAT ATG AAC TCT AAG CTG GCT GAC GGC TCT AAG CTT    5328
Glu Ile Val Asp Tyr Met Asn Ser Lys Leu Ala Asp Gly Ser Lys Leu
                1765                1770                1775

CCA GCT GAA GGC TCT GCT AAT ACA AGT GCC ACT GCT GCG ACT CCT GCA    5376
Pro Ala Glu Gly Ser Ala Asn Thr Ser Ala Thr Ala Ala Thr Pro Ala
            1780                1785                1790

GTG AAT GGT CTT TCT GCT GAC AAG GTA CAG GCG ACT ATG ATG TCT GTA    5424
Val Asn Gly Leu Ser Ala Asp Lys Val Gln Ala Thr Met Met Ser Val
        1795                1800                1805

GTT GCT GAA AAG ACC GGC TAC CCA ACT GAA ATG CTA GAA CTT GGC ATG    5472
Val Ala Glu Lys Thr Gly Tyr Pro Thr Glu Met Leu Glu Leu Gly Met
    1810                1815                1820

GAT ATG GAA GCA GAC CTT GGT ATT GAT TCT ATT AAG CGC GTT GAA ATT    5520
Asp Met Glu Ala Asp Leu Gly Ile Asp Ser Ile Lys Arg Val Glu Ile
1825                1830                1835                1840

CTT GGC ACA GTA CAA GAT GAG CTC CCA GGT TTA CCT GAG CTT AAT CCT    5568
Leu Gly Thr Val Gln Asp Glu Leu Pro Gly Leu Pro Glu Leu Asn Pro
                1845                1850                1855

GAA GAT CTC GCT GAG TGC CGC ACG CTT GGC GAA ATC GTT AGC TAT ATG    5616
Glu Asp Leu Ala Glu Cys Arg Thr Leu Gly Glu Ile Val Ser Tyr Met
            1860                1865                1870

AAC TCT CAA CTG GCT GAT GGC TCT AAA CTT TCT ACA AGT GCG GCT GAA    5664
Asn Ser Gln Leu Ala Asp Gly Ser Lys Leu Ser Thr Ser Ala Ala Glu
        1875                1880                1885

GGC TCT GCT GAT ACA AGT GCT GCA AAT GCT GCA AAG CCG GCA GCA ATT    5712
Gly Ser Ala Asp Thr Ser Ala Ala Asn Ala Ala Lys Pro Ala Ala Ile
    1890                1895                1900

TCG GCA GAA CCA AGT GTT GAG CTT CCT CCT CAT AGC GAG GTA GCG CTA    5760
Ser Ala Glu Pro Ser Val Glu Leu Pro Pro His Ser Glu Val Ala Leu
1905                1910                1915                1920

AAA AAG CTT AAT GCG GCG AAC AAG CTA GAA AAT TGT TTC GCC GCA GAC    5808
Lys Lys Leu Asn Ala Ala Asn Lys Leu Glu Asn Cys Phe Ala Ala Asp
                1925                1930                1935

GCA AGT GTT GTG ATT AAC GAT GAT GGT CAC AAC GCA GGC GTT TTA GCT    5856
Ala Ser Val Val Ile Asn Asp Asp Gly His Asn Ala Gly Val Leu Ala
            1940                1945                1950

GAG AAA CTT ATT AAA CAA GGC CTA AAA GTA GCC GTT GTG CGT TTA CCG    5904
```

-continued

```
Glu Lys Leu Ile Lys Gln Gly Leu Lys Val Ala Val Val Arg Leu Pro
        1955                1960                1965

AAA GGT CAG CCT CAA TCG CCA CTT TCA AGC GAT GTT GCT AGC TTT GAG      5952
Lys Gly Gln Pro Gln Ser Pro Leu Ser Ser Asp Val Ala Ser Phe Glu
    1970                1975                1980

CTT GCC TCA AGC CAA GAA TCT GAG CTT GAA GCC AGT ATC ACT GCA GTT      6000
Leu Ala Ser Ser Gln Glu Ser Glu Leu Glu Ala Ser Ile Thr Ala Val
1985                1990                1995                2000

ATC GCG CAG ATT GAA ACT CAG GTT GGC GCT ATT GGT GGC TTT ATT CAC      6048
Ile Ala Gln Ile Glu Thr Gln Val Gly Ala Ile Gly Gly Phe Ile His
                2005                2010                2015

TTG CAA CCA GAA GCG AAT ACA GAA GAG CAA ACG GCA GTA AAC CTA GAT      6096
Leu Gln Pro Glu Ala Asn Thr Glu Glu Gln Thr Ala Val Asn Leu Asp
            2020                2025                2030

GCG CAA AGT TTT ACT CAC GTT AGC AAT GCG TTC TTG TGG GCC AAA TTA      6144
Ala Gln Ser Phe Thr His Val Ser Asn Ala Phe Leu Trp Ala Lys Leu
        2035                2040                2045

TTG CAA CCA AAG CTC GTT GCT GGA GCA GAT GCG CGT CGC TGT TTT GTA      6192
Leu Gln Pro Lys Leu Val Ala Gly Ala Asp Ala Arg Arg Cys Phe Val
    2050                2055                2060

ACA GTA AGC CGT ATC GAC GGT GGC TTT GGT TAC CTA AAT ACT GAC GCC      6240
Thr Val Ser Arg Ile Asp Gly Gly Phe Gly Tyr Leu Asn Thr Asp Ala
2065                2070                2075                2080

CTA AAA GAT GCT GAG CTA AAC CAA GCA GCA TTA GCT GGT TTA ACT AAA      6288
Leu Lys Asp Ala Glu Leu Asn Gln Ala Ala Leu Ala Gly Leu Thr Lys
                2085                2090                2095

ACC TTA AGC CAT GAA TGG CCA CAA GTG TTC TGT CGC GCG CTA GAT ATT      6336
Thr Leu Ser His Glu Trp Pro Gln Val Phe Cys Arg Ala Leu Asp Ile
            2100                2105                2110

GCA ACA GAT GTT GAT GCA ACC CAT CTT GCT GAT GCA ATC ACC AGT GAA      6384
Ala Thr Asp Val Asp Ala Thr His Leu Ala Asp Ala Ile Thr Ser Glu
        2115                2120                2125

CTA TTT GAT AGC CAA GCT CAG CTA CCT GAA GTG GGC TTA AGC TTA ATT      6432
Leu Phe Asp Ser Gln Ala Gln Leu Pro Glu Val Gly Leu Ser Leu Ile
    2130                2135                2140

GAT GGC AAA GTT AAC CGC GTA ACT CTA GTT GCT GCT GAA GCT GCA GAT      6480
Asp Gly Lys Val Asn Arg Val Thr Leu Val Ala Ala Glu Ala Ala Asp
2145                2150                2155                2160

AAA ACA GCA AAA GCA GAG CTT AAC AGC ACA GAT AAA ATC TTA GTG ACT      6528
Lys Thr Ala Lys Ala Glu Leu Asn Ser Thr Asp Lys Ile Leu Val Thr
                2165                2170                2175

GGT GGG GCA AAA GGG GTG ACA TTT GAA TGT GCA CTG GCA TTA GCA TCT      6576
Gly Gly Ala Lys Gly Val Thr Phe Glu Cys Ala Leu Ala Leu Ala Ser
            2180                2185                2190

CGC AGC CAG TCT CAC TTT ATC TTA GCT GGG CGC AGT GAA TTA CAA GCT      6624
Arg Ser Gln Ser His Phe Ile Leu Ala Gly Arg Ser Glu Leu Gln Ala
        2195                2200                2205

TTA CCA AGC TGG GCT GAG GGT AAG CAA ACT AGC GAG CTA AAA TCA GCT      6672
Leu Pro Ser Trp Ala Glu Gly Lys Gln Thr Ser Glu Leu Lys Ser Ala
    2210                2215                2220

GCA ATC GCA CAT ATT ATT TCT ACT GGT CAA AAG CCA ACG CCT AAG CAA      6720
Ala Ile Ala His Ile Ile Ser Thr Gly Gln Lys Pro Thr Pro Lys Gln
2225                2230                2235                2240

GTT GAA GCC GCT GTG TGG CCA GTG CAA AGC AGC ATT GAA ATT AAT GCC      6768
Val Glu Ala Ala Val Trp Pro Val Gln Ser Ser Ile Glu Ile Asn Ala
                2245                2250                2255

GCC CTA GCC GCC TTT AAC AAA GTT GGC GCC TCA GCT GAA TAC GTC AGC      6816
Ala Leu Ala Ala Phe Asn Lys Val Gly Ala Ser Ala Glu Tyr Val Ser
            2260                2265                2270

ATG GAT GTT ACC GAT AGC GCC GCA ATC ACA GCA GCA CTT AAT GGT CGC      6864
```

-continued

```
Met Asp Val Thr Asp Ser Ala Ala Ile Thr Ala Ala Leu Asn Gly Arg
        2275                2280                2285

TCA AAT GAG ATC ACC GGT CTT ATT CAT GGC GCA GGT GTA CTA GCC GAC     6912
Ser Asn Glu Ile Thr Gly Leu Ile His Gly Ala Gly Val Leu Ala Asp
    2290                2295                2300

AAG CAT ATT CAA GAC AAG ACT CTT GCT GAA CTT GCT AAA GTT TAT GGC     6960
Lys His Ile Gln Asp Lys Thr Leu Ala Glu Leu Ala Lys Val Tyr Gly
2305                2310                2315                2320

ACT AAA GTC AAC GGC CTA AAA GCG CTG CTC GCG GCA CTT GAG CCA AGC     7008
Thr Lys Val Asn Gly Leu Lys Ala Leu Leu Ala Ala Leu Glu Pro Ser
                2325                2330                2335

AAA ATT AAA TTA CTT GCT ATG TTC TCA TCT GCA GCA GGT TTT TAC GGT     7056
Lys Ile Lys Leu Leu Ala Met Phe Ser Ser Ala Ala Gly Phe Tyr Gly
            2340                2345                2350

AAT ATC GGC CAA AGC GAT TAC GCG ATG TCG AAC GAT ATT CTT AAC AAG     7104
Asn Ile Gly Gln Ser Asp Tyr Ala Met Ser Asn Asp Ile Leu Asn Lys
        2355                2360                2365

GCA GCG CTG CAG TTC ACC GCT CGC AAC CCA CAA GCT AAA GTC ATG AGC     7152
Ala Ala Leu Gln Phe Thr Ala Arg Asn Pro Gln Ala Lys Val Met Ser
    2370                2375                2380

TTT AAC TGG GGT CCT TGG GAT GGC GGC ATG GTT AAC CCA GCG CTT AAA     7200
Phe Asn Trp Gly Pro Trp Asp Gly Gly Met Val Asn Pro Ala Leu Lys
2385                2390                2395                2400

AAG ATG TTT ACC GAG CGT GGT GTG TAC GTT ATT CCA CTA AAA GCA GGT     7248
Lys Met Phe Thr Glu Arg Gly Val Tyr Val Ile Pro Leu Lys Ala Gly
                2405                2410                2415

GCA GAG CTA TTT GCC ACT CAG CTA TTG GCT GAA ACT GGC GTG CAG TTG     7296
Ala Glu Leu Phe Ala Thr Gln Leu Leu Ala Glu Thr Gly Val Gln Leu
            2420                2425                2430

CTC ATT GGT ACG TCA ATG CAA GGT GGC AGC GAC ACT AAA GCA ACT GAG     7344
Leu Ile Gly Thr Ser Met Gln Gly Gly Ser Asp Thr Lys Ala Thr Glu
        2435                2440                2445

ACT GCT TCT GTA AAA AAG CTT AAT GCG GGT GAG GTG CTA AGT GCA TCG     7392
Thr Ala Ser Val Lys Lys Leu Asn Ala Gly Glu Val Leu Ser Ala Ser
    2450                2455                2460

CAT CCG CGT GCT GGT GCA CAA AAA ACA CCA CTA CAA GCT GTC ACT GCA     7440
His Pro Arg Ala Gly Ala Gln Lys Thr Pro Leu Gln Ala Val Thr Ala
2465                2470                2475                2480

ACG CGT CTG TTA ACC CCA AGT GCC ATG GTC TTC ATT GAA GAT CAC CGC     7488
Thr Arg Leu Leu Thr Pro Ser Ala Met Val Phe Ile Glu Asp His Arg
                2485                2490                2495

ATT GGC GGT AAC AGT GTG TTG CCA ACG GTA TGC GCC ATC GAC TGG ATG     7536
Ile Gly Gly Asn Ser Val Leu Pro Thr Val Cys Ala Ile Asp Trp Met
            2500                2505                2510

CGT GAA GCG GCA AGC GAC ATG CTT GGC GCT CAA GTT AAG GTA CTT GAT     7584
Arg Glu Ala Ala Ser Asp Met Leu Gly Ala Gln Val Lys Val Leu Asp
        2515                2520                2525

TAC AAG CTA TTA AAA GGC ATT GTA TTT GAG ACT GAT GAG CCG CAA GAG     7632
Tyr Lys Leu Leu Lys Gly Ile Val Phe Glu Thr Asp Glu Pro Gln Glu
    2530                2535                2540

TTA ACA CTT GAG CTA ACG CCA GAC GAT TCA GAC GAA GCT ACG CTA CAA     7680
Leu Thr Leu Glu Leu Thr Pro Asp Asp Ser Asp Glu Ala Thr Leu Gln
2545                2550                2555                2560

GCA TTA ATC AGC TGT AAT GGG CGT CCG CAA TAC AAG GCG ACG CTT ATC     7728
Ala Leu Ile Ser Cys Asn Gly Arg Pro Gln Tyr Lys Ala Thr Leu Ile
                2565                2570                2575

AGT GAT AAT GCC GAT ATT AAG CAA CTT AAC AAG CAG TTT GAT TTA AGC     7776
Ser Asp Asn Ala Asp Ile Lys Gln Leu Asn Lys Gln Phe Asp Leu Ser
            2580                2585                2590

GCT AAG GCG ATT ACC ACA GCA AAA GAG CTT TAT AGC AAC GGC ACC TTG     7824
```

-continued

Ala Lys Ala Ile Thr Thr Ala Lys Glu Leu Tyr Ser Asn Gly Thr Leu
2595 2600 2605

TTC CAC GGT CCG CGT CTA CAA GGG ATC CAA TCT GTA GTG CAG TTC GAT 7872
Phe His Gly Pro Arg Leu Gln Gly Ile Gln Ser Val Val Gln Phe Asp
2610 2615 2620

GAT CAA GGC TTA ATT GCT AAA GTC GCT CTG CCT AAG GTT GAA CTT AGC 7920
Asp Gln Gly Leu Ile Ala Lys Val Ala Leu Pro Lys Val Glu Leu Ser
2625 2630 2635 2640

GAT TGT GGT GAG TTC TTG CCG CAA ACC CAC ATG GGT GGC AGT CAA CCT 7968
Asp Cys Gly Glu Phe Leu Pro Gln Thr His Met Gly Gly Ser Gln Pro
2645 2650 2655

TTT GCT GAG GAC TTG CTA TTA CAA GCT ATG CTG GTT TGG GCT CGC CTT 8016
Phe Ala Glu Asp Leu Leu Leu Gln Ala Met Leu Val Trp Ala Arg Leu
2660 2665 2670

AAA ACT GGC TCG GCA AGT TTG CCA TCA AGC ATT GGT GAG TTT ACC TCA 8064
Lys Thr Gly Ser Ala Ser Leu Pro Ser Ser Ile Gly Glu Phe Thr Ser
2675 2680 2685

TAC CAA CCA ATG GCC TTT GGT GAA ACT GGT ACC ATA GAG CTT GAA GTG 8112
Tyr Gln Pro Met Ala Phe Gly Glu Thr Gly Thr Ile Glu Leu Glu Val
2690 2695 2700

ATT AAG CAC AAC AAA CGC TCA CTT GAA GCG AAT GTT GCG CTA TAT CGT 8160
Ile Lys His Asn Lys Arg Ser Leu Glu Ala Asn Val Ala Leu Tyr Arg
2705 2710 2715 2720

GAC AAC GGC GAG TTA AGT GCC ATG TTT AAG TCA GCT AAA ATC ACC ATT 8208
Asp Asn Gly Glu Leu Ser Ala Met Phe Lys Ser Ala Lys Ile Thr Ile
2725 2730 2735

AGC AAA AGC TTA AAT TCA GCA TTT TTA CCT GCT GTC TTA GCA AAC GAC 8256
Ser Lys Ser Leu Asn Ser Ala Phe Leu Pro Ala Val Leu Ala Asn Asp
2740 2745 2750

AGT GAG GCG AAT 8268
Ser Glu Ala Asn
2755

( 2 ) INFORMATION FOR SEQ ID NO:11:

( i ) SEQUENCE CHARACTERISTICS:
( A ) LENGTH: 2756 amino acids
( B ) TYPE: amino acid
( D ) TOPOLOGY: linear ( i i ) MOLECULE TYPE: protein ( x i ) SEQUENCE DESCRIPTION: SEQ ID NO:11:

Met Ser Gln Thr Ser Lys Pro Thr Asn Ser Ala Thr Glu Gln Ala Gln
1 5 10 15

Asp Ser Gln Ala Asp Ser Arg Leu Asn Lys Arg Leu Lys Asp Met Pro
20 25 30

Ile Ala Ile Val Gly Met Ala Ser Ile Phe Ala Asn Ser Arg Tyr Leu
35 40 45

Asn Lys Phe Trp Asp Leu Ile Ser Glu Lys Ile Asp Ala Ile Thr Glu
50 55 60

Leu Pro Ser Thr His Trp Gln Pro Glu Glu Tyr Tyr Asp Ala Asp Lys
65 70 75 80

Thr Ala Ala Asp Lys Ser Tyr Cys Lys Arg Gly Gly Phe Leu Pro Asp
85 90 95

Val Asp Phe Asn Pro Met Glu Phe Gly Leu Pro Pro Asn Ile Leu Glu
100 105 110

Leu Thr Asp Ser Ser Gln Leu Leu Ser Leu Ile Val Ala Lys Glu Val
115 120 125

Leu Ala Asp Ala Asn Leu Pro Glu Asn Tyr Asp Arg Asp Lys Ile Gly

-continued

```
        130                        135                        140

Ile Thr Leu Gly Val Gly Gly Gly Gln Lys Ile Ser His Ser Leu Thr
145                 150                 155                 160

Ala Arg Leu Gln Tyr Pro Val Leu Lys Lys Val Phe Ala Asn Ser Gly
                165                 170                 175

Ile Ser Asp Thr Asp Ser Glu Met Leu Ile Lys Lys Phe Gln Asp Gln
            180                 185                 190

Tyr Val His Trp Glu Glu Asn Ser Phe Pro Gly Ser Leu Gly Asn Val
        195                 200                 205

Ile Ala Gly Arg Ile Ala Asn Arg Phe Asp Phe Gly Gly Met Asn Cys
    210                 215                 220

Val Val Asp Ala Ala Cys Ala Gly Ser Leu Ala Ala Met Arg Met Ala
225                 230                 235                 240

Leu Thr Glu Leu Thr Glu Gly Arg Ser Glu Met Met Ile Thr Gly Gly
                245                 250                 255

Val Cys Thr Asp Asn Ser Pro Ser Met Tyr Met Ser Phe Ser Lys Thr
            260                 265                 270

Pro Ala Phe Thr Thr Asn Glu Thr Ile Gln Pro Phe Asp Ile Asp Ser
        275                 280                 285

Lys Gly Met Met Ile Gly Glu Gly Ile Gly Met Val Ala Leu Lys Arg
    290                 295                 300

Leu Glu Asp Ala Glu Arg Asp Gly Asp Arg Ile Tyr Ser Val Ile Lys
305                 310                 315                 320

Gly Val Gly Ala Ser Ser Asp Gly Lys Phe Lys Ser Ile Tyr Ala Pro
                325                 330                 335

Arg Pro Ser Gly Gln Ala Lys Ala Leu Asn Arg Ala Tyr Asp Asp Ala
            340                 345                 350

Gly Phe Ala Pro His Thr Leu Gly Leu Ile Glu Ala His Gly Thr Gly
        355                 360                 365

Thr Ala Ala Gly Asp Ala Ala Glu Phe Ala Gly Leu Cys Ser Val Phe
    370                 375                 380

Ala Glu Gly Asn Asp Thr Lys Gln His Ile Ala Leu Gly Ser Val Lys
385                 390                 395                 400

Ser Gln Ile Gly His Thr Lys Ser Thr Ala Gly Thr Ala Gly Leu Ile
                405                 410                 415

Lys Ala Ala Leu Ala Leu His His Lys Val Leu Pro Pro Thr Ile Asn
            420                 425                 430

Val Ser Gln Pro Ser Pro Lys Leu Asp Ile Glu Asn Ser Pro Phe Tyr
        435                 440                 445

Leu Asn Thr Glu Thr Arg Pro Trp Leu Pro Arg Val Asp Gly Thr Pro
    450                 455                 460

Arg Arg Ala Gly Ile Ser Ser Phe Gly Phe Gly Gly Thr Asn Phe His
465                 470                 475                 480

Phe Val Leu Glu Glu Tyr Asn Gln Glu His Ser Arg Thr Asp Ser Glu
                485                 490                 495

Lys Ala Lys Tyr Arg Gln Arg Gln Val Ala Gln Ser Phe Leu Val Ser
            500                 505                 510

Ala Ser Asp Lys Ala Ser Leu Ile Asn Glu Leu Asn Val Leu Ala Ala
        515                 520                 525

Ser Ala Ser Gln Ala Glu Phe Ile Leu Lys Asp Ala Ala Ala Asn Tyr
    530                 535                 540

Gly Val Arg Glu Leu Asp Lys Asn Ala Pro Arg Ile Gly Leu Val Ala
545                 550                 555                 560
```

-continued

Asn Thr Ala Glu Glu Leu Ala Gly Leu Ile Lys Gln Ala Leu Ala Lys
565 570 575

Leu Ala Ala Ser Asp Asp Asn Ala Trp Gln Leu Pro Gly Gly Thr Ser
580 585 590

Tyr Arg Ala Ala Ala Val Glu Gly Lys Val Ala Ala Leu Phe Ala Gly
595 600 605

Gln Gly Ser Gln Tyr Leu Asn Met Gly Arg Asp Leu Thr Cys Tyr Tyr
610 615 620

Pro Glu Met Arg Gln Gln Phe Val Thr Ala Asp Lys Val Phe Ala Ala
625 630 635 640

Asn Asp Lys Thr Pro Leu Ser Gln Thr Leu Tyr Pro Lys Pro Val Phe
645 650 655

Asn Lys Asp Glu Leu Lys Ala Gln Glu Ala Ile Leu Thr Asn Thr Ala
660 665 670

Asn Ala Gln Ser Ala Ile Gly Ala Ile Ser Met Gly Gln Tyr Asp Leu
675 680 685

Phe Thr Ala Ala Gly Phe Asn Ala Asp Met Val Ala Gly His Ser Phe
690 695 700

Gly Glu Leu Ser Ala Leu Cys Ala Ala Gly Val Ile Ser Ala Asp Asp
705 710 715 720

Tyr Tyr Lys Leu Ala Phe Ala Arg Gly Glu Ala Met Ala Thr Lys Ala
725 730 735

Pro Ala Lys Asp Gly Val Glu Ala Asp Ala Gly Ala Met Phe Ala Ile
740 745 750

Ile Thr Lys Ser Ala Ala Asp Leu Glu Thr Val Glu Ala Thr Ile Ala
755 760 765

Lys Phe Asp Gly Val Lys Val Ala Asn Tyr Asn Ala Pro Thr Gln Ser
770 775 780

Val Ile Ala Gly Pro Thr Ala Thr Thr Ala Asp Ala Ala Lys Ala Leu
785 790 795 800

Thr Glu Leu Gly Tyr Lys Ala Ile Asn Leu Pro Val Ser Gly Ala Phe
805 810 815

His Thr Glu Leu Val Gly His Ala Gln Ala Pro Phe Ala Lys Ala Ile
820 825 830

Asp Ala Ala Lys Phe Thr Lys Thr Ser Arg Ala Leu Tyr Ser Asn Ala
835 840 845

Thr Gly Gly Leu Tyr Glu Ser Thr Ala Ala Lys Ile Lys Ala Ser Phe
850 855 860

Lys Lys His Met Leu Gln Ser Val Arg Phe Thr Ser Gln Leu Glu Ala
865 870 875 880

Met Tyr Asn Asp Gly Ala Arg Val Phe Val Glu Phe Gly Pro Lys Asn
885 890 895

Ile Leu Gln Lys Leu Val Gln Gly Thr Leu Val Asn Thr Glu Asn Glu
900 905 910

Val Cys Thr Ile Ser Ile Asn Pro Asn Pro Lys Val Asp Ser Asp Leu
915 920 925

Gln Leu Lys Gln Ala Ala Met Gln Leu Ala Val Thr Gly Val Val Leu
930 935 940

Ser Glu Ile Asp Pro Tyr Gln Ala Asp Ile Ala Ala Pro Ala Lys Lys
945 950 955 960

Ser Pro Met Ser Ile Ser Leu Asn Ala Ala Asn His Ile Ser Lys Ala
965 970 975

Thr Arg Ala Lys Met Ala Lys Ser Leu Glu Thr Gly Ile Val Thr Ser
980 985 990

-continued

Gln Ile Glu His Val Ile Glu Glu Lys Ile Val Glu Val Glu Lys Leu
995 1000 1005

Val Glu Val Glu Lys Ile Val Glu Lys Val Val Glu Val Glu Lys Val
1010 1015 1020

Val Glu Val Glu Ala Pro Val Asn Ser Val Gln Ala Asn Ala Ile Gln
1025 1030 1035 1040

Thr Arg Ser Val Val Ala Pro Val Ile Glu Asn Gln Val Val Ser Lys
1045 1050 1055

Asn Ser Lys Pro Ala Val Gln Ser Ile Ser Gly Asp Ala Leu Ser Asn
1060 1065 1070

Phe Phe Ala Ala Gln Gln Gln Thr Ala Gln Leu His Gln Gln Phe Leu
1075 1080 1085

Ala Ile Pro Gln Gln Tyr Gly Glu Thr Phe Thr Thr Leu Met Thr Glu
1090 1095 1100

Gln Ala Lys Leu Ala Ser Ser Gly Val Ala Ile Pro Glu Ser Leu Gln
1105 1110 1115 1120

Arg Ser Met Glu Gln Phe His Gln Leu Gln Ala Gln Thr Leu Gln Ser
1125 1130 1135

His Thr Gln Phe Leu Glu Met Gln Ala Gly Ser Asn Ile Ala Ala Leu
1140 1145 1150

Asn Leu Leu Asn Ser Ser Gln Ala Thr Tyr Ala Pro Ala Ile His Asn
1155 1160 1165

Glu Ala Ile Gln Ser Gln Val Val Gln Ser Gln Thr Ala Val Gln Pro
1170 1175 1180

Val Ile Ser Thr Gln Val Asn His Val Ser Glu Gln Pro Thr Gln Ala
1185 1190 1195 1200

Pro Ala Pro Lys Ala Gln Pro Ala Pro Val Thr Thr Ala Val Gln Thr
1205 1210 1215

Ala Pro Ala Gln Val Val Arg Gln Ala Ala Pro Val Gln Ala Ala Ile
1220 1225 1230

Glu Pro Ile Asn Thr Ser Val Ala Thr Thr Thr Pro Ser Ala Phe Ser
1235 1240 1245

Ala Glu Thr Ala Leu Ser Ala Thr Lys Val Gln Ala Thr Met Leu Glu
1250 1255 1260

Val Val Ala Glu Lys Thr Gly Tyr Pro Thr Glu Met Leu Glu Leu Glu
1265 1270 1275 1280

Met Asp Met Glu Ala Asp Leu Gly Ile Asp Ser Ile Lys Arg Val Glu
1285 1290 1295

Ile Leu Gly Thr Val Gln Asp Glu Leu Pro Gly Leu Pro Glu Leu Ser
1300 1305 1310

Pro Glu Asp Leu Ala Glu Cys Arg Thr Leu Gly Glu Ile Val Asp Tyr
1315 1320 1325

Met Gly Ser Lys Leu Pro Ala Glu Gly Ser Met Asn Ser Gln Leu Ser
1330 1335 1340

Thr Gly Ser Ala Ala Ala Thr Pro Ala Ala Asn Gly Leu Ser Ala Glu
1345 1350 1355 1360

Lys Val Gln Ala Thr Met Met Ser Val Val Ala Glu Lys Thr Gly Tyr
1365 1370 1375

Pro Thr Glu Met Leu Glu Leu Glu Met Asp Met Glu Ala Asp Leu Gly
1380 1385 1390

Ile Asp Ser Ile Lys Arg Val Glu Ile Leu Gly Thr Val Gln Asp Glu
1395 1400 1405

Leu Pro Gly Leu Pro Glu Leu Ser Pro Glu Asp Leu Ala Glu Cys Arg

```
    1410                    1415                    1420

Thr Leu Gly Glu Ile Val Asp Tyr Met Asn Ser Lys Leu Ala Asp Gly
1425                1430                1435                1440

Ser Lys Leu Pro Ala Glu Gly Ser Met Asn Ser Gln Leu Ser Thr Ser
                1445                1450                1455

Ala Ala Ala Ala Thr Pro Ala Ala Asn Gly Leu Ser Ala Glu Lys Val
            1460                1465                1470

Gln Ala Thr Met Met Ser Val Val Ala Glu Lys Thr Gly Tyr Pro Thr
        1475                1480                1485

Glu Met Leu Glu Leu Glu Met Asp Met Glu Ala Asp Leu Gly Ile Asp
    1490                1495                1500

Ser Ile Lys Arg Val Glu Ile Leu Gly Thr Val Gln Asp Glu Leu Pro
1505                1510                1515                1520

Gly Leu Pro Glu Leu Asn Pro Glu Asp Leu Ala Glu Cys Arg Thr Leu
                1525                1530                1535

Gly Glu Ile Val Thr Tyr Met Asn Ser Lys Leu Ala Asp Gly Ser Lys
            1540                1545                1550

Leu Pro Ala Glu Gly Ser Met His Tyr Gln Leu Ser Thr Ser Thr Ala
        1555                1560                1565

Ala Ala Thr Pro Val Ala Asn Gly Leu Ser Ala Glu Lys Val Gln Ala
    1570                1575                1580

Thr Met Met Ser Val Val Ala Asp Lys Thr Gly Tyr Pro Thr Glu Met
1585                1590                1595                1600

Leu Glu Leu Glu Met Asp Met Glu Ala Asp Leu Gly Ile Asp Ser Ile
                1605                1610                1615

Lys Arg Val Glu Ile Leu Gly Thr Val Gln Asp Glu Leu Pro Gly Leu
            1620                1625                1630

Pro Glu Leu Asn Pro Glu Asp Leu Ala Glu Cys Arg Thr Leu Gly Glu
        1635                1640                1645

Ile Val Asp Tyr Met Gly Ser Lys Leu Pro Ala Glu Gly Ser Ala Asn
    1650                1655                1660

Thr Ser Ala Ala Ala Ser Leu Asn Val Ser Ala Val Ala Ala Pro Gln
1665                1670                1675                1680

Ala Ala Ala Thr Pro Val Ser Asn Gly Leu Ser Ala Glu Lys Val Gln
                1685                1690                1695

Ser Thr Met Met Ser Val Val Ala Glu Lys Thr Gly Tyr Pro Thr Glu
            1700                1705                1710

Met Leu Glu Leu Gly Met Asp Met Glu Ala Asp Leu Gly Ile Asp Ser
        1715                1720                1725

Ile Lys Arg Val Glu Ile Leu Gly Thr Val Gln Asp Glu Leu Pro Gly
    1730                1735                1740

Leu Pro Glu Leu Asn Pro Glu Asp Leu Ala Glu Cys Arg Thr Leu Gly
1745                1750                1755                1760

Glu Ile Val Asp Tyr Met Asn Ser Lys Leu Ala Asp Gly Ser Lys Leu
                1765                1770                1775

Pro Ala Glu Gly Ser Ala Asn Thr Ser Ala Thr Ala Ala Thr Pro Ala
            1780                1785                1790

Val Asn Gly Leu Ser Ala Asp Lys Val Gln Ala Thr Met Met Ser Val
        1795                1800                1805

Val Ala Glu Lys Thr Gly Tyr Pro Thr Glu Met Leu Glu Leu Gly Met
    1810                1815                1820

Asp Met Glu Ala Asp Leu Gly Ile Asp Ser Ile Lys Arg Val Glu Ile
1825                1830                1835                1840
```

-continued

```
Leu Gly Thr Val Gln Asp Glu Leu Pro Gly Leu Pro Glu Leu Asn Pro
                1845                1850                1855

Glu Asp Leu Ala Glu Cys Arg Thr Leu Gly Glu Ile Val Ser Tyr Met
            1860                1865                1870

Asn Ser Gln Leu Ala Asp Gly Ser Lys Leu Ser Thr Ser Ala Ala Glu
        1875                1880                1885

Gly Ser Ala Asp Thr Ser Ala Ala Asn Ala Ala Lys Pro Ala Ala Ile
    1890                1895                1900

Ser Ala Glu Pro Ser Val Glu Leu Pro Pro His Ser Glu Val Ala Leu
1905                1910                1915                1920

Lys Lys Leu Asn Ala Ala Asn Lys Leu Glu Asn Cys Phe Ala Ala Asp
                1925                1930                1935

Ala Ser Val Val Ile Asn Asp Asp Gly His Asn Ala Gly Val Leu Ala
            1940                1945                1950

Glu Lys Leu Ile Lys Gln Gly Leu Lys Val Ala Val Val Arg Leu Pro
        1955                1960                1965

Lys Gly Gln Pro Gln Ser Pro Leu Ser Ser Asp Val Ala Ser Phe Glu
    1970                1975                1980

Leu Ala Ser Ser Gln Glu Ser Glu Leu Glu Ala Ser Ile Thr Ala Val
1985                1990                1995                2000

Ile Ala Gln Ile Glu Thr Gln Val Gly Ala Ile Gly Gly Phe Ile His
                2005                2010                2015

Leu Gln Pro Glu Ala Asn Thr Glu Glu Gln Thr Ala Val Asn Leu Asp
            2020                2025                2030

Ala Gln Ser Phe Thr His Val Ser Asn Ala Phe Leu Trp Ala Lys Leu
        2035                2040                2045

Leu Gln Pro Lys Leu Val Ala Gly Ala Asp Ala Arg Arg Cys Phe Val
    2050                2055                2060

Thr Val Ser Arg Ile Asp Gly Gly Phe Gly Tyr Leu Asn Thr Asp Ala
2065                2070                2075                2080

Leu Lys Asp Ala Glu Leu Asn Gln Ala Ala Leu Ala Gly Leu Thr Lys
                2085                2090                2095

Thr Leu Ser His Glu Trp Pro Gln Val Phe Cys Arg Ala Leu Asp Ile
            2100                2105                2110

Ala Thr Asp Val Asp Ala Thr His Leu Ala Asp Ala Ile Thr Ser Glu
        2115                2120                2125

Leu Phe Asp Ser Gln Ala Gln Leu Pro Glu Val Gly Leu Ser Leu Ile
    2130                2135                2140

Asp Gly Lys Val Asn Arg Val Thr Leu Val Ala Ala Glu Ala Ala Asp
2145                2150                2155                2160

Lys Thr Ala Lys Ala Glu Leu Asn Ser Thr Asp Lys Ile Leu Val Thr
                2165                2170                2175

Gly Gly Ala Lys Gly Val Thr Phe Glu Cys Ala Leu Ala Leu Ala Ser
            2180                2185                2190

Arg Ser Gln Ser His Phe Ile Leu Ala Gly Arg Ser Glu Leu Gln Ala
        2195                2200                2205

Leu Pro Ser Trp Ala Glu Gly Lys Gln Thr Ser Glu Leu Lys Ser Ala
    2210                2215                2220

Ala Ile Ala His Ile Ile Ser Thr Gly Gln Lys Pro Thr Pro Lys Gln
2225                2230                2235                2240

Val Glu Ala Ala Val Trp Pro Val Gln Ser Ser Ile Glu Ile Asn Ala
                2245                2250                2255

Ala Leu Ala Ala Phe Asn Lys Val Gly Ala Ser Ala Glu Tyr Val Ser
            2260                2265                2270
```

Met Asp Val Thr Asp Ser Ala Ala Ile Thr Ala Ala Leu Asn Gly Arg
2275 2280 2285

Ser Asn Glu Ile Thr Gly Leu Ile His Gly Ala Gly Val Leu Ala Asp
2290 2295 2300

Lys His Ile Gln Asp Lys Thr Leu Ala Glu Leu Ala Lys Val Tyr Gly
2305 2310 2315 2320

Thr Lys Val Asn Gly Leu Lys Ala Leu Leu Ala Ala Leu Glu Pro Ser
2325 2330 2335

Lys Ile Lys Leu Leu Ala Met Phe Ser Ser Ala Ala Gly Phe Tyr Gly
2340 2345 2350

Asn Ile Gly Gln Ser Asp Tyr Ala Met Ser Asn Asp Ile Leu Asn Lys
2355 2360 2365

Ala Ala Leu Gln Phe Thr Ala Arg Asn Pro Gln Ala Lys Val Met Ser
2370 2375 2380

Phe Asn Trp Gly Pro Trp Asp Gly Gly Met Val Asn Pro Ala Leu Lys
2385 2390 2395 2400

Lys Met Phe Thr Glu Arg Gly Val Tyr Val Ile Pro Leu Lys Ala Gly
2405 2410 2415

Ala Glu Leu Phe Ala Thr Gln Leu Leu Ala Glu Thr Gly Val Gln Leu
2420 2425 2430

Leu Ile Gly Thr Ser Met Gln Gly Gly Ser Asp Thr Lys Ala Thr Glu
2435 2440 2445

Thr Ala Ser Val Lys Lys Leu Asn Ala Gly Glu Val Leu Ser Ala Ser
2450 2455 2460

His Pro Arg Ala Gly Ala Gln Lys Thr Pro Leu Gln Ala Val Thr Ala
2465 2470 2475 2480

Thr Arg Leu Leu Thr Pro Ser Ala Met Val Phe Ile Glu Asp His Arg
2485 2490 2495

Ile Gly Gly Asn Ser Val Leu Pro Thr Val Cys Ala Ile Asp Trp Met
2500 2505 2510

Arg Glu Ala Ala Ser Asp Met Leu Gly Ala Gln Val Lys Val Leu Asp
2515 2520 2525

Tyr Lys Leu Leu Lys Gly Ile Val Phe Glu Thr Asp Glu Pro Gln Glu
2530 2535 2540

Leu Thr Leu Glu Leu Thr Pro Asp Asp Ser Asp Glu Ala Thr Leu Gln
2545 2550 2555 2560

Ala Leu Ile Ser Cys Asn Gly Arg Pro Gln Tyr Lys Ala Thr Leu Ile
2565 2570 2575

Ser Asp Asn Ala Asp Ile Lys Gln Leu Asn Lys Gln Phe Asp Leu Ser
2580 2585 2590

Ala Lys Ala Ile Thr Thr Ala Lys Glu Leu Tyr Ser Asn Gly Thr Leu
2595 2600 2605

Phe His Gly Pro Arg Leu Gln Gly Ile Gln Ser Val Val Gln Phe Asp
2610 2615 2620

Asp Gln Gly Leu Ile Ala Lys Val Ala Leu Pro Lys Val Glu Leu Ser
2625 2630 2635 2640

Asp Cys Gly Glu Phe Leu Pro Gln Thr His Met Gly Gly Ser Gln Pro
2645 2650 2655

Phe Ala Glu Asp Leu Leu Leu Gln Ala Met Leu Val Trp Ala Arg Leu
2660 2665 2670

Lys Thr Gly Ser Ala Ser Leu Pro Ser Ser Ile Gly Glu Phe Thr Ser
2675 2680 2685

Tyr Gln Pro Met Ala Phe Gly Glu Thr Gly Thr Ile Glu Leu Glu Val

```
2690                2695                2700

Ile Lys His Asn Lys Arg Ser Leu Glu Ala Asn Val Ala Leu Tyr Arg
2705                2710                2715                2720

Asp Asn Gly Glu Leu Ser Ala Met Phe Lys Ser Ala Lys Ile Thr Ile
                2725                2730                2735

Ser Lys Ser Leu Asn Ser Ala Phe Leu Pro Ala Val Leu Ala Asn Asp
            2740                2745                2750

Ser Glu Ala Asn
        2755
```

( 2 ) INFORMATION FOR SEQ ID NO:12:

( i ) SEQUENCE CHARACTERISTICS:
( A ) LENGTH: 2340 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( A ) ORGANISM: Shewanella putrefaciens SCRC-2874 (FERM BP- 1625)

( i x ) FEATURE:
( A ) NAME/KEY: CDS
( B ) LOCATION: 1..2340

( i x ) FEATURE:
( A ) NAME/KEY: mat_peptide
( B ) LOCATION: 1..2340

( x i ) SEQUENCE DESCRIPTION: SEQ ID NO:12:

```
GTG GAA CAA ACG CCT AAA GCT AGT GCG ATG CCG CTG CGC ATC GCA CTT      48
Val Glu Gln Thr Pro Lys Ala Ser Ala Met Pro Leu Arg Ile Ala Leu
  1               5                  10                  15

ATC TTA CTG CCA ACA CCG CAG TTT GAA GTT AAC TCT GTC GAC CAG TCA      96
Ile Leu Leu Pro Thr Pro Gln Phe Glu Val Asn Ser Val Asp Gln Ser
            20                  25                  30

GTA TTA GCC AGC TAT CAA ACA CTG CAG CCT GAG CTA AAT GCC CTG CTT     144
Val Leu Ala Ser Tyr Gln Thr Leu Gln Pro Glu Leu Asn Ala Leu Leu
        35                  40                  45

AAT AGT GCG CCG ACA CCT GAA ATG CTC AGC ATC ACT ATC TCA GAT GAT     192
Asn Ser Ala Pro Thr Pro Glu Met Leu Ser Ile Thr Ile Ser Asp Asp
    50                  55                  60

AGC GAT GCA AAC AGC TTT GAG TCG CAG CTA AAT GCT GCG ACC AAC GCA     240
Ser Asp Ala Asn Ser Phe Glu Ser Gln Leu Asn Ala Ala Thr Asn Ala
 65                  70                  75                  80

ATT AAC AAT GGC TAT ATC GTC AAG CTT GCT ACG GCA ACT CAC GCT TTG     288
Ile Asn Asn Gly Tyr Ile Val Lys Leu Ala Thr Ala Thr His Ala Leu
                 85                  90                  95

TTA ATG CTG CCT GCA TTA AAA GCG GCG CAA ATG CGG ATC CAT CCT CAT     336
Leu Met Leu Pro Ala Leu Lys Ala Ala Gln Met Arg Ile His Pro His
            100                 105                 110

GCG CAG CTT GCC GCT ATG CAG CAA GCT AAA TCG ACG CCA ATG AGT CAA     384
Ala Gln Leu Ala Ala Met Gln Gln Ala Lys Ser Thr Pro Met Ser Gln
        115                 120                 125

GTA TCT GGT GAG CTA AAG CTT GGC GCT AAT GCG CTA AGC CTA GCT CAG     432
Val Ser Gly Glu Leu Lys Leu Gly Ala Asn Ala Leu Ser Leu Ala Gln
    130                 135                 140

ACT AAT GCG CTG TCT CAT GCT TTA AGC CAA GCC AAG CGT AAC TTA ACT     480
Thr Asn Ala Leu Ser His Ala Leu Ser Gln Ala Lys Arg Asn Leu Thr
145                 150                 155                 160

GAT GTC AGC GTG AAT GAG TGT TTT GAG AAC CTC AAA AGT GAA CAG CAG     528
```

-continued

Asp Val Ser Val Asn Glu Cys Phe Glu Asn Leu Lys Ser Glu Gln Gln
165 170 175

TTC ACA GAG GTT TAT TCG CTT ATT CAG CAA CTT GCT AGC CGC ACC CAT 576
Phe Thr Glu Val Tyr Ser Leu Ile Gln Gln Leu Ala Ser Arg Thr His
180 185 190

GTG AGA AAA GAG GTT AAT CAA GGT GTG GAA CTT GGC CCT AAA CAA GCC 624
Val Arg Lys Glu Val Asn Gln Gly Val Glu Leu Gly Pro Lys Gln Ala
195 200 205

AAA AGC CAC TAT TGG TTT AGC GAA TTT CAC CAA AAC CGT GTT GCT GCC 672
Lys Ser His Tyr Trp Phe Ser Glu Phe His Gln Asn Arg Val Ala Ala
210 215 220

ATC AAC TTT ATT AAT GGC CAA CAA GCA ACC AGC TAT GTG CTT ACT CAA 720
Ile Asn Phe Ile Asn Gly Gln Gln Ala Thr Ser Tyr Val Leu Thr Gln
225 230 235 240

GGT TCA GGA TTG TTA GCT GCG AAA TCA ATG CTA AAC CAG CAA AGA TTA 768
Gly Ser Gly Leu Leu Ala Ala Lys Ser Met Leu Asn Gln Gln Arg Leu
245 250 255

ATG TTT ATC TTG CCG GGT AAC AGT CAG CAA CAA ATA ACC GCA TCA ATA 816
Met Phe Ile Leu Pro Gly Asn Ser Gln Gln Gln Ile Thr Ala Ser Ile
260 265 270

ACT CAG TTA ATG CAG CAA TTA GAG CGT TTG CAG GTA ACT GAG GTT AAT 864
Thr Gln Leu Met Gln Gln Leu Glu Arg Leu Gln Val Thr Glu Val Asn
275 280 285

GAG CTT TCT CTA GAA TGC CAA CTA GAG CTG CTC AGC ATA ATG TAT GAC 912
Glu Leu Ser Leu Glu Cys Gln Leu Glu Leu Leu Ser Ile Met Tyr Asp
290 295 300

AAC TTA GTC AAC GCA GAC AAA CTC ACT ACT CGC GAT AGT AAG CCC GCT 960
Asn Leu Val Asn Ala Asp Lys Leu Thr Thr Arg Asp Ser Lys Pro Ala
305 310 315 320

TAT CAG GCT GTG ATT CAA GCA AGC TCT GTT AGC GCT GCA AAG CAA GAG 1008
Tyr Gln Ala Val Ile Gln Ala Ser Ser Val Ser Ala Ala Lys Gln Glu
325 330 335

TTA AGC GCG CTT AAC GAT GCA CTC ACA GCG CTG TTT GCT GAG CAA ACA 1056
Leu Ser Ala Leu Asn Asp Ala Leu Thr Ala Leu Phe Ala Glu Gln Thr
340 345 350

AAC GCC ACA TCA ACG AAT AAA GGC TTA ATC CAA TAC AAA ACA CCG GCG 1104
Asn Ala Thr Ser Thr Asn Lys Gly Leu Ile Gln Tyr Lys Thr Pro Ala
355 360 365

GGC AGT TAC TTA ACC CTA ACA CCG CTT GGC AGC AAC AAT GAC AAC GCC 1152
Gly Ser Tyr Leu Thr Leu Thr Pro Leu Gly Ser Asn Asn Asp Asn Ala
370 375 380

CAA GCG GGT CTT GCT TTT GTC TAT CCG GGT GTG GGA ACG GTT TAC GCC 1200
Gln Ala Gly Leu Ala Phe Val Tyr Pro Gly Val Gly Thr Val Tyr Ala
385 390 395 400

GAT ATG CTT AAT GAG CTG CAT CAG TAC TTC CCT GCG CTT TAC GCC AAA 1248
Asp Met Leu Asn Glu Leu His Gln Tyr Phe Pro Ala Leu Tyr Ala Lys
405 410 415

CTT GAG CGT GAA GGC GAT TTA AAG GCG ATG CTA CAA GCA GAA GAT ATC 1296
Leu Glu Arg Glu Gly Asp Leu Lys Ala Met Leu Gln Ala Glu Asp Ile
420 425 430

TAT CAT CTT GAC CCT AAA CAT GCT GCC CAA ATG AGC TTA GGT GAC TTA 1344
Tyr His Leu Asp Pro Lys His Ala Ala Gln Met Ser Leu Gly Asp Leu
435 440 445

GCC ATT GCT GGC GTG GGG AGC AGC TAC CTG TTA ACT CAG CTG CTC ACC 1392
Ala Ile Ala Gly Val Gly Ser Ser Tyr Leu Leu Thr Gln Leu Leu Thr
450 455 460

GAT GAG TTT AAT ATT AAG CCT AAT TTT GCA TTA GGT TAC TCA ATG GGT 1440
Asp Glu Phe Asn Ile Lys Pro Asn Phe Ala Leu Gly Tyr Ser Met Gly
465 470 475 480

GAA GCA TCA ATG TGG GCA AGC TTA GGC GTA TGG CAA AAC CCG CAT GCG 1488

-continued

```
Glu Ala Ser Met Trp Ala Ser Leu Gly Val Trp Gln Asn Pro His Ala
                485                 490                 495

CTG ATC AGC AAA ACC CAA ACC GAC CCG CTA TTT ACT TCT GCT ATT TCC      1536
Leu Ile Ser Lys Thr Gln Thr Asp Pro Leu Phe Thr Ser Ala Ile Ser
            500                 505                 510

GGC AAA TTG ACC GCG GTT AGA CAA GCT TGG CAG CTT GAT GAT ACC GCA      1584
Gly Lys Leu Thr Ala Val Arg Gln Ala Trp Gln Leu Asp Asp Thr Ala
        515                 520                 525

GCG GAA ATC CAG TGG AAT AGC TTT GTG GTT AGA AGT GAA GCA GCG CCG      1632
Ala Glu Ile Gln Trp Asn Ser Phe Val Val Arg Ser Glu Ala Ala Pro
    530                 535                 540

ATT GAA GCC TTG CTA AAA GAT TAC CCA CAC GCT TAC CTC GCG ATT ATT      1680
Ile Glu Ala Leu Leu Lys Asp Tyr Pro His Ala Tyr Leu Ala Ile Ile
545                 550                 555                 560

CAA GGG GAT ACC TGC GTA ATC GCT GGC TGT GAA ATC CAA TGT AAA GCG      1728
Gln Gly Asp Thr Cys Val Ile Ala Gly Cys Glu Ile Gln Cys Lys Ala
                565                 570                 575

CTA CTT GCA GCA CTG GGT AAA CGC GGT ATT GCA GCT AAT CGT GTA ACG      1776
Leu Leu Ala Ala Leu Gly Lys Arg Gly Ile Ala Ala Asn Arg Val Thr
            580                 585                 590

GCG ATG CAT ACG CAG CCT GCG ATG CAA GAG CAT CAA AAT GTG ATG GAT      1824
Ala Met His Thr Gln Pro Ala Met Gln Glu His Gln Asn Val Met Asp
        595                 600                 605

TTT TAT CTG CAA CCG TTA AAA GCA GAG CTT CCT AGT GAA ATA AGC TTT      1872
Phe Tyr Leu Gln Pro Leu Lys Ala Glu Leu Pro Ser Glu Ile Ser Phe
    610                 615                 620

ATC AGC GCC GCT GAT TTA ACT GCC AAG CAA ACG GTG AGT GAG CAA GCA      1920
Ile Ser Ala Ala Asp Leu Thr Ala Lys Gln Thr Val Ser Glu Gln Ala
625                 630                 635                 640

CTT AGC AGC CAA GTC GTT GCT CAG TCT ATT GCC GAC ACC TTC TGC CAA      1968
Leu Ser Ser Gln Val Val Ala Gln Ser Ile Ala Asp Thr Phe Cys Gln
                645                 650                 655

ACC TTG GAC TTT ACC GCG CTA GTA CAT CAC GCC CAA CAT CAA GGC GCT      2016
Thr Leu Asp Phe Thr Ala Leu Val His His Ala Gln His Gln Gly Ala
            660                 665                 670

AAG CTG TTT GTT GAA ATT GGC GCG GAT AGA CAA AAC TGC ACC TTG ATA      2064
Lys Leu Phe Val Glu Ile Gly Ala Asp Arg Gln Asn Cys Thr Leu Ile
        675                 680                 685

GAC AAG ATT GTT AAA CAA GAT GGT GCC AGC AGT GTA CAA CAT CAA CCT      2112
Asp Lys Ile Val Lys Gln Asp Gly Ala Ser Ser Val Gln His Gln Pro
    690                 695                 700

TGT TGC ACA GTG CCT ATG AAC GCA AAA GGT AGC CAA GAT ATT ACC AGC      2160
Cys Cys Thr Val Pro Met Asn Ala Lys Gly Ser Gln Asp Ile Thr Ser
705                 710                 715                 720

GTG ATT AAA GCG CTT GGC CAA TTA ATT AGC CAT CAG GTG CCA TTA TCG      2208
Val Ile Lys Ala Leu Gly Gln Leu Ile Ser His Gln Val Pro Leu Ser
                725                 730                 735

GTG CAA CCA TTT ATT GAT GGA CTC AAG CGC GAG CTA ACA CTT TGC CAA      2256
Val Gln Pro Phe Ile Asp Gly Leu Lys Arg Glu Leu Thr Leu Cys Gln
            740                 745                 750

TTG ACC AGC CAA CAG CTG GCA GCA CAT GCA AAT GTT GAC AGC AAG TTT      2304
Leu Thr Ser Gln Gln Leu Ala Ala His Ala Asn Val Asp Ser Lys Phe
        755                 760                 765

GAG TCT AAC CAA GAC CAT TTA CTT CAA GGG GAA GTC                      2340
Glu Ser Asn Gln Asp His Leu Leu Gln Gly Glu Val
    770                 775                 780
```

( 2 ) INFORMATION FOR SEQ ID NO:13:

( i ) SEQUENCE CHARACTERISTICS:

( A ) LENGTH: 780 amino acids ( B ) TYPE: amino acid
( D ) TOPOLOGY: linear ( i i ) MOLECULE TYPE: protein ( x i ) SEQUENCE DESCRIPTION: SEQ ID NO:13:

```
Val Glu Gln Thr Pro Lys Ala Ser Ala Met Pro Leu Arg Ile Ala Leu
 1               5                  10                  15

Ile Leu Leu Pro Thr Pro Gln Phe Glu Val Asn Ser Val Asp Gln Ser
            20                  25                  30

Val Leu Ala Ser Tyr Gln Thr Leu Gln Pro Glu Leu Asn Ala Leu Leu
        35                  40                  45

Asn Ser Ala Pro Thr Pro Glu Met Leu Ser Ile Thr Ile Ser Asp Asp
    50                  55                  60

Ser Asp Ala Asn Ser Phe Glu Ser Gln Leu Asn Ala Ala Thr Asn Ala
65                  70                  75                  80

Ile Asn Asn Gly Tyr Ile Val Lys Leu Ala Thr Ala Thr His Ala Leu
                85                  90                  95

Leu Met Leu Pro Ala Leu Lys Ala Ala Gln Met Arg Ile His Pro His
            100                 105                 110

Ala Gln Leu Ala Ala Met Gln Gln Ala Lys Ser Thr Pro Met Ser Gln
        115                 120                 125

Val Ser Gly Glu Leu Lys Leu Gly Ala Asn Ala Leu Ser Leu Ala Gln
    130                 135                 140

Thr Asn Ala Leu Ser His Ala Leu Ser Gln Ala Lys Arg Asn Leu Thr
145                 150                 155                 160

Asp Val Ser Val Asn Glu Cys Phe Glu Asn Leu Lys Ser Glu Gln Gln
                165                 170                 175

Phe Thr Glu Val Tyr Ser Leu Ile Gln Gln Leu Ala Ser Arg Thr His
            180                 185                 190

Val Arg Lys Glu Val Asn Gln Gly Val Glu Leu Gly Pro Lys Gln Ala
        195                 200                 205

Lys Ser His Tyr Trp Phe Ser Glu Phe His Gln Asn Arg Val Ala Ala
    210                 215                 220

Ile Asn Phe Ile Asn Gly Gln Gln Ala Thr Ser Tyr Val Leu Thr Gln
225                 230                 235                 240

Gly Ser Gly Leu Leu Ala Ala Lys Ser Met Leu Asn Gln Gln Arg Leu
                245                 250                 255

Met Phe Ile Leu Pro Gly Asn Ser Gln Gln Gln Ile Thr Ala Ser Ile
            260                 265                 270

Thr Gln Leu Met Gln Gln Leu Glu Arg Leu Gln Val Thr Glu Val Asn
        275                 280                 285

Glu Leu Ser Leu Glu Cys Gln Leu Glu Leu Leu Ser Ile Met Tyr Asp
    290                 295                 300

Asn Leu Val Asn Ala Asp Lys Leu Thr Thr Arg Asp Ser Lys Pro Ala
305                 310                 315                 320

Tyr Gln Ala Val Ile Gln Ala Ser Ser Val Ser Ala Ala Lys Gln Glu
                325                 330                 335

Leu Ser Ala Leu Asn Asp Ala Leu Thr Ala Leu Phe Ala Glu Gln Thr
            340                 345                 350

Asn Ala Thr Ser Thr Asn Lys Gly Leu Ile Gln Tyr Lys Thr Pro Ala
        355                 360                 365

Gly Ser Tyr Leu Thr Leu Thr Pro Leu Gly Ser Asn Asn Asp Asn Ala
    370                 375                 380

Gln Ala Gly Leu Ala Phe Val Tyr Pro Gly Val Gly Thr Val Tyr Ala
```

-continued 385 390 395 400

Asp Met Leu Asn Glu Leu His Gln Tyr Phe Pro Ala Leu Tyr Ala Lys
405 410 415

Leu Glu Arg Glu Gly Asp Leu Lys Ala Met Leu Gln Ala Glu Asp Ile
420 425 430

Tyr His Leu Asp Pro Lys His Ala Ala Gln Met Ser Leu Gly Asp Leu
435 440 445

Ala Ile Ala Gly Val Gly Ser Ser Tyr Leu Leu Thr Gln Leu Leu Thr
450 455 460

Asp Glu Phe Asn Ile Lys Pro Asn Phe Ala Leu Gly Tyr Ser Met Gly
465 470 475 480

Glu Ala Ser Met Trp Ala Ser Leu Gly Val Trp Gln Asn Pro His Ala
485 490 495

Leu Ile Ser Lys Thr Gln Thr Asp Pro Leu Phe Thr Ser Ala Ile Ser
500 505 510

Gly Lys Leu Thr Ala Val Arg Gln Ala Trp Gln Leu Asp Asp Thr Ala
515 520 525

Ala Glu Ile Gln Trp Asn Ser Phe Val Val Arg Ser Glu Ala Ala Pro
530 535 540

Ile Glu Ala Leu Leu Lys Asp Tyr Pro His Ala Tyr Leu Ala Ile Ile
545 550 555 560

Gln Gly Asp Thr Cys Val Ile Ala Gly Cys Glu Ile Gln Cys Lys Ala
565 570 575

Leu Leu Ala Ala Leu Gly Lys Arg Gly Ile Ala Ala Asn Arg Val Thr
580 585 590

Ala Met His Thr Gln Pro Ala Met Gln Glu His Gln Asn Val Met Asp
595 600 605

Phe Tyr Leu Gln Pro Leu Lys Ala Glu Leu Pro Ser Glu Ile Ser Phe
610 615 620

Ile Ser Ala Ala Asp Leu Thr Ala Lys Gln Thr Val Ser Glu Gln Ala
625 630 635 640

Leu Ser Ser Gln Val Val Ala Gln Ser Ile Ala Asp Thr Phe Cys Gln
645 650 655

Thr Leu Asp Phe Thr Ala Leu Val His His Ala Gln His Gln Gly Ala
660 665 670

Lys Leu Phe Val Glu Ile Gly Ala Asp Arg Gln Asn Cys Thr Leu Ile
675 680 685

Asp Lys Ile Val Lys Gln Asp Gly Ala Ser Ser Val Gln His Gln Pro
690 695 700

Cys Cys Thr Val Pro Met Asn Ala Lys Gly Ser Gln Asp Ile Thr Ser
705 710 715 720

Val Ile Lys Ala Leu Gly Gln Leu Ile Ser His Gln Val Pro Leu Ser
725 730 735

Val Gln Pro Phe Ile Asp Gly Leu Lys Arg Glu Leu Thr Leu Cys Gln
740 745 750

Leu Thr Ser Gln Gln Leu Ala Ala His Ala Asn Val Asp Ser Lys Phe
755 760 765

Glu Ser Asn Gln Asp His Leu Leu Gln Gly Glu Val
770 775 780

( 2 ) INFORMATION FOR SEQ ID NO:14:

( i ) SEQUENCE CHARACTERISTICS:

( A ) LENGTH: 6012 base pairs ( B ) TYPE: nucleic acid ( C ) STRANDEDNESS: double
( D ) TOPOLOGY: linear ( i i ) MOLECULE TYPE: DNA (genomic)

( v i ) ORIGINAL SOURCE:
( A ) ORGANISM: Shewanella putrefaciens SCRC-2874 (FERM BP- 1625)

( i x ) FEATURE:
( A ) NAME/KEY: CDS
( B ) LOCATION: 1..6012

( i x ) FEATURE:
( A ) NAME/KEY: mat_peptide
( B ) LOCATION: 1..6012

( x i ) SEQUENCE DESCRIPTION: SEQ ID NO:14:

```
ATG TCA TTA CCA GAC AAT GCT TCT AAC CAC CTT TCT GCC AAC CAG AAA      48
Met Ser Leu Pro Asp Asn Ala Ser Asn His Leu Ser Ala Asn Gln Lys
  1               5                  10                  15

GGC GCA TCT CAG GCA AGT AAA ACC AGT AAG CAA AGC AAA ATC GCC ATT      96
Gly Ala Ser Gln Ala Ser Lys Thr Ser Lys Gln Ser Lys Ile Ala Ile
             20                  25                  30

GTC GGT TTA GCC ACT CTG TAT CCA GAC GCT AAA ACC CCG CAA GAA TTT     144
Val Gly Leu Ala Thr Leu Tyr Pro Asp Ala Lys Thr Pro Gln Glu Phe
         35                  40                  45

TGG CAG AAT TTG CTG GAT AAA CGC GAC TCT CGC AGC ACC TTA ACT AAC     192
Trp Gln Asn Leu Leu Asp Lys Arg Asp Ser Arg Ser Thr Leu Thr Asn
     50                  55                  60

GAA AAA CTC GGC GCT AAC AGC CAA GAT TAT CAA GGT GTG CAA GGC CAA     240
Glu Lys Leu Gly Ala Asn Ser Gln Asp Tyr Gln Gly Val Gln Gly Gln
 65                  70                  75                  80

TCT GAC CGT TTT TAT TGT AAT AAA GGC GGC TAC ATT GAG AAC TTC AGC     288
Ser Asp Arg Phe Tyr Cys Asn Lys Gly Gly Tyr Ile Glu Asn Phe Ser
                 85                  90                  95

TTT AAT GCT GCA GGC TAC AAA TTG CCG GAG CAA AGC TTA AAT GGC TTG     336
Phe Asn Ala Ala Gly Tyr Lys Leu Pro Glu Gln Ser Leu Asn Gly Leu
            100                 105                 110

GAC GAC AGC TTC CTT TGG GCG CTC GAT ACT AGC CGT AAC GCA CTA ATT     384
Asp Asp Ser Phe Leu Trp Ala Leu Asp Thr Ser Arg Asn Ala Leu Ile
        115                 120                 125

GAT GCT GGT ATT GAT ATC AAC GGC GCT GAT TTA AGC CGC GCA GGT GTA     432
Asp Ala Gly Ile Asp Ile Asn Gly Ala Asp Leu Ser Arg Ala Gly Val
    130                 135                 140

GTC ATG GGC GCG CTG TCG TTC CCA ACT ACC CGC TCA AAC GAT CTG TTT     480
Val Met Gly Ala Leu Ser Phe Pro Thr Thr Arg Ser Asn Asp Leu Phe
145                 150                 155                 160

TTG CCA ATT TAT CAC AGC GCC GTT GAA AAA GCC CTG CAA GAT AAA CTA     528
Leu Pro Ile Tyr His Ser Ala Val Glu Lys Ala Leu Gln Asp Lys Leu
                165                 170                 175

GGC GTA AAG GCA TTT AAG CTA AGC CCA ACT AAT GCT CAT ACC GCT CGC     576
Gly Val Lys Ala Phe Lys Leu Ser Pro Thr Asn Ala His Thr Ala Arg
            180                 185                 190

GCG GCA AAT GAG AGC AGC CTA AAT GCA GCC AAT GGT GCC ATT GCC CAT     624
Ala Ala Asn Glu Ser Ser Leu Asn Ala Ala Asn Gly Ala Ile Ala His
        195                 200                 205

AAC AGC TCA AAA GTG GTG GCC GAT GCA CTT GGC CTT GGC GGC GCA CAA     672
Asn Ser Ser Lys Val Val Ala Asp Ala Leu Gly Leu Gly Gly Ala Gln
    210                 215                 220

CTA AGC CTA GAT GCT GCC TGT GCT AGT TCG GTT TAC TCA TTA AAG CTT     720
Leu Ser Leu Asp Ala Ala Cys Ala Ser Ser Val Tyr Ser Leu Lys Leu
225                 230                 235                 240

GCC TGC GAT TAC CTA AGC ACT GGC AAA GCC GAT ATC ATG CTA GCA GGC     768
```

-continued

```
Ala Cys Asp Tyr Leu Ser Thr Gly Lys Ala Asp Ile Met Leu Ala Gly
                245                 250                 255

GCA GTA TCT GGC GCG GAT CCT TTC TTT ATT AAT ATG GGA TTC TCA ATC      816
Ala Val Ser Gly Ala Asp Pro Phe Phe Ile Asn Met Gly Phe Ser Ile
            260                 265                 270

TTC CAC GCC TAC CCA GAC CAT GGT ATC TCA GTA CCG TTT GAT GCC AGC      864
Phe His Ala Tyr Pro Asp His Gly Ile Ser Val Pro Phe Asp Ala Ser
        275                 280                 285

AGT AAA GGT TTG TTT GCT GGC GAA GGC GCT GGC GTA TTA GTG CTT AAA      912
Ser Lys Gly Leu Phe Ala Gly Glu Gly Ala Gly Val Leu Val Leu Lys
    290                 295                 300

CGT CTT GAA GAT GCC GAG CGC GAC AAT GAC AAA ATC TAT GCG GTT GTT      960
Arg Leu Glu Asp Ala Glu Arg Asp Asn Asp Lys Ile Tyr Ala Val Val
305                 310                 315                 320

AGC GGC GTA GGT CTA TCA AAC GAC GGT AAA GGC CAG TTT GTA TTA AGC     1008
Ser Gly Val Gly Leu Ser Asn Asp Gly Lys Gly Gln Phe Val Leu Ser
                325                 330                 335

CCT AAT CCA AAA GGT CAG GTG AAG GCC TTT GAA CGT GCT TAT GCT GCC     1056
Pro Asn Pro Lys Gly Gln Val Lys Ala Phe Glu Arg Ala Tyr Ala Ala
            340                 345                 350

AGT GAC ATT GAG CCA AAA GAC ATT GAA GTG ATT GAG TGC CAC GCA ACA     1104
Ser Asp Ile Glu Pro Lys Asp Ile Glu Val Ile Glu Cys His Ala Thr
        355                 360                 365

GGC ACA CCG CTT GGC GAT AAA ATT GAG CTC ACT TCA ATG GAA ACC TTC     1152
Gly Thr Pro Leu Gly Asp Lys Ile Glu Leu Thr Ser Met Glu Thr Phe
    370                 375                 380

TTT GAA GAC AAG CTG CAA GGC ACC GAT GCA CCG TTA ATT GGC TCA GCT     1200
Phe Glu Asp Lys Leu Gln Gly Thr Asp Ala Pro Leu Ile Gly Ser Ala
385                 390                 395                 400

AAG TCT AAC TTA GGC CAC CTA TTA ACT GCA GCG CAT GCG GGG ATC ATG     1248
Lys Ser Asn Leu Gly His Leu Leu Thr Ala Ala His Ala Gly Ile Met
                405                 410                 415

AAG ATG ATC TTC GCC ATG AAA GAA GGT TAC CTG CCG CCA AGT ATC AAT     1296
Lys Met Ile Phe Ala Met Lys Glu Gly Tyr Leu Pro Pro Ser Ile Asn
            420                 425                 430

ATT AGT GAT GCT ATC GCT TCG CCG AAA AAA CTC TTC GGT AAA CCA ACC     1344
Ile Ser Asp Ala Ile Ala Ser Pro Lys Lys Leu Phe Gly Lys Pro Thr
        435                 440                 445

CTG CCT AGC ATG GTT CAA GGC TGG CCA GAT AAG CCA TCG AAT AAT CAT     1392
Leu Pro Ser Met Val Gln Gly Trp Pro Asp Lys Pro Ser Asn Asn His
    450                 455                 460

TTT GGT GTA AGA ACC CGT CAC GCA GGC GTA TCG GTA TTT GGC TTT GGT     1440
Phe Gly Val Arg Thr Arg His Ala Gly Val Ser Val Phe Gly Phe Gly
465                 470                 475                 480

GGC TGT AAC GCC CAT CTG TTG CTT GAG TCA TAC AAC GGC AAA GGA ACA     1488
Gly Cys Asn Ala His Leu Leu Leu Glu Ser Tyr Asn Gly Lys Gly Thr
                485                 490                 495

GTA AAG GCA GAA GCC ACT CAA GTA CCG CGT CAA GCT GAG CCG CTA AAA     1536
Val Lys Ala Glu Ala Thr Gln Val Pro Arg Gln Ala Glu Pro Leu Lys
            500                 505                 510

GTG GTT GGC CTT GCC TCG CAC TTT GGG CCT CTT AGC AGC ATT AAT GCA     1584
Val Val Gly Leu Ala Ser His Phe Gly Pro Leu Ser Ser Ile Asn Ala
        515                 520                 525

CTC AAC AAT GCT GTG ACC CAA GAT GGG AAT GGC TTT ATC GAA CTG CCG     1632
Leu Asn Asn Ala Val Thr Gln Asp Gly Asn Gly Phe Ile Glu Leu Pro
    530                 535                 540

AAA AAG CGC TGG AAA GGC CTT GAA AAG CAC AGT GAA CTG TTA GCT GAA     1680
Lys Lys Arg Trp Lys Gly Leu Glu Lys His Ser Glu Leu Leu Ala Glu
545                 550                 555                 560

TTT GGC TTA GCA TCT GCG CCA AAA GGT GCT TAT GTT GAT AAC TTC GAG     1728
```

-continued

```
Phe Gly Leu Ala Ser Ala Pro Lys Gly Ala Tyr Val Asp Asn Phe Glu
                565                 570                 575

CTG GAC TTT TTA CGC TTT AAA CTG CCG CCA AAC GAA GAT GAC CGT TTG    1776
Leu Asp Phe Leu Arg Phe Lys Leu Pro Pro Asn Glu Asp Asp Arg Leu
            580                 585                 590

ATC TCA CAG CAG CTA ATG CTA ATG CGA GTA ACA GAC GAA GCC ATT CGT    1824
Ile Ser Gln Gln Leu Met Leu Met Arg Val Thr Asp Glu Ala Ile Arg
        595                 600                 605

GAT GCC AAG CTT GAG CCG GGG CAA AAA GTA GCT GTA TTA GTG GCA ATG    1872
Asp Ala Lys Leu Glu Pro Gly Gln Lys Val Ala Val Leu Val Ala Met
    610                 615                 620

GAA ACT GAG CTT GAA CTG CAT CAG TTC CGC GGC CGG GTT AAC TTG CAT    1920
Glu Thr Glu Leu Glu Leu His Gln Phe Arg Gly Arg Val Asn Leu His
625                 630                 635                 640

ACT CAA TTA GCG CAA AGT CTT GCC GCC ATG GGC GTG AGT TTA TCA ACG    1968
Thr Gln Leu Ala Gln Ser Leu Ala Ala Met Gly Val Ser Leu Ser Thr
                645                 650                 655

GAT GAA TAC CAA GCG CTT GAA GCC ATC GCC ATG GAC AGC GTG CTT GAT    2016
Asp Glu Tyr Gln Ala Leu Glu Ala Ile Ala Met Asp Ser Val Leu Asp
            660                 665                 670

GCT GCC AAG CTC AAT CAG TAC ACC AGC TTT ATT GGT AAT ATT ATG GCG    2064
Ala Ala Lys Leu Asn Gln Tyr Thr Ser Phe Ile Gly Asn Ile Met Ala
        675                 680                 685

TCA CGC GTG GCG TCA CTA TGG GAC TTT AAT GGC CCA GCC TTC ACT ATT    2112
Ser Arg Val Ala Ser Leu Trp Asp Phe Asn Gly Pro Ala Phe Thr Ile
    690                 695                 700

TCA GCA GCA GAG CAA TCT GTG AGC CGC TGT ATC GAT GTG GCG CAA AAC    2160
Ser Ala Ala Glu Gln Ser Val Ser Arg Cys Ile Asp Val Ala Gln Asn
705                 710                 715                 720

CTC ATC ATG GAG GAT AAC CTA GAT GCG GTG GTG ATT GCA GCG GTC GAT    2208
Leu Ile Met Glu Asp Asn Leu Asp Ala Val Val Ile Ala Ala Val Asp
                725                 730                 735

CTC TCT GGT AGC TTT GAG CAA GTC ATT CTT AAA AAT GCC ATT GCA CCT    2256
Leu Ser Gly Ser Phe Glu Gln Val Ile Leu Lys Asn Ala Ile Ala Pro
            740                 745                 750

GTA GCC ATT GAG CCA AAC CTC GAA GCA AGC CTT AAT CCA ACA TCA GCA    2304
Val Ala Ile Glu Pro Asn Leu Glu Ala Ser Leu Asn Pro Thr Ser Ala
        755                 760                 765

AGC TGG AAT GTC GGT GAA GGT GCT GGC GCG GTC GTG CTT GTT AAA AAT    2352
Ser Trp Asn Val Gly Glu Gly Ala Gly Ala Val Val Leu Val Lys Asn
    770                 775                 780

GAA GCT ACA TCG GGC TGC TCA TAC GGC CAA ATT GAT GCA CTT GGC TTT    2400
Glu Ala Thr Ser Gly Cys Ser Tyr Gly Gln Ile Asp Ala Leu Gly Phe
785                 790                 795                 800

GCT AAA ACT GCC GAA ACA GCG TTG GCT ACC GAC AAG CTA CTG AGC CAA    2448
Ala Lys Thr Ala Glu Thr Ala Leu Ala Thr Asp Lys Leu Leu Ser Gln
                805                 810                 815

ACT GCC ACA GAC TTT AAT AAG GTT AAA GTG ATT GAA ACT ATG GCA GCG    2496
Thr Ala Thr Asp Phe Asn Lys Val Lys Val Ile Glu Thr Met Ala Ala
            820                 825                 830

CCT GCT AGC CAA ATT CAA TTA GCG CCA ATA GTT AGC TCT CAA GTG ACT    2544
Pro Ala Ser Gln Ile Gln Leu Ala Pro Ile Val Ser Ser Gln Val Thr
        835                 840                 845

CAC ACT GCT GCA GAG CAG CGT GTT GGT CAC TGC TTT GCT GCA GCG GGT    2592
His Thr Ala Ala Glu Gln Arg Val Gly His Cys Phe Ala Ala Ala Gly
    850                 855                 860

ATG GCA AGC CTA TTA CAC GGC TTA CTT AAC TTA AAT ACT GTA GCC CAA    2640
Met Ala Ser Leu Leu His Gly Leu Leu Asn Leu Asn Thr Val Ala Gln
865                 870                 875                 880

ACC AAT AAA GCC AAT TGC GCG CTT ATC AAC AAT ATC AGT GAA AAC CAA    2688
```

```
Thr Asn Lys Ala Asn Cys Ala Leu Ile Asn Asn Ile Ser Glu Asn Gln
                885                 890                 895

TTA TCA CAG CTG TTG ATT AGC CAA ACA GCG AGC GAA CAA CAA GCA TTA     2736
Leu Ser Gln Leu Leu Ile Ser Gln Thr Ala Ser Glu Gln Gln Ala Leu
            900                 905                 910

ACC GCG CGT TTA AGC AAT GAG CTT AAA TCC GAT GCT AAA CAC CAA CTG     2784
Thr Ala Arg Leu Ser Asn Glu Leu Lys Ser Asp Ala Lys His Gln Leu
        915                 920                 925

GTT AAG CAA GTC ACC TTA GGT GGC CGT GAT ATC TAC CAG CAT ATT GTT     2832
Val Lys Gln Val Thr Leu Gly Gly Arg Asp Ile Tyr Gln His Ile Val
    930                 935                 940

GAT ACA CCG CTT GCA AGC CTT GAA AGC ATT ACT CAG AAA TTG GCG CAA     2880
Asp Thr Pro Leu Ala Ser Leu Glu Ser Ile Thr Gln Lys Leu Ala Gln
945                 950                 955                 960

GCG ACA GCA TCG ACA GTG GTC AAC CAA GTT AAA CCT ATT AAG GCC GCT     2928
Ala Thr Ala Ser Thr Val Val Asn Gln Val Lys Pro Ile Lys Ala Ala
                965                 970                 975

GGC TCA GTC GAA ATG GCT AAC TCA TTC GAA ACG GAA AGC TCA GCA GAG     2976
Gly Ser Val Glu Met Ala Asn Ser Phe Glu Thr Glu Ser Ser Ala Glu
            980                 985                 990

CCA CAA ATA ACA ATT GCA GCA CAA CAG ACT GCA AAC ATT GGC GTC ACC     3024
Pro Gln Ile Thr Ile Ala Ala Gln Gln Thr Ala Asn Ile Gly Val Thr
        995                1000                1005

GCT CAG GCA ACC AAA CGT GAA TTA GGT ACC CCA CCA ATG ACA ACA AAT     3072
Ala Gln Ala Thr Lys Arg Glu Leu Gly Thr Pro Pro Met Thr Thr Asn
   1010                1015                1020

ACC ATT GCT AAT ACA GCA AAT AAT TTA GAC AAG ACT CTT GAG ACT GTT     3120
Thr Ile Ala Asn Thr Ala Asn Asn Leu Asp Lys Thr Leu Glu Thr Val
1025               1030                1035                1040

GCT GGC AAT ACT GTT GCT AGC AAG GTT GGC TCT GGC GAC ATA GTC AAT     3168
Ala Gly Asn Thr Val Ala Ser Lys Val Gly Ser Gly Asp Ile Val Asn
               1045                1050                1055

TTT CAA CAG AAC CAA CAA TTG GCT CAA CAA GCT CAC CTC GCC TTT CTT     3216
Phe Gln Gln Asn Gln Gln Leu Ala Gln Gln Ala His Leu Ala Phe Leu
           1060                1065                1070

GAA AGC CGC AGT GCG GGT ATG AAG GTG GCT GAT GCT TTA TTG AAG CAA     3264
Glu Ser Arg Ser Ala Gly Met Lys Val Ala Asp Ala Leu Leu Lys Gln
       1075                1080                1085

CAG CTA GCT CAA GTA ACA GGC CAA ACT ATC GAT AAT CAG GCC CTC GAT     3312
Gln Leu Ala Gln Val Thr Gly Gln Thr Ile Asp Asn Gln Ala Leu Asp
   1090                1095                1100

ACT CAA GCC GTC GAT ACT CAA ACA AGC GAG AAT GTA GCG ATT GCC GCA     3360
Thr Gln Ala Val Asp Thr Gln Thr Ser Glu Asn Val Ala Ile Ala Ala
1105               1110                1115                1120

GAA TCA CCA GTT CAA GTT ACA ACA CCT GTT CAA GTT ACA ACA CCT GTT     3408
Glu Ser Pro Val Gln Val Thr Thr Pro Val Gln Val Thr Thr Pro Val
               1125                1130                1135

CAA ATC AGT GTT GTG GAG TTA AAA CCA GAT CAC GCT AAT GTG CCA CCA     3456
Gln Ile Ser Val Val Glu Leu Lys Pro Asp His Ala Asn Val Pro Pro
           1140                1145                1150

TAC ACG CCG CCA GTG CCT GCA TTA AAG CCG TGT ATC TGG AAC TAT GCC     3504
Tyr Thr Pro Pro Val Pro Ala Leu Lys Pro Cys Ile Trp Asn Tyr Ala
       1155                1160                1165

GAT TTA GTT GAG TAC GCA GAA GGC GAT ATC GCC AAG GTA TTT GGC AGT     3552
Asp Leu Val Glu Tyr Ala Glu Gly Asp Ile Ala Lys Val Phe Gly Ser
   1170                1175                1180

GAT TAT GCC ATT ATC GAC AGC TAC TCG CGC CGC GTA CGT CTA CCG ACC     3600
Asp Tyr Ala Ile Ile Asp Ser Tyr Ser Arg Arg Val Arg Leu Pro Thr
1185               1190                1195                1200

ACT GAC TAC CTG TTG GTA TCG CGC GTG ACC AAA CTT GAT GCG ACC ATC     3648
```

-continued

```
Thr Asp Tyr Leu Leu Val Ser Arg Val Thr Lys Leu Asp Ala Thr Ile
                1205                1210                1215

AAT CAA TTT AAG CCA TGC TCA ATG ACC ACT GAG TAC GAC ATC CCT GTT      3696
Asn Gln Phe Lys Pro Cys Ser Met Thr Thr Glu Tyr Asp Ile Pro Val
            1220                1225                1230

GAT GCG CCG TAC TTA GTA GAC GGA CAA ATC CCT TGG GCG GTA GCA GTA      3744
Asp Ala Pro Tyr Leu Val Asp Gly Gln Ile Pro Trp Ala Val Ala Val
        1235                1240                1245

GAA TCA GGC CAA TGT GAC TTG ATG CTT ATT AGC TAT CTC GGT ATC GAC      3792
Glu Ser Gly Gln Cys Asp Leu Met Leu Ile Ser Tyr Leu Gly Ile Asp
    1250                1255                1260

TTT GAG AAC AAA GGC GAG CGG GTT TAT CGA CTA CTC GAT TGT ACC CTC      3840
Phe Glu Asn Lys Gly Glu Arg Val Tyr Arg Leu Leu Asp Cys Thr Leu
1265                1270                1275                1280

ACC TTC CTA GGC GAC TTG CCA CGT GGC GGA GAT ACC CTA CGT TAC GAC      3888
Thr Phe Leu Gly Asp Leu Pro Arg Gly Gly Asp Thr Leu Arg Tyr Asp
                1285                1290                1295

ATT AAG ATC AAT AAC TAT GCT CGC AAC GGC GAC ACC CTG CTG TTC TTC      3936
Ile Lys Ile Asn Asn Tyr Ala Arg Asn Gly Asp Thr Leu Leu Phe Phe
            1300                1305                1310

TTC TCG TAT GAG TGT TTT GTT GGC GAC AAG ATG ATC CTC AAG ATG GAT      3984
Phe Ser Tyr Glu Cys Phe Val Gly Asp Lys Met Ile Leu Lys Met Asp
        1315                1320                1325

GGC GGC TGC GCT GGC TTC TTC ACT GAT GAA GAG CTT GCC GAC GGT AAA      4032
Gly Gly Cys Ala Gly Phe Phe Thr Asp Glu Glu Leu Ala Asp Gly Lys
    1330                1335                1340

GGC GTG ATT CGC ACA GAA GAA GAG ATT AAA GCT CGC AGC CTA GTG CAA      4080
Gly Val Ile Arg Thr Glu Glu Glu Ile Lys Ala Arg Ser Leu Val Gln
1345                1350                1355                1360

AAG CAA CGC TTT AAT CCG TTA CTA GAT TGT CCT AAA ACC CAA TTT AGT      4128
Lys Gln Arg Phe Asn Pro Leu Leu Asp Cys Pro Lys Thr Gln Phe Ser
                1365                1370                1375

TAT GGT GAT ATT CAT AAG CTA TTA ACT GCT GAT ATT GAG GGT TGT TTT      4176
Tyr Gly Asp Ile His Lys Leu Leu Thr Ala Asp Ile Glu Gly Cys Phe
            1380                1385                1390

GGC CCA AGC CAC AGT GGC GTC CAC CAG CCG TCA CTT TGT TTC GCA TCT      4224
Gly Pro Ser His Ser Gly Val His Gln Pro Ser Leu Cys Phe Ala Ser
        1395                1400                1405

GAA AAA TTC TTG ATG ATT GAA CAA GTC AGC AAG GTT GAT CGC ACT GGC      4272
Glu Lys Phe Leu Met Ile Glu Gln Val Ser Lys Val Asp Arg Thr Gly
    1410                1415                1420

GGT ACT TGG GGA CTT GGC TTA ATT GAG GGT CAT AAG CAG CTT GAA GCA      4320
Gly Thr Trp Gly Leu Gly Leu Ile Glu Gly His Lys Gln Leu Glu Ala
1425                1430                1435                1440

GAC CAC TGG TAC TTC CCA TGT CAT TTC AAG GGC GAC CAA GTG ATG GCT      4368
Asp His Trp Tyr Phe Pro Cys His Phe Lys Gly Asp Gln Val Met Ala
                1445                1450                1455

GGC TCG CTA ATG GCT GAA GGT TGT GGC CAG TTA TTG CAG TTC TAT ATG      4416
Gly Ser Leu Met Ala Glu Gly Cys Gly Gln Leu Leu Gln Phe Tyr Met
            1460                1465                1470

CTG CAC CTT GGT ATG CAT ACC CAA ACT AAA AAT GGT CGT TTC CAA CCT      4464
Leu His Leu Gly Met His Thr Gln Thr Lys Asn Gly Arg Phe Gln Pro
        1475                1480                1485

CTT GAA AAC GCC TCA CAG CAA GTA CGC TGT CGC GGT CAA GTG CTG CCA      4512
Leu Glu Asn Ala Ser Gln Gln Val Arg Cys Arg Gly Gln Val Leu Pro
    1490                1495                1500

CAA TCA GGC GTG CTA ACT TAC CGT ATG GAA GTG ACT GAA ATC GGT TTC      4560
Gln Ser Gly Val Leu Thr Tyr Arg Met Glu Val Thr Glu Ile Gly Phe
1505                1510                1515                1520

AGT CCA CGC CCA TAT GCT AAA GCT AAC ATC GAT ATC TTG CTT AAT GGC      4608
```

```
Ser Pro Arg Pro Tyr Ala Lys Ala Asn Ile Asp Ile Leu Leu Asn Gly
                1525                1530                1535

AAA GCG GTA GTG GAT TTC CAA AAC CTA GGG GTG ATG ATA AAA GAG GAA    4656
Lys Ala Val Val Asp Phe Gln Asn Leu Gly Val Met Ile Lys Glu Glu
            1540                1545                1550

GAT GAG TGT ACT CGT TAT CCA CTT TTG ACT GAA TCA ACA ACG GCT AGC    4704
Asp Glu Cys Thr Arg Tyr Pro Leu Leu Thr Glu Ser Thr Thr Ala Ser
        1555                1560                1565

ACT GCA CAA GTA AAC GCT CAA ACA AGT GCG AAA AAG GTA TAC AAG CCA    4752
Thr Ala Gln Val Asn Ala Gln Thr Ser Ala Lys Lys Val Tyr Lys Pro
    1570                1575                1580

GCA TCA GTC AAT GCG CCA TTA ATG GCA CAA ATT CCT GAT CTG ACT AAA    4800
Ala Ser Val Asn Ala Pro Leu Met Ala Gln Ile Pro Asp Leu Thr Lys
1585                1590                1595                1600

GAG CCA AAC AAG GGC GTT ATT CCG ATT TCC CAT GTT GAA GCA CCA ATT    4848
Glu Pro Asn Lys Gly Val Ile Pro Ile Ser His Val Glu Ala Pro Ile
                1605                1610                1615

ACG CCA GAC TAC CCG AAC CGT GTA CCT GAT ACA GTG CCA TTC ACG CCG    4896
Thr Pro Asp Tyr Pro Asn Arg Val Pro Asp Thr Val Pro Phe Thr Pro
            1620                1625                1630

TAT CAC ATG TTT GAG TTT GCT ACA GGC AAT ATC GAA AAC TGT TTC GGG    4944
Tyr His Met Phe Glu Phe Ala Thr Gly Asn Ile Glu Asn Cys Phe Gly
        1635                1640                1645

CCA GAG TTC TCA ATC TAT CGC GGC ATG ATC CCA CCA CGT ACA CCA TGC    4992
Pro Glu Phe Ser Ile Tyr Arg Gly Met Ile Pro Pro Arg Thr Pro Cys
    1650                1655                1660

GGT GAC TTA CAA GTG ACC ACA CGT GTG ATT GAA GTT AAC GGT AAG CGT    5040
Gly Asp Leu Gln Val Thr Thr Arg Val Ile Glu Val Asn Gly Lys Arg
1665                1670                1675                1680

GGC GAC TTT AAA AAG CCA TCA TCG TGT ATC GCT GAA TAT GAA GTG CCT    5088
Gly Asp Phe Lys Lys Pro Ser Ser Cys Ile Ala Glu Tyr Glu Val Pro
                1685                1690                1695

GCA GAT GCG TGG TAT TTC GAT AAA AAC AGC CAC GGC GCA GTG ATG CCA    5136
Ala Asp Ala Trp Tyr Phe Asp Lys Asn Ser His Gly Ala Val Met Pro
            1700                1705                1710

TAT TCA ATT TTA ATG GAG ATC TCA CTG CAA CCT AAC GGC TTT ATC TCA    5184
Tyr Ser Ile Leu Met Glu Ile Ser Leu Gln Pro Asn Gly Phe Ile Ser
        1715                1720                1725

GGT TAC ATG GGC ACA ACC CTA GGC TTC CCT GGC CTT GAG CTG TTC TTC    5232
Gly Tyr Met Gly Thr Thr Leu Gly Phe Pro Gly Leu Glu Leu Phe Phe
    1730                1735                1740

CGT AAC TTA GAC GGT AGC GGT GAG TTA CTA CGT GAA GTA GAT TTA CGT    5280
Arg Asn Leu Asp Gly Ser Gly Glu Leu Leu Arg Glu Val Asp Leu Arg
1745                1750                1755                1760

GGT AAA ACC ATC CGT AAC GAC TCA CGT TTA TTA TCA ACA GTG ATG GCC    5328
Gly Lys Thr Ile Arg Asn Asp Ser Arg Leu Leu Ser Thr Val Met Ala
                1765                1770                1775

GGC ACT AAC ATC ATC CAA AGC TTT AGC TTC GAG CTA AGC ACT GAC GGT    5376
Gly Thr Asn Ile Ile Gln Ser Phe Ser Phe Glu Leu Ser Thr Asp Gly
            1780                1785                1790

GAG CCT TTC TAT CGC GGC ACT GCG GTA TTT GGC TAT TTT AAA GGT GAC    5424
Glu Pro Phe Tyr Arg Gly Thr Ala Val Phe Gly Tyr Phe Lys Gly Asp
        1795                1800                1805

GCA CTT AAA GAT CAG CTA GGC CTA GAT AAC GGT AAA GTC ACT CAG CCA    5472
Ala Leu Lys Asp Gln Leu Gly Leu Asp Asn Gly Lys Val Thr Gln Pro
    1810                1815                1820

TGG CAT GTA GCT AAC GGC GTT GCT GCA AGC ACT AAG GTG AAC CTG CTT    5520
Trp His Val Ala Asn Gly Val Ala Ala Ser Thr Lys Val Asn Leu Leu
1825                1830                1835                1840

GAT AAG AGC TGC CGT CAC TTT AAT GCG CCA GCT AAC CAG CCA CAC TAT    5568
```

-continued

Asp Lys Ser Cys Arg His Phe Asn Ala Pro Ala Asn Gln Pro His Tyr
1845 1850 1855

CGT CTA GCC GGT GGT CAG CTG AAC TTT ATC GAC AGT GTT GAA ATT GTT 5616
Arg Leu Ala Gly Gly Gln Leu Asn Phe Ile Asp Ser Val Glu Ile Val
1860 1865 1870

GAT AAT GGC GGC ACC GAA GGT TTA GGT TAC TTG TAT GCC GAG CGC ACC 5664
Asp Asn Gly Gly Thr Glu Gly Leu Gly Tyr Leu Tyr Ala Glu Arg Thr
1875 1880 1885

ATT GAC CCA AGT GAT TGG TTC TTC CAG TTC CAC TTC CAC CAA GAT CCG 5712
Ile Asp Pro Ser Asp Trp Phe Phe Gln Phe His Phe His Gln Asp Pro
1890 1895 1900

GTT ATG CCA GGC TCC TTA GGT GTT GAA GCA ATT ATT GAA ACC ATG CAA 5760
Val Met Pro Gly Ser Leu Gly Val Glu Ala Ile Ile Glu Thr Met Gln
1905 1910 1915 1920

GCT TAC GCT ATT AGT AAA GAC TTG GGC GCA GAT TTC AAA AAT CCT AAG 5808
Ala Tyr Ala Ile Ser Lys Asp Leu Gly Ala Asp Phe Lys Asn Pro Lys
1925 1930 1935

TTT GGT CAG ATT TTA TCG AAC ATC AAG TGG AAG TAT CGC GGT CAA ATC 5856
Phe Gly Gln Ile Leu Ser Asn Ile Lys Trp Lys Tyr Arg Gly Gln Ile
1940 1945 1950

AAT CCG CTG AAC AAG CAG ATG TCT ATG GAT GTC AGC ATT ACT TCA ATC 5904
Asn Pro Leu Asn Lys Gln Met Ser Met Asp Val Ser Ile Thr Ser Ile
1955 1960 1965

AAA GAT GAA GAC GGT AAG AAA GTC ATC ACA GGT AAT GCC AGC TTG AGT 5952
Lys Asp Glu Asp Gly Lys Lys Val Ile Thr Gly Asn Ala Ser Leu Ser
1970 1975 1980

AAA GAT GGT CTG CGC ATA TAC GAG GTC TTC GAT ATA GCT ATC AGC ATC 6000
Lys Asp Gly Leu Arg Ile Tyr Glu Val Phe Asp Ile Ala Ile Ser Ile
1985 1990 1995 2000

GAA GAA TCT GTA 6012
Glu Glu Ser Val ( 2 ) INFORMATION FOR SEQ ID NO:15:

( i ) SEQUENCE CHARACTERISTICS:
( A ) LENGTH: 2004 amino acids
( B ) TYPE: amino acid
( D ) TOPOLOGY: linear ( i i ) MOLECULE TYPE: protein ( x i ) SEQUENCE DESCRIPTION: SEQ ID NO:15:

Met Ser Leu Pro Asp Asn Ala Ser Asn His Leu Ser Ala Asn Gln Lys
1 5 10 15

Gly Ala Ser Gln Ala Ser Lys Thr Ser Lys Gln Ser Lys Ile Ala Ile
20 25 30

Val Gly Leu Ala Thr Leu Tyr Pro Asp Ala Lys Thr Pro Gln Glu Phe
35 40 45

Trp Gln Asn Leu Leu Asp Lys Arg Asp Ser Arg Ser Thr Leu Thr Asn
50 55 60

Glu Lys Leu Gly Ala Asn Ser Gln Asp Tyr Gln Gly Val Gln Gly Gln
65 70 75 80

Ser Asp Arg Phe Tyr Cys Asn Lys Gly Gly Tyr Ile Glu Asn Phe Ser
85 90 95

Phe Asn Ala Ala Gly Tyr Lys Leu Pro Glu Gln Ser Leu Asn Gly Leu
100 105 110

Asp Asp Ser Phe Leu Trp Ala Leu Asp Thr Ser Arg Asn Ala Leu Ile
115 120 125

Asp Ala Gly Ile Asp Ile Asn Gly Ala Asp Leu Ser Arg Ala Gly Val
130 135 140

```
Val Met Gly Ala Leu Ser Phe Pro Thr Thr Arg Ser Asn Asp Leu Phe
145                 150                 155                 160

Leu Pro Ile Tyr His Ser Ala Val Glu Lys Ala Leu Gln Asp Lys Leu
                165                 170                 175

Gly Val Lys Ala Phe Lys Leu Ser Pro Thr Asn Ala His Thr Ala Arg
            180                 185                 190

Ala Ala Asn Glu Ser Ser Leu Asn Ala Ala Asn Gly Ala Ile Ala His
        195                 200                 205

Asn Ser Ser Lys Val Val Ala Asp Ala Leu Gly Leu Gly Gly Ala Gln
    210                 215                 220

Leu Ser Leu Asp Ala Ala Cys Ala Ser Ser Val Tyr Ser Leu Lys Leu
225                 230                 235                 240

Ala Cys Asp Tyr Leu Ser Thr Gly Lys Ala Asp Ile Met Leu Ala Gly
                245                 250                 255

Ala Val Ser Gly Ala Asp Pro Phe Phe Ile Asn Met Gly Phe Ser Ile
            260                 265                 270

Phe His Ala Tyr Pro Asp His Gly Ile Ser Val Pro Phe Asp Ala Ser
        275                 280                 285

Ser Lys Gly Leu Phe Ala Gly Glu Gly Ala Gly Val Leu Val Leu Lys
    290                 295                 300

Arg Leu Glu Asp Ala Glu Arg Asp Asn Asp Lys Ile Tyr Ala Val Val
305                 310                 315                 320

Ser Gly Val Gly Leu Ser Asn Asp Gly Lys Gly Gln Phe Val Leu Ser
                325                 330                 335

Pro Asn Pro Lys Gly Gln Val Lys Ala Phe Glu Arg Ala Tyr Ala Ala
            340                 345                 350

Ser Asp Ile Glu Pro Lys Asp Ile Glu Val Ile Glu Cys His Ala Thr
        355                 360                 365

Gly Thr Pro Leu Gly Asp Lys Ile Glu Leu Thr Ser Met Glu Thr Phe
    370                 375                 380

Phe Glu Asp Lys Leu Gln Gly Thr Asp Ala Pro Leu Ile Gly Ser Ala
385                 390                 395                 400

Lys Ser Asn Leu Gly His Leu Leu Thr Ala Ala His Ala Gly Ile Met
                405                 410                 415

Lys Met Ile Phe Ala Met Lys Glu Gly Tyr Leu Pro Pro Ser Ile Asn
            420                 425                 430

Ile Ser Asp Ala Ile Ala Ser Pro Lys Lys Leu Phe Gly Lys Pro Thr
        435                 440                 445

Leu Pro Ser Met Val Gln Gly Trp Pro Asp Lys Pro Ser Asn Asn His
    450                 455                 460

Phe Gly Val Arg Thr Arg His Ala Gly Val Ser Val Phe Gly Phe Gly
465                 470                 475                 480

Gly Cys Asn Ala His Leu Leu Leu Glu Ser Tyr Asn Gly Lys Gly Thr
                485                 490                 495

Val Lys Ala Glu Ala Thr Gln Val Pro Arg Gln Ala Glu Pro Leu Lys
            500                 505                 510

Val Val Gly Leu Ala Ser His Phe Gly Pro Leu Ser Ser Ile Asn Ala
        515                 520                 525

Leu Asn Asn Ala Val Thr Gln Asp Gly Asn Gly Phe Ile Glu Leu Pro
    530                 535                 540

Lys Lys Arg Trp Lys Gly Leu Glu Lys His Ser Glu Leu Leu Ala Glu
545                 550                 555                 560

Phe Gly Leu Ala Ser Ala Pro Lys Gly Ala Tyr Val Asp Asn Phe Glu
```

-continued

```
                565                 570                 575

Leu Asp Phe Leu Arg Phe Lys Leu Pro Pro Asn Glu Asp Asp Arg Leu
            580                 585                 590

Ile Ser Gln Gln Leu Met Leu Met Arg Val Thr Asp Glu Ala Ile Arg
        595                 600                 605

Asp Ala Lys Leu Glu Pro Gly Gln Lys Val Ala Val Leu Val Ala Met
    610                 615                 620

Glu Thr Glu Leu Glu Leu His Gln Phe Arg Gly Arg Val Asn Leu His
625                 630                 635                 640

Thr Gln Leu Ala Gln Ser Leu Ala Ala Met Gly Val Ser Leu Ser Thr
                645                 650                 655

Asp Glu Tyr Gln Ala Leu Glu Ala Ile Ala Met Asp Ser Val Leu Asp
            660                 665                 670

Ala Ala Lys Leu Asn Gln Tyr Thr Ser Phe Ile Gly Asn Ile Met Ala
        675                 680                 685

Ser Arg Val Ala Ser Leu Trp Asp Phe Asn Gly Pro Ala Phe Thr Ile
    690                 695                 700

Ser Ala Ala Glu Gln Ser Val Ser Arg Cys Ile Asp Val Ala Gln Asn
705                 710                 715                 720

Leu Ile Met Glu Asp Asn Leu Asp Ala Val Val Ile Ala Ala Val Asp
                725                 730                 735

Leu Ser Gly Ser Phe Glu Gln Val Ile Leu Lys Asn Ala Ile Ala Pro
            740                 745                 750

Val Ala Ile Glu Pro Asn Leu Glu Ala Ser Leu Asn Pro Thr Ser Ala
        755                 760                 765

Ser Trp Asn Val Gly Glu Gly Ala Gly Ala Val Val Leu Val Lys Asn
    770                 775                 780

Glu Ala Thr Ser Gly Cys Ser Tyr Gly Gln Ile Asp Ala Leu Gly Phe
785                 790                 795                 800

Ala Lys Thr Ala Glu Thr Ala Leu Ala Thr Asp Lys Leu Leu Ser Gln
                805                 810                 815

Thr Ala Thr Asp Phe Asn Lys Val Lys Val Ile Glu Thr Met Ala Ala
            820                 825                 830

Pro Ala Ser Gln Ile Gln Leu Ala Pro Ile Val Ser Ser Gln Val Thr
        835                 840                 845

His Thr Ala Ala Glu Gln Arg Val Gly His Cys Phe Ala Ala Ala Gly
    850                 855                 860

Met Ala Ser Leu Leu His Gly Leu Leu Asn Leu Asn Thr Val Ala Gln
865                 870                 875                 880

Thr Asn Lys Ala Asn Cys Ala Leu Ile Asn Asn Ile Ser Glu Asn Gln
                885                 890                 895

Leu Ser Gln Leu Leu Ile Ser Gln Thr Ala Ser Glu Gln Gln Ala Leu
            900                 905                 910

Thr Ala Arg Leu Ser Asn Glu Leu Lys Ser Asp Ala Lys His Gln Leu
        915                 920                 925

Val Lys Gln Val Thr Leu Gly Gly Arg Asp Ile Tyr Gln His Ile Val
    930                 935                 940

Asp Thr Pro Leu Ala Ser Leu Glu Ser Ile Thr Gln Lys Leu Ala Gln
945                 950                 955                 960

Ala Thr Ala Ser Thr Val Val Asn Gln Val Lys Pro Ile Lys Ala Ala
                965                 970                 975

Gly Ser Val Glu Met Ala Asn Ser Phe Glu Thr Glu Ser Ser Ala Glu
            980                 985                 990
```

-continued

```
Pro Gln Ile Thr Ile Ala Ala Gln Gln Thr Ala Asn Ile Gly Val Thr
        995                1000                1005

Ala Gln Ala Thr Lys Arg Glu Leu Gly Thr Pro Pro Met Thr Thr Asn
    1010                1015                1020

Thr Ile Ala Asn Thr Ala Asn Asn Leu Asp Lys Thr Leu Glu Thr Val
1025                1030                1035                1040

Ala Gly Asn Thr Val Ala Ser Lys Val Gly Ser Gly Asp Ile Val Asn
                1045                1050                1055

Phe Gln Gln Asn Gln Gln Leu Ala Gln Gln Ala His Leu Ala Phe Leu
            1060                1065                1070

Glu Ser Arg Ser Ala Gly Met Lys Val Ala Asp Ala Leu Leu Lys Gln
        1075                1080                1085

Gln Leu Ala Gln Val Thr Gly Gln Thr Ile Asp Asn Gln Ala Leu Asp
    1090                1095                1100

Thr Gln Ala Val Asp Thr Gln Thr Ser Glu Asn Val Ala Ile Ala Ala
1105                1110                1115                1120

Glu Ser Pro Val Gln Val Thr Thr Pro Val Gln Val Thr Thr Pro Val
                1125                1130                1135

Gln Ile Ser Val Val Glu Leu Lys Pro Asp His Ala Asn Val Pro Pro
            1140                1145                1150

Tyr Thr Pro Pro Val Pro Ala Leu Lys Pro Cys Ile Trp Asn Tyr Ala
        1155                1160                1165

Asp Leu Val Glu Tyr Ala Glu Gly Asp Ile Ala Lys Val Phe Gly Ser
    1170                1175                1180

Asp Tyr Ala Ile Ile Asp Ser Tyr Ser Arg Arg Val Arg Leu Pro Thr
1185                1190                1195                1200

Thr Asp Tyr Leu Leu Val Ser Arg Val Thr Lys Leu Asp Ala Thr Ile
                1205                1210                1215

Asn Gln Phe Lys Pro Cys Ser Met Thr Thr Glu Tyr Asp Ile Pro Val
            1220                1225                1230

Asp Ala Pro Tyr Leu Val Asp Gly Gln Ile Pro Trp Ala Val Ala Val
        1235                1240                1245

Glu Ser Gly Gln Cys Asp Leu Met Leu Ile Ser Tyr Leu Gly Ile Asp
    1250                1255                1260

Phe Glu Asn Lys Gly Glu Arg Val Tyr Arg Leu Leu Asp Cys Thr Leu
1265                1270                1275                1280

Thr Phe Leu Gly Asp Leu Pro Arg Gly Gly Asp Thr Leu Arg Tyr Asp
                1285                1290                1295

Ile Lys Ile Asn Asn Tyr Ala Arg Asn Gly Asp Thr Leu Leu Phe Phe
            1300                1305                1310

Phe Ser Tyr Glu Cys Phe Val Gly Asp Lys Met Ile Leu Lys Met Asp
        1315                1320                1325

Gly Gly Cys Ala Gly Phe Phe Thr Asp Glu Glu Leu Ala Asp Gly Lys
    1330                1335                1340

Gly Val Ile Arg Thr Glu Glu Glu Ile Lys Ala Arg Ser Leu Val Gln
1345                1350                1355                1360

Lys Gln Arg Phe Asn Pro Leu Leu Asp Cys Pro Lys Thr Gln Phe Ser
                1365                1370                1375

Tyr Gly Asp Ile His Lys Leu Leu Thr Ala Asp Ile Glu Gly Cys Phe
            1380                1385                1390

Gly Pro Ser His Ser Gly Val His Gln Pro Ser Leu Cys Phe Ala Ser
        1395                1400                1405

Glu Lys Phe Leu Met Ile Glu Gln Val Ser Lys Val Asp Arg Thr Gly
    1410                1415                1420
```

```
Gly Thr Trp Gly Leu Gly Leu Ile Glu Gly His Lys Gln Leu Glu Ala
1425                1430                1435                1440

Asp His Trp Tyr Phe Pro Cys His Phe Lys Gly Asp Gln Val Met Ala
                1445                1450                1455

Gly Ser Leu Met Ala Glu Gly Cys Gly Gln Leu Leu Gln Phe Tyr Met
            1460                1465                1470

Leu His Leu Gly Met His Thr Gln Thr Lys Asn Gly Arg Phe Gln Pro
        1475                1480                1485

Leu Glu Asn Ala Ser Gln Gln Val Arg Cys Arg Gly Gln Val Leu Pro
    1490                1495                1500

Gln Ser Gly Val Leu Thr Tyr Arg Met Glu Val Thr Glu Ile Gly Phe
1505                1510                1515                1520

Ser Pro Arg Pro Tyr Ala Lys Ala Asn Ile Asp Ile Leu Leu Asn Gly
                1525                1530                1535

Lys Ala Val Val Asp Phe Gln Asn Leu Gly Val Met Ile Lys Glu Glu
            1540                1545                1550

Asp Glu Cys Thr Arg Tyr Pro Leu Leu Thr Glu Ser Thr Thr Ala Ser
        1555                1560                1565

Thr Ala Gln Val Asn Ala Gln Thr Ser Ala Lys Lys Val Tyr Lys Pro
    1570                1575                1580

Ala Ser Val Asn Ala Pro Leu Met Ala Gln Ile Pro Asp Leu Thr Lys
1585                1590                1595                1600

Glu Pro Asn Lys Gly Val Ile Pro Ile Ser His Val Glu Ala Pro Ile
                1605                1610                1615

Thr Pro Asp Tyr Pro Asn Arg Val Pro Asp Thr Val Pro Phe Thr Pro
            1620                1625                1630

Tyr His Met Phe Glu Phe Ala Thr Gly Asn Ile Glu Asn Cys Phe Gly
        1635                1640                1645

Pro Glu Phe Ser Ile Tyr Arg Gly Met Ile Pro Pro Arg Thr Pro Cys
    1650                1655                1660

Gly Asp Leu Gln Val Thr Thr Arg Val Ile Glu Val Asn Gly Lys Arg
1665                1670                1675                1680

Gly Asp Phe Lys Lys Pro Ser Ser Cys Ile Ala Glu Tyr Glu Val Pro
                1685                1690                1695

Ala Asp Ala Trp Tyr Phe Asp Lys Asn Ser His Gly Ala Val Met Pro
            1700                1705                1710

Tyr Ser Ile Leu Met Glu Ile Ser Leu Gln Pro Asn Gly Phe Ile Ser
        1715                1720                1725

Gly Tyr Met Gly Thr Thr Leu Gly Phe Pro Gly Leu Glu Leu Phe Phe
    1730                1735                1740

Arg Asn Leu Asp Gly Ser Gly Glu Leu Leu Arg Glu Val Asp Leu Arg
1745                1750                1755                1760

Gly Lys Thr Ile Arg Asn Asp Ser Arg Leu Leu Ser Thr Val Met Ala
                1765                1770                1775

Gly Thr Asn Ile Ile Gln Ser Phe Ser Phe Glu Leu Ser Thr Asp Gly
            1780                1785                1790

Glu Pro Phe Tyr Arg Gly Thr Ala Val Phe Gly Tyr Phe Lys Gly Asp
        1795                1800                1805

Ala Leu Lys Asp Gln Leu Gly Leu Asp Asn Gly Lys Val Thr Gln Pro
    1810                1815                1820

Trp His Val Ala Asn Gly Val Ala Ala Ser Thr Lys Val Asn Leu Leu
1825                1830                1835                1840

Asp Lys Ser Cys Arg His Phe Asn Ala Pro Ala Asn Gln Pro His Tyr
```

```
                        1845                            1850                            1855

Arg Leu Ala Gly Gly Gln Leu Asn Phe Ile Asp Ser Val Glu Ile Val
                1860                            1865                            1870

Asp Asn Gly Gly Thr Glu Gly Leu Gly Tyr Leu Tyr Ala Glu Arg Thr
        1875                            1880                            1885

Ile Asp Pro Ser Asp Trp Phe Phe Gln Phe His Phe His Gln Asp Pro
    1890                            1895                            1900

Val Met Pro Gly Ser Leu Gly Val Glu Ala Ile Ile Glu Thr Met Gln
1905                            1910                            1915                            1920

Ala Tyr Ala Ile Ser Lys Asp Leu Gly Ala Asp Phe Lys Asn Pro Lys
                        1925                            1930                            1935

Phe Gly Gln Ile Leu Ser Asn Ile Lys Trp Lys Tyr Arg Gly Gln Ile
                1940                            1945                            1950

Asn Pro Leu Asn Lys Gln Met Ser Met Asp Val Ser Ile Thr Ser Ile
        1955                            1960                            1965

Lys Asp Glu Asp Gly Lys Lys Val Ile Thr Gly Asn Ala Ser Leu Ser
    1970                            1975                            1980

Lys Asp Gly Leu Arg Ile Tyr Glu Val Phe Asp Ile Ala Ile Ser Ile
1985                            1990                            1995                            2000

Glu Glu Ser Val
```

( 2 ) INFORMATION FOR SEQ ID NO:16:

( i ) SEQUENCE CHARACTERISTICS:
( A ) LENGTH: 1629 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( A ) ORGANISM: Shewanella putrefaciens SCRC-2874 (FERM BP- 1625)

( i x ) FEATURE:
( A ) NAME/KEY: CDS
( B ) LOCATION: 1..1629

( i x ) FEATURE:
( A ) NAME/KEY: mat_peptide
( B ) LOCATION: 1..1629

( x i ) SEQUENCE DESCRIPTION: SEQ ID NO:16:

```
ATG AAT CCT ACA GCA ACT AAC GAA ATG CTT TCT CCG TGG CCA TGG GCT       48
Met Asn Pro Thr Ala Thr Asn Glu Met Leu Ser Pro Trp Pro Trp Ala
  1               5                  10                  15

GTG ACA GAG TCA AAT ATC AGT TTT GAC GTG CAA GTG ATG GAA CAA CAA       96
Val Thr Glu Ser Asn Ile Ser Phe Asp Val Gln Val Met Glu Gln Gln
            20                  25                  30

CTT AAA GAT TTT AGC CGG GCA TGT TAC GTG GTC AAT CAT GCC GAC CAC      144
Leu Lys Asp Phe Ser Arg Ala Cys Tyr Val Val Asn His Ala Asp His
        35                  40                  45

GGC TTT GGT ATT GCG CAA ACT GCC GAT ATC GTG ACT GAA CAA GCG GCA      192
Gly Phe Gly Ile Ala Gln Thr Ala Asp Ile Val Thr Glu Gln Ala Ala
    50                  55                  60

AAC AGC ACA GAT TTA CCT GTT AGT GCT TTT ACT CCT GCA TTA GGT ACC      240
Asn Ser Thr Asp Leu Pro Val Ser Ala Phe Thr Pro Ala Leu Gly Thr
 65                  70                  75                  80

GAA AGC CTA GGC GAC AAT AAT TTC CGC CGC GTT CAC GGC GTT AAA TAC      288
Glu Ser Leu Gly Asp Asn Asn Phe Arg Arg Val His Gly Val Lys Tyr
                 85                  90                  95
```

-continued

```
GCT TAT TAC GCA GGC GCT ATG GCA AAC GGT ATT TCA TCT GAA GAG CTA          336
Ala Tyr Tyr Ala Gly Ala Met Ala Asn Gly Ile Ser Ser Glu Glu Leu
            100                 105                 110

GTG ATT GCC CTA GGT CAA GCT GGC ATT TTG TGT GGT TCG TTT GGA GCA          384
Val Ile Ala Leu Gly Gln Ala Gly Ile Leu Cys Gly Ser Phe Gly Ala
        115                 120                 125

GCC GGT CTT ATT CCA AGT CGC GTT GAA GCG GCA ATT AAC CGT ATT CAA          432
Ala Gly Leu Ile Pro Ser Arg Val Glu Ala Ala Ile Asn Arg Ile Gln
    130                 135                 140

GCA GCG CTG CCA AAT GGC CCT TAT ATG TTT AAC CTT ATC CAT AGT CCT          480
Ala Ala Leu Pro Asn Gly Pro Tyr Met Phe Asn Leu Ile His Ser Pro
145                 150                 155                 160

AGC GAG CCA GCA TTA GAG CGT GGC AGC GTA GAG CTA TTT TTA AAG CAT          528
Ser Glu Pro Ala Leu Glu Arg Gly Ser Val Glu Leu Phe Leu Lys His
                165                 170                 175

AAG GTA CGC ACC GTT GAA GCA TCA GCT TTC TTA GGT CTA ACA CCA CAA          576
Lys Val Arg Thr Val Glu Ala Ser Ala Phe Leu Gly Leu Thr Pro Gln
            180                 185                 190

ATC GTC TAT TAC CGT GCA GCA GGA TTG AGC CGA GAC GCA CAA GGT AAA          624
Ile Val Tyr Tyr Arg Ala Ala Gly Leu Ser Arg Asp Ala Gln Gly Lys
        195                 200                 205

GTT GTG GTT GGT AAC AAG GTT ATC GCT AAA GTA AGT CGC ACC GAA GTG          672
Val Val Val Gly Asn Lys Val Ile Ala Lys Val Ser Arg Thr Glu Val
    210                 215                 220

GCT GAA AAG TTT ATG ATG CCA GCG CCC GCA AAA ATG CTA CAA AAA CTA          720
Ala Glu Lys Phe Met Met Pro Ala Pro Ala Lys Met Leu Gln Lys Leu
225                 230                 235                 240

GTT GAT GAC GGT TCA ATT ACC GCT GAG CAA ATG GAG CTG GCG CAA CTT          768
Val Asp Asp Gly Ser Ile Thr Ala Glu Gln Met Glu Leu Ala Gln Leu
                245                 250                 255

GTA CCT ATG GCT GAC GAC ATC ACT GCA GAG GCC GAT TCA GGT GGC CAT          816
Val Pro Met Ala Asp Asp Ile Thr Ala Glu Ala Asp Ser Gly Gly His
            260                 265                 270

ACT GAT AAC CGT CCA TTA GTA ACA TTG CTG CCA ACC ATT TTA GCG CTG          864
Thr Asp Asn Arg Pro Leu Val Thr Leu Leu Pro Thr Ile Leu Ala Leu
        275                 280                 285

AAA GAA GAA ATT CAA GCT AAA TAC CAA TAC GAC ACT CCT ATT CGT GTC          912
Lys Glu Glu Ile Gln Ala Lys Tyr Gln Tyr Asp Thr Pro Ile Arg Val
    290                 295                 300

GGT TGT GGT GGC GGT GTG GGT ACG CCT GAT GCA GCG CTG GCA ACG TTT          960
Gly Cys Gly Gly Gly Val Gly Thr Pro Asp Ala Ala Leu Ala Thr Phe
305                 310                 315                 320

AAC ATG GGC GCG GCG TAT ATT GTT ACC GGC TCT ATC AAC CAA GCT TGT         1008
Asn Met Gly Ala Ala Tyr Ile Val Thr Gly Ser Ile Asn Gln Ala Cys
                325                 330                 335

GTT GAA GCG GGC GCA AGT GAT CAC ACT CGT AAA TTA CTT GCC ACC ACT         1056
Val Glu Ala Gly Ala Ser Asp His Thr Arg Lys Leu Leu Ala Thr Thr
            340                 345                 350

GAA ATG GCC GAT GTG ACT ATG GCA CCA GCT GCA GAT ATG TTC GAG ATG         1104
Glu Met Ala Asp Val Thr Met Ala Pro Ala Ala Asp Met Phe Glu Met
        355                 360                 365

GGC GTA AAA CTG CAG GTG GTT AAG CGC GGC ACG CTA TTC CCA ATG CGC         1152
Gly Val Lys Leu Gln Val Val Lys Arg Gly Thr Leu Phe Pro Met Arg
    370                 375                 380

GCT AAC AAG CTA TAT GAG ATC TAC ACC CGT TAC GAT TCA ATC GAA GCG         1200
Ala Asn Lys Leu Tyr Glu Ile Tyr Thr Arg Tyr Asp Ser Ile Glu Ala
385                 390                 395                 400

ATC CCA TTA GAC GAG CGT GAA AAG CTT GAG AAA CAA GTA TTC CGC TCA         1248
Ile Pro Leu Asp Glu Arg Glu Lys Leu Glu Lys Gln Val Phe Arg Ser
                405                 410                 415
```

-continued

```
AGC CTA GAT GAA ATA TGG GCA GGT ACA GTG GCG CAC TTT AAC GAG CGC      1296
Ser Leu Asp Glu Ile Trp Ala Gly Thr Val Ala His Phe Asn Glu Arg
            420                 425                 430

GAC CCT AAG CAA ATC GAA CGC GCA GAG GGT AAC CCT AAG CGT AAA ATG      1344
Asp Pro Lys Gln Ile Glu Arg Ala Glu Gly Asn Pro Lys Arg Lys Met
        435                 440                 445

GCA TTG ATT TTC CGT TGG TAC TTA GGT CTT TCT AGT CGC TGG TCA AAC      1392
Ala Leu Ile Phe Arg Trp Tyr Leu Gly Leu Ser Ser Arg Trp Ser Asn
    450                 455                 460

TCA GGC GAA GTG GGT CGT GAA ATG GAT TAT CAA ATT TGG GCT GGC CCT      1440
Ser Gly Glu Val Gly Arg Glu Met Asp Tyr Gln Ile Trp Ala Gly Pro
465                 470                 475                 480

GCT CTC GGT GCA TTT AAC CAA TGG GCA AAA GGC AGT TAC TTA GAT AAC      1488
Ala Leu Gly Ala Phe Asn Gln Trp Ala Lys Gly Ser Tyr Leu Asp Asn
                485                 490                 495

TAT CAA GAC CGA AAT GCC GTC GAT TTG GCA AAG CAC TTA ATG TAC GGC      1536
Tyr Gln Asp Arg Asn Ala Val Asp Leu Ala Lys His Leu Met Tyr Gly
            500                 505                 510

GCG GCT TAC TTA AAT CGT ATT AAC TCG CTA ACG GCT CAA GGC GTT AAA      1584
Ala Ala Tyr Leu Asn Arg Ile Asn Ser Leu Thr Ala Gln Gly Val Lys
        515                 520                 525

GTG CCA GCA CAG TTA CTT CGC TGG AAG CCA AAC CAA AGA ATG GCC          1629
Val Pro Ala Gln Leu Leu Arg Trp Lys Pro Asn Gln Arg Met Ala
    530                 535                 540
```

( 2 ) INFORMATION FOR SEQ ID NO:17:

( i ) SEQUENCE CHARACTERISTICS:
( A ) LENGTH: 543 amino acids
( B ) TYPE: amino acid
( D ) TOPOLOGY: linear ( i i ) MOLECULE TYPE: protein ( x i ) SEQUENCE DESCRIPTION: SEQ ID NO:17:

```
Met Asn Pro Thr Ala Thr Asn Glu Met Leu Ser Pro Trp Pro Trp Ala
1               5                   10                  15

Val Thr Glu Ser Asn Ile Ser Phe Asp Val Gln Val Met Glu Gln Gln
            20                  25                  30

Leu Lys Asp Phe Ser Arg Ala Cys Tyr Val Val Asn His Ala Asp His
        35                  40                  45

Gly Phe Gly Ile Ala Gln Thr Ala Asp Ile Val Thr Glu Gln Ala Ala
    50                  55                  60

Asn Ser Thr Asp Leu Pro Val Ser Ala Phe Thr Pro Ala Leu Gly Thr
65                  70                  75                  80

Glu Ser Leu Gly Asp Asn Asn Phe Arg Arg Val His Gly Val Lys Tyr
                85                  90                  95

Ala Tyr Tyr Ala Gly Ala Met Ala Asn Gly Ile Ser Ser Glu Glu Leu
            100                 105                 110

Val Ile Ala Leu Gly Gln Ala Gly Ile Leu Cys Gly Ser Phe Gly Ala
        115                 120                 125

Ala Gly Leu Ile Pro Ser Arg Val Glu Ala Ala Ile Asn Arg Ile Gln
    130                 135                 140

Ala Ala Leu Pro Asn Gly Pro Tyr Met Phe Asn Leu Ile His Ser Pro
145                 150                 155                 160

Ser Glu Pro Ala Leu Glu Arg Gly Ser Val Glu Leu Phe Leu Lys His
                165                 170                 175

Lys Val Arg Thr Val Glu Ala Ser Ala Phe Leu Gly Leu Thr Pro Gln
            180                 185                 190
```

-continued

Ile Val Tyr Tyr Arg Ala Ala Gly Leu Ser Arg Asp Ala Gln Gly Lys
195 200 205

Val Val Val Gly Asn Lys Val Ile Ala Lys Val Ser Arg Thr Glu Val
210 215 220

Ala Glu Lys Phe Met Met Pro Ala Pro Ala Lys Met Leu Gln Lys Leu
225 230 235 240

Val Asp Asp Gly Ser Ile Thr Ala Glu Gln Met Glu Leu Ala Gln Leu
245 250 255

Val Pro Met Ala Asp Asp Ile Thr Ala Glu Ala Asp Ser Gly Gly His
260 265 270

Thr Asp Asn Arg Pro Leu Val Thr Leu Leu Pro Thr Ile Leu Ala Leu
275 280 285

Lys Glu Glu Ile Gln Ala Lys Tyr Gln Tyr Asp Thr Pro Ile Arg Val
290 295 300

Gly Cys Gly Gly Gly Val Gly Thr Pro Asp Ala Ala Leu Ala Thr Phe
305 310 315 320

Asn Met Gly Ala Ala Tyr Ile Val Thr Gly Ser Ile Asn Gln Ala Cys
325 330 335

Val Glu Ala Gly Ala Ser Asp His Thr Arg Lys Leu Leu Ala Thr Thr
340 345 350

Glu Met Ala Asp Val Thr Met Ala Pro Ala Ala Asp Met Phe Glu Met
355 360 365

Gly Val Lys Leu Gln Val Val Lys Arg Gly Thr Leu Phe Pro Met Arg
370 375 380

Ala Asn Lys Leu Tyr Glu Ile Tyr Thr Arg Tyr Asp Ser Ile Glu Ala
385 390 395 400

Ile Pro Leu Asp Glu Arg Glu Lys Leu Glu Lys Gln Val Phe Arg Ser
405 410 415

Ser Leu Asp Glu Ile Trp Ala Gly Thr Val Ala His Phe Asn Glu Arg
420 425 430

Asp Pro Lys Gln Ile Glu Arg Ala Glu Gly Asn Pro Lys Arg Lys Met
435 440 445

Ala Leu Ile Phe Arg Trp Tyr Leu Gly Leu Ser Ser Arg Trp Ser Asn
450 455 460

Ser Gly Glu Val Gly Arg Glu Met Asp Tyr Gln Ile Trp Ala Gly Pro
465 470 475 480

Ala Leu Gly Ala Phe Asn Gln Trp Ala Lys Gly Ser Tyr Leu Asp Asn
485 490 495

Tyr Gln Asp Arg Asn Ala Val Asp Leu Ala Lys His Leu Met Tyr Gly
500 505 510

Ala Ala Tyr Leu Asn Arg Ile Asn Ser Leu Thr Ala Gln Gly Val Lys
515 520 525

Val Pro Ala Gln Leu Leu Arg Trp Lys Pro Asn Gln Arg Met Ala
530 535 540

( 2 ) INFORMATION FOR SEQ ID NO:18:

( i ) SEQUENCE CHARACTERISTICS:
( A ) LENGTH: 1575 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( A ) ORGANISM: Shewanella putrefaciens SCRC-2874 (FERM BP- 1625)

( i x ) FEATURE:
( A ) NAME/KEY: CDS
( B ) LOCATION: 1..1575

( i x ) FEATURE:
( A ) NAME/KEY: mat_peptide
( B ) LOCATION: 1..1575

( x i ) SEQUENCE DESCRIPTION: SEQ ID NO:18:

```
GTG CAA CTA CCA TTA ATT GAG GCC TCA TTA GTT AAA TTA TCT GAG CAA      48
Val Gln Leu Pro Leu Ile Glu Ala Ser Leu Val Lys Leu Ser Glu Gln
  1               5                  10                  15

GAG CTC ACC TCT TTA AAT TAC GCT TTT CAG CAA ATG AGA AAG CCA CTA      96
Glu Leu Thr Ser Leu Asn Tyr Ala Phe Gln Gln Met Arg Lys Pro Leu
             20                  25                  30

CAA ACC ATT AAT TAC GAC TAT GCG GTG TGG GAC AGA ACC TAC AGC TAT     144
Gln Thr Ile Asn Tyr Asp Tyr Ala Val Trp Asp Arg Thr Tyr Ser Tyr
         35                  40                  45

ATG AAA TCA AAC TCA GCG AGC GCT AAA AGG TAC TAT GAA AAA CAT GAG     192
Met Lys Ser Asn Ser Ala Ser Ala Lys Arg Tyr Tyr Glu Lys His Glu
     50                  55                  60

TAC CCA GAT GAT ACG TTC AAG AGT TTA AAA GTC GAC GGA GTA TTT ATA     240
Tyr Pro Asp Asp Thr Phe Lys Ser Leu Lys Val Asp Gly Val Phe Ile
 65                  70                  75                  80

TTC AAC CGT ACA AAT CAG CCA GTT TTT AGT AAA GGT TTT AAT CAT AGA     288
Phe Asn Arg Thr Asn Gln Pro Val Phe Ser Lys Gly Phe Asn His Arg
                 85                  90                  95

AAT GAT ATA CCG CTG GTC TTT GAA TTA ACT GAC TTT AAA CAA CAT CCA     336
Asn Asp Ile Pro Leu Val Phe Glu Leu Thr Asp Phe Lys Gln His Pro
            100                 105                 110

CAA AAC ATC GCA TTA TCT CCA CAA ACC AAA CAG GCA CAC CCA CCG GCA     384
Gln Asn Ile Ala Leu Ser Pro Gln Thr Lys Gln Ala His Pro Pro Ala
        115                 120                 125

AGT AAG CCG TTA GAC TCC CCT GAT GAT GTG CCT TCT ACC CAT GGG GTT     432
Ser Lys Pro Leu Asp Ser Pro Asp Asp Val Pro Ser Thr His Gly Val
    130                 135                 140

ATC GCC ACA CGA TAC GGT CCA GCA ATT TAT AGC TCT ACC AGC ATT TTA     480
Ile Ala Thr Arg Tyr Gly Pro Ala Ile Tyr Ser Ser Thr Ser Ile Leu
145                 150                 155                 160

AAA TCT GAT CGT AGC GGC TCC CAA CTT GGT TAT TTA GTC TTC ATT AGG     528
Lys Ser Asp Arg Ser Gly Ser Gln Leu Gly Tyr Leu Val Phe Ile Arg
                165                 170                 175

TTA ATT GAT GAA TGG TTC ATC GCT GAG CTA TCG CAA TAC ACT GCC GCA     576
Leu Ile Asp Glu Trp Phe Ile Ala Glu Leu Ser Gln Tyr Thr Ala Ala
            180                 185                 190

GGT GTT GAA ATC GCT ATG GCT GAT GCC GCA GAC GCA CAA TTA GCG AGA     624
Gly Val Glu Ile Ala Met Ala Asp Ala Ala Asp Ala Gln Leu Ala Arg
        195                 200                 205

TTA GGC GCA AAC ACT AAG CTT AAT AAA GTA ACC GCT ACA TCC GAA CGG     672
Leu Gly Ala Asn Thr Lys Leu Asn Lys Val Thr Ala Thr Ser Glu Arg
    210                 215                 220

TTA ATA ACT AAT GTC GAT GGT AAG CCT CTG TTG AAG TTA GTG CTT TAC     720
Leu Ile Thr Asn Val Asp Gly Lys Pro Leu Leu Lys Leu Val Leu Tyr
225                 230                 235                 240

CAT ACC AAT AAC CAA CCG CCG CCG ATG CTA GAT TAC AGT ATA ATA ATT     768
His Thr Asn Asn Gln Pro Pro Pro Met Leu Asp Tyr Ser Ile Ile Ile
                245                 250                 255

CTA TTA GTT GAG ATG TCA TTT TTA CTG ATC CTC GCT TAT TTC CTT TAC     816
Leu Leu Val Glu Met Ser Phe Leu Leu Ile Leu Ala Tyr Phe Leu Tyr
            260                 265                 270

TCC TAC TTC TTA GTC AGG CCA GTT AGA AAG CTG GCT TCA GAT ATT AAA     864
```

Ser Tyr Phe Leu Val Arg Pro Val Arg Lys Leu Ala Ser Asp Ile Lys
275 280 285

AAA ATG GAT AAA AGT CGT GAA ATT AAA AAG CTA AGG TAT CAC TAC CCT 912
Lys Met Asp Lys Ser Arg Glu Ile Lys Lys Leu Arg Tyr His Tyr Pro
290 295 300

ATT ACT GAG CTA GTC AAA GTT GCG ACT CAC TTC AAC GCC CTA ATG GGG 960
Ile Thr Glu Leu Val Lys Val Ala Thr His Phe Asn Ala Leu Met Gly
305 310 315 320

ACG ATT CAG GAA CAA ACT AAA CAG CTT AAT GAA CAA GTT TTT ATT GAT 1008
Thr Ile Gln Glu Gln Thr Lys Gln Leu Asn Glu Gln Val Phe Ile Asp
325 330 335

AAA TTA ACC AAT ATT CCC AAT CGT CGC GCT TTT GAG CAG CGA CTT GAA 1056
Lys Leu Thr Asn Ile Pro Asn Arg Arg Ala Phe Glu Gln Arg Leu Glu
340 345 350

ACC TAT TGC CAA CTG CTA GCC CGG CAA CAA ATT GGC TTT ACT CTC ATC 1104
Thr Tyr Cys Gln Leu Leu Ala Arg Gln Gln Ile Gly Phe Thr Leu Ile
355 360 365

ATT GCC GAT GTG GAT CAT TTT AAA GAG TAC AAC GAT ACT CTT GGG CAC 1152
Ile Ala Asp Val Asp His Phe Lys Glu Tyr Asn Asp Thr Leu Gly His
370 375 380

CTT GCT GGG GAT GAA GCA TTA ATA AAA GTG GCA CAA ACA CTA TCG CAA 1200
Leu Ala Gly Asp Glu Ala Leu Ile Lys Val Ala Gln Thr Leu Ser Gln
385 390 395 400

CAG TTT TAC CGT GCA GAA GAT ATT TGT GCC CGT TTT GGT GGT GAA GAA 1248
Gln Phe Tyr Arg Ala Glu Asp Ile Cys Ala Arg Phe Gly Gly Glu Glu
405 410 415

TTT ATT ATG TTA TTT CGA GAC ATA CCT GAT GAG CCC TTG CAG AGA AAG 1296
Phe Ile Met Leu Phe Arg Asp Ile Pro Asp Glu Pro Leu Gln Arg Lys
420 425 430

CTC GAT GCG ATG CTG CAC TCT TTT GCA GAG CTC AAC CTA CCT CAT CCA 1344
Leu Asp Ala Met Leu His Ser Phe Ala Glu Leu Asn Leu Pro His Pro
435 440 445

AAC TCA TCA ACC GCT AAT TAC GTT ACT GTG AGC CTT GGG GTT TGC ACA 1392
Asn Ser Ser Thr Ala Asn Tyr Val Thr Val Ser Leu Gly Val Cys Thr
450 455 460

GTT GTT GCT GTT GAT GAT TTT GAA TTT AAA AGT GAG TCG CAT ATT ATT 1440
Val Val Ala Val Asp Asp Phe Glu Phe Lys Ser Glu Ser His Ile Ile
465 470 475 480

GGC AGT CAG GCT GCA TTA ATC GCA GAT AAG GCG CTT TAT CAT GCT AAA 1488
Gly Ser Gln Ala Ala Leu Ile Ala Asp Lys Ala Leu Tyr His Ala Lys
485 490 495

GCC TGT GGT CGT AAC CAG TTG TCA AAA ACT ACT ATT ACT GTT GAT GAG 1536
Ala Cys Gly Arg Asn Gln Leu Ser Lys Thr Thr Ile Thr Val Asp Glu
500 505 510

ATT GAG CAA TTA GAA GCA AAT AAA ATC GGT CAT CAA GCC 1575
Ile Glu Gln Leu Glu Ala Asn Lys Ile Gly His Gln Ala
515 520 525

( 2 ) INFORMATION FOR SEQ ID NO:19:

( i ) SEQUENCE CHARACTERISTICS:
( A ) LENGTH: 525 amino acids
( B ) TYPE: amino acid
( D ) TOPOLOGY: linear ( i i ) MOLECULE TYPE: protein ( x i ) SEQUENCE DESCRIPTION: SEQ ID NO:19:

Val Gln Leu Pro Leu Ile Glu Ala Ser Leu Val Lys Leu Ser Glu Gln
1 5 10 15

Glu Leu Thr Ser Leu Asn Tyr Ala Phe Gln Gln Met Arg Lys Pro Leu
20 25 30

-continued

```
Gln Thr Ile Asn Tyr Asp Tyr Ala Val Trp Asp Arg Thr Tyr Ser Tyr
        35                  40                  45

Met Lys Ser Asn Ser Ala Ser Ala Lys Arg Tyr Tyr Glu Lys His Glu
    50                  55                  60

Tyr Pro Asp Asp Thr Phe Lys Ser Leu Lys Val Asp Gly Val Phe Ile
65                  70                  75                  80

Phe Asn Arg Thr Asn Gln Pro Val Phe Ser Lys Gly Phe Asn His Arg
                85                  90                  95

Asn Asp Ile Pro Leu Val Phe Glu Leu Thr Asp Phe Lys Gln His Pro
            100                 105                 110

Gln Asn Ile Ala Leu Ser Pro Gln Thr Lys Gln Ala His Pro Pro Ala
        115                 120                 125

Ser Lys Pro Leu Asp Ser Pro Asp Asp Val Pro Ser Thr His Gly Val
    130                 135                 140

Ile Ala Thr Arg Tyr Gly Pro Ala Ile Tyr Ser Ser Thr Ser Ile Leu
145                 150                 155                 160

Lys Ser Asp Arg Ser Gly Ser Gln Leu Gly Tyr Leu Val Phe Ile Arg
                165                 170                 175

Leu Ile Asp Glu Trp Phe Ile Ala Glu Leu Ser Gln Tyr Thr Ala Ala
            180                 185                 190

Gly Val Glu Ile Ala Met Ala Asp Ala Ala Asp Ala Gln Leu Ala Arg
        195                 200                 205

Leu Gly Ala Asn Thr Lys Leu Asn Lys Val Thr Ala Thr Ser Glu Arg
    210                 215                 220

Leu Ile Thr Asn Val Asp Gly Lys Pro Leu Leu Lys Leu Val Leu Tyr
225                 230                 235                 240

His Thr Asn Asn Gln Pro Pro Pro Met Leu Asp Tyr Ser Ile Ile Ile
                245                 250                 255

Leu Leu Val Glu Met Ser Phe Leu Leu Ile Leu Ala Tyr Phe Leu Tyr
            260                 265                 270

Ser Tyr Phe Leu Val Arg Pro Val Arg Lys Leu Ala Ser Asp Ile Lys
        275                 280                 285

Lys Met Asp Lys Ser Arg Glu Ile Lys Lys Leu Arg Tyr His Tyr Pro
    290                 295                 300

Ile Thr Glu Leu Val Lys Val Ala Thr His Phe Asn Ala Leu Met Gly
305                 310                 315                 320

Thr Ile Gln Glu Gln Thr Lys Gln Leu Asn Glu Gln Val Phe Ile Asp
                325                 330                 335

Lys Leu Thr Asn Ile Pro Asn Arg Arg Ala Phe Glu Gln Arg Leu Glu
            340                 345                 350

Thr Tyr Cys Gln Leu Leu Ala Arg Gln Gln Ile Gly Phe Thr Leu Ile
        355                 360                 365

Ile Ala Asp Val Asp His Phe Lys Glu Tyr Asn Asp Thr Leu Gly His
    370                 375                 380

Leu Ala Gly Asp Glu Ala Leu Ile Lys Val Ala Gln Thr Leu Ser Gln
385                 390                 395                 400

Gln Phe Tyr Arg Ala Glu Asp Ile Cys Ala Arg Phe Gly Gly Glu Glu
                405                 410                 415

Phe Ile Met Leu Phe Arg Asp Ile Pro Asp Glu Pro Leu Gln Arg Lys
            420                 425                 430

Leu Asp Ala Met Leu His Ser Phe Ala Glu Leu Asn Leu Pro His Pro
        435                 440                 445

Asn Ser Ser Thr Ala Asn Tyr Val Thr Val Ser Leu Gly Val Cys Thr
```

| | | | | | | | | | | | | | | | |
|---|---|---|---|---|---|---|---|---|---|---|---|---|---|---|---|
| | 450 | | | | 455 | | | | | 460 | | | | | |
| Val | Val | Ala | Val | Asp | Asp | Phe | Glu | Phe | Lys | Ser | Glu | Ser | His | Ile | Ile |
| 465 | | | | | 470 | | | | | 475 | | | | | 480 |
| Gly | Ser | Gln | Ala | Ala | Leu | Ile | Ala | Asp | Lys | Ala | Leu | Tyr | His | Ala | Lys |
| | | | | 485 | | | | | 490 | | | | | 495 | |
| Ala | Cys | Gly | Arg | Asn | Gln | Leu | Ser | Lys | Thr | Thr | Ile | Thr | Val | Asp | Glu |
| | | | 500 | | | | | 505 | | | | | 510 | | |
| Ile | Glu | Gln | Leu | Glu | Ala | Asn | Lys | Ile | Gly | His | Gln | Ala | | | |
| | | 515 | | | | | 520 | | | | | 525 | | | |

( 2 ) INFORMATION FOR SEQ ID NO:20:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:20:

AGCTCAAACA ACGCGCTTAC A 21

( 2 ) INFORMATION FOR SEQ ID NO:21:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( x i ) SEQUENCE DESCRIPTION: SEQ ID NO:21:

TGTTAGTCCC ATCACGTTCT TG 22

( 2 ) INFORMATION FOR SEQ ID NO:22:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( x i ) SEQUENCE DESCRIPTION: SEQ ID NO:22:

GCCATCATCA GGTGCCATTA TCGGT 25

( 2 ) INFORMATION FOR SEQ ID NO:23:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( x i ) SEQUENCE DESCRIPTION: SEQ ID NO:23:

GTCTGGGTAG GCGTGGAAGA TT 22

( 2 ) INFORMATION FOR SEQ ID NO:24:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( x i ) SEQUENCE DESCRIPTION: SEQ ID NO:24:

AGTATCTGCG TCCTAACTCG AT 22

( 2 ) INFORMATION FOR SEQ ID NO:25:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( x i ) SEQUENCE DESCRIPTION: SEQ ID NO:25:

CCACCTGAAT CGGCCTCTG 19

GENE CODING FOR EICOSAPENTAENOIC ACID SYNTHESIZING ENZYMES AND PROCESS FOR PRODUCTION OF EICOSAPENTAENOIC ACID

CROSS REFERENCE TO RELATED APPLICATION

This application is a continuation-in-part application of Ser. No. 08/375,709 filed on Jan. 20, 1995, now U.S. Pat. No. 5,683,898 which is a continuation-in-part application of Ser. No. 08/178,251 filed on Jan. 10, 1994 now abandoned.

FIELD OF THE ART

The present invention relates to genes coding for eicosapentaenoic acid (designated EPA hereinafter) synthesizing enzymes, plasmids containing these genes, microorganisms transformed with the plasmid, and a process for production of eicosapentaenoic acid using the microorganism. The EPA is useful as a starting material for pharmaceuticals, foods, feeds and the like.

BACKGROUND ART

Polyunsaturated fatty acids represented by eicosapentaenoic acid (EPA) play an important roll as a component of a biomembrane. So far, the following pharmacological actions of EPA are known. (1) Platelet coagulation inhibitory action (thrombolytic action), (2) blood neutral fat-lowering action, (3) actions for lowering blood VLDL-cholesterol and LDL-cholesterol and increasing HDL-cholesterol (anti-arterial sclerosis action), (4) blood viscosity-lowering action, (5) blood pressure lowering action, (7) anti-inflammatory action, (8) anti-tumor action.

In addition, EPA is a substrate for biosynthesis of prostaglandins and exhibits an essential function in vivo in higher mammals including humans. In particular EPA is important as a substrate for production of three types of prostaglandins, has platelet coagulation inhibitory action and is studied for applications to treatment and prophylactic agents for thrombosis. In addition EPA has especially high activity for lowering plasma cholesterol level among polyunsaturated fatty acids having said action, and is highly effective in comparison with linoleic acid and the like usually contained in plant oil. Additionally, EPA is known as an essential nutrient for fish.

Thus, epidemiological research by Dyerberg, Denmark (Am. J. Clin. Nutur, 28, 959, 1975) showed a possibility for use as health foods or pharmaceuticals on the basis of thrombosis inhibitory action or lipid-lowering actions of EPA. However, as can be seen from its chemical structure, the chemical synthesis of EPA is very difficult. Accordingly, in Japan, it is recommended to eat blue back fish such as sardine, salmon, saury, and the like.

At present, most commercially available EPA products are fractionation products from fish oil obtained by a boiling process, and the EPA content thereof is about 10 to 30%. Fish oil extracted by a boiling process is a mixed glyceride containing various kind of fatty acids as component fatty acids, and not only is isolation and purification of each component difficult, but also since EPA is a polyunsaturated fatty acid having 20 carbon atoms and five double bonds all of which are cis-type, EPA is also a unstable and highly oxidation-labile fatty acid. Therefore, it is necessary for EPA to be concentrated from fish oil with prevention of oxygen, light, heat and the like. In addition, since fish oil contains various fatty acids in addition to EPA, their fractionation is difficult. Moreover, although various organic solvents used for fractionation of EPA are eliminated under a reduced pressure, complete elimination of the organic solvents is difficult from a technical and economical point of view.

Most EPA preparations used for pharmaceuticals are those having at least 90% EPA concentration, produced by extracting fish oil by various processes, hydrolysing the fish oil enzymatically or under an alkaline condition to generate free fatty acids, optionally converting the free fatty acids to corresponding methyl or ethyl esters, and further purifying by fractional crystallization at a low temperature, applying a urea-addition method, distillation under a reduced pressure, reverse phase chromatography, or the like. However, since these processes use many organic solvents and heating to near 200° C., it is possible that an EPA concentrate obtained by using such process may be denaturated by residual organic solvent, and polymerization, isomerization or oxidation of EPA. Moreover, where a fish oil is used as a starting material for production of EPA, it is difficult to eliminate docosanoic acid or the like which is considered to be a cause of cardiodiseases, and therefore problems remain in the use for health foods, pharmaceuticals or the like.

On the other hand, recently, processes for production of EPA using microorganisms such as chlorella, unicellular algae Monodus, Eugrena or Diatomaceae have been studied in place of extraction methods from fish oil having drawbacks such as residual fish odor due to incomplete purification and concentration, and the production of EPA using microorganisms has been considered. Recently, fungi producing EPA were reported by Gellerman and Schlenk (J. L. Gellerman and H. Schlenk, BBA, 573, 23, 1979) and Yamada et al. (Meeting of The society of Fermentation Technology, Japan, 1986).

The present inventors sought marine bacteria having an ability to produce EPA to find a new fermentation process for production of EPA using bacteria from which genes can be easily obtained, and which can be cultured in a short time and be easily controlled, and as a result, the present inventors found a new bacteria belonging to the genus Pseudomonas, Alteromonas or Shewanella (K. Yazawa et al., J. Biochem., 103, 5 (1988); K. Yazawa et al., Nippon Suisan Gakkai shi, 54, 1835 (1988)).

It has been suggested that biosynthesis of polyunsaturated fatty acids including EPA works by site-specific aerobic unsaturation of corresponding saturated fatty acids (for example, R. Jeffcoat and A. T. James (1984) in: S. Numa (Ed.): Fatty acid metabolism and its regulation, Elsevier, Amsterdam, pp 85–112). However, there is no report relating to biosynthetic enzymes which participate in EPA synthesis, and gene coding therefor.

DISCLOSURE OF THE INVENTION

Generally, the ability of a wild strain to produce a useful substance is low, and therefore where it is intended that the ability of the microorganism is industrially used, an improvement, i.e., an increase of productivity of the microorganism is carried out by various methods. The present inventors intended to carry out research for increasing an EPA productivity by finding genes not described in literature for EPA biosynthetic enzymes using gene recombination techniques and introducing the same into another organism, to impart an EPA biosynthesis ability to an organism not having an EPA biosynthesis ability, and eventually to establish an advantageous process for production of EPA.

Accordingly, the present invention provides genes for EPA biosynthetic enzymes, expression plasmids containing said genes, organisms transformed with said plasmid, and a process for production of EPA using said organism.

BEST MODE FOR CARRYING OUT THE INVENTION

Figure 1:
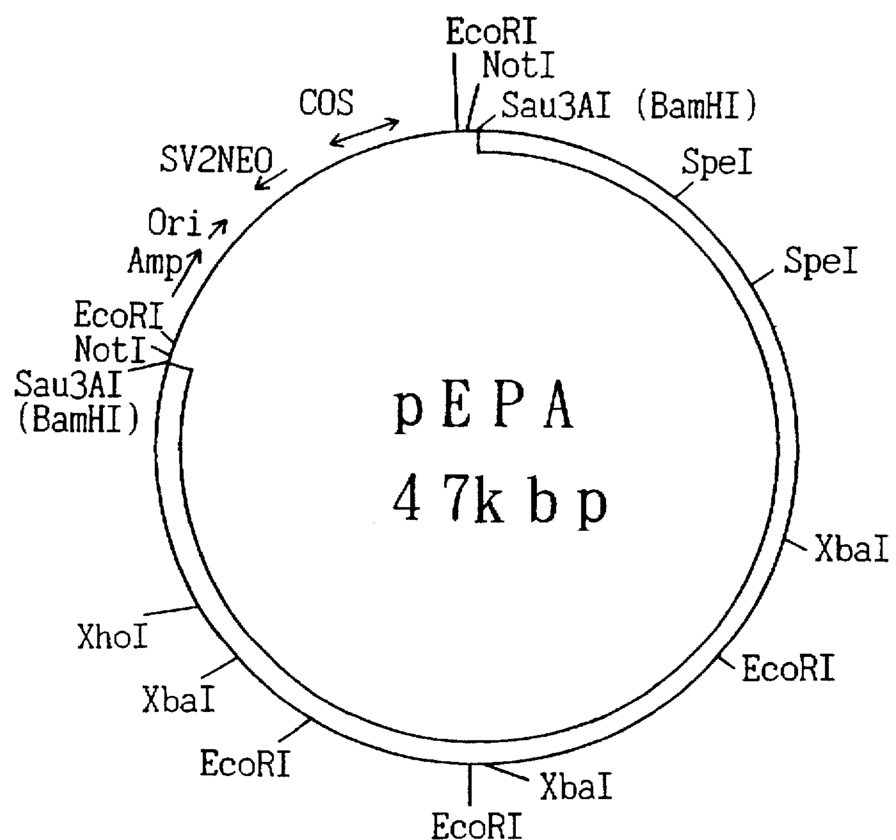
FIG. 1 represents the structure of the plasmid pEPA containing a group of the present genes.

According to the present invention, an EPA producing strain is constructed by extracting DNA from a microorganism having an ability to produce EPA (microbial origin of genes), cutting this DNA with restriction enzymes to excise genes coded for a group of EPA biosynthesis enzymes, introducing the genes into an appropriate vector to construct an expression plasmid, and transforming a host organism with the plasmid to construct an EPA producing strain. EPA can be produced by this organism.

Gene source

Although organisms which can be used as a gene source according to the present invention are not limited to specific genera, species or strains, usually, microorganisms classified to the genus Pseudomonas, Alteromonas, Shewanella or the like can be used. These microorganisms can be easily obtained from official or public depository institutes for microorganisms.

As examples of microorganisms belonging to the genus Pseudomonas, *Pseudomonas putrefaciens* SCRC-2181 (FERM BP-2917), SCRC-2201 (FERM BP-2916), SCRC-2271 (FERM BP-2195), SCRC-2341 (FERM BP-2918), SCRC-2451 (FERM BP-2919), SCRC-2642 (FERM BP-2920), SCRC-2792 (FERM BP-2921), SCRC-2878 (FERM BP-1623), SCRC-3011 (FERM BP-2913), and SCRC-3022 (FERM BP-2914) may be mentioned.

As example of microorganisms belonging to the genus Alteromonas, *Alteromonas putrefaciens* SCRC-2871 (FERM BP-1624) and *Alteromonas putrefaciens* subspecies sagamifaciens SCRC-1162 (FERM BP-1626) may be mentioned.

As an example of microorganism belonging to the genus Shewanella, *Shewanella putrefaciens* SCRC-2874 (FERM BP-1625) may be mentioned.

Cloning of Genes Coding for a Group of EPA Biosynthesis Enzymes and Construction of Expression Plasmid In the present invention, the case wherein *Shewanella putrefaciens* SCRC-2874 (FERM BP-1625) was used as a source of genes for a group of EPA biosynthesis enzymes is concretely explained. However, as described above, various EPA producing microorganisms can be similarly used as a gene source. A process for cloning genes is described in the Examples of the present invention.

According to the present invention, EPA producing strains can be artificially generated by transforming an heterogeneous host such as *Escherichia coli* or a homogeneous host such as Shewanella, or further yeast, fungus or the like. In addition, EPA producing plants can be generated by introducing the present genes into a higher plant such as soybean, sunflower, rape, or the like. As a region for expression of a group of EPA biosynthesis genes, although a control region natively accompanying these enzymes can be used, it is advantageous to prepare another promoter/operator system for increasing an amount of expression or allowing inducible expression. Where *E. coli* is used as a host, as the promoter/operator system, trp, tac, lavUV5, $P_L$, $P_R$ or 1 pp promoter/operator system and the like can be used, and as an SD sequence, an SD sequence of trp leader peptide, lacZ, metapyrocatechase or cII gene can be used. In addition, a transcriptional terminator, for example, rrnB$T_1T_2$ terminator of *E. coli* ribosome gene or the like can be provided downstream of a coding region. In addition, for expression of the above-mentioned gene, a host/vector system of *Saccharomyces cerevisiae* can be used, wherein as a promoter there can be used a promoter of alcohol dehydrogenase gene, a promoter of acid phosphatase gene, a promoter of glycelaldehyde-3-phosphate dehydrogenase gene, a promoter of enolase gene or the like can be used, wherein a plasmid preferably contains a sequence for replication in yeast, and an auxotrophic marker as a selectable maker for selection of yeast containing said plasmid, such as Leu, Trp, His or the like.

For introduction of the genes into a plant, there are a method using a vector, and a direct introduction method. As vectors, Ti plasmid; DNA viruses such as cauliflower mosaic virus (CaMV), Geminivirus, cassava roten virus, tomato golden mosaic virus, and the like; and RNA viruses such as brome mosaic virus (BMV), and tobacco mosaic virus (TMV) can be used, wherein as a promoter, 35S promoter of CaMV or the like may be mentioned. On the other hand, as direct protoplast introduction methods there can be mentioned a calcium phosphate method, polyethylene glycol method, microinjection, electroporation, liposome method and the like. Moreover, as a direct plant cell introduction method, there may be mentioned a particle gun-method.

In addition, a fatty acid composition in a host plant can be changed by using a part of the group of the genes.

Note, that generally, an amount of expression of a particular protein in *E. coli* is affected by the number of copies of the genes, an efficiency of transcription, stability of mRNA, efficiency of translation, and stability of the protein. To modify control regions such as a promoter, SD region, terminator and the like, a smaller plasmid can be easily treated. The number of copies of the genes depends on the size of the plasmid, and there is a tendency for the plasmid to be smaller as the number of copies increases. For this purpose, a smaller plasmid can be obtained by inserting a DNA fragment containing a group of genes for EPA biosynthesis described in the Examples of the present invention into a plasmid, and repeating subcloning of the plasmid to cut off unnecessary portions of the gene DNA fragment. Smaller EPA biosynthesis enzyme genes thus obtained are included in the present invention. In addition, to enhance stability or activity of the enzyme, the nucleotide sequence of the gene (amino acid sequence) can be modified by a known technique, and the present invention includes such a modified gene.

As a host *E. coli* of the present invention, any strain derived from *E. coli* K12 may be used. For example, JM83, JM101, JM103, JM105, JM109, RR1, RB791, W3110, C600, HB101, DH1, AG1, NM554 or the like can be used. As a yeast host, AH22, DC5, D-13-1A, YNN144 or the like can be mentioned.

Note, that a group of the enzymes encoded by the present genes can convert higher fatty acids synthesized by a biosynthetic system natively possessed by the host organism to eicosapentaenoic acid.

In practicing the present invention, an organism such as a microorganism transformed with the present genes is cultured in a medium according to a conventional procedure to obtain microbial cells. In this case, for example, a medium having a composition shown in Table 1 is prepared.

TABLE 1

| | |
|---|---|
| Yeast extract | 0.5% |
| Tryptone | 1.0% |
| Nacl | 1.0% |
| pH 7.5 | |

From the microbial cells thus obtained, EPA can be obtained according to a conventional procedure such as extraction with an organic solvent. The details are described in the following Examples.

EXAMPLES

Next, the present invention is explained in more detail by way of Examples.

Example 1-1

Preparation of Genomic DNA Containing Genes Coding for a Group of EPA Biosynthesis Enzymes

*Shewanella putrefaciens* SCRC-2874 (FERM BP-1625) was inoculated in 125 ml of a medium (1% pepton, 0.5% yeast extract, ½ concentration artificial sea water), and cultured at 15° C. for 18 hours with shaking (OD610=8.6). The resulting microbial cells were washed once with 1M NaCl, and suspended in 20 ml of 1M NaCl. The suspension was allowed to stand at 55° C. for 30 minutes, 20 ml of 0.1M EDTA was added thereto, and after being allowed to stand at 55° C. for 15 minutes, the suspension was centrifuged at 10,000 rpm for 10 minutes. To the precipitate, was added 10 ml of TES buffer (1 mM EDTA, 0.1 mM NaCl, 10 mM Tris-HCl, pH 8.0) containing 100 mg of lysozyme, and the cells were suspended. After being allowed to stand at 37° C. for an hour, 1 ml of 10% SDS was added to the suspension, which was then allowed to stand at 60° C. for an hour. 11 ml of neutralized phenol was added to the suspension, which was then gently shaken for 5 minutes and centrifuged at 6,500 rpm for 5 minutes to obtain the upper layer. 20 ml of ethanol was added to the layer and the mixture was gently shaken. Precipitated DNA was wound onto a glass bar, washed in ethanol, dissolved in 10 ml of TES buffer, and the solution was allowed to stand at 4° C. overnight. 0.5 mg of RNase A was added to the solution, which was then gently shaken at 37° C. for 3 hours, and after 1 mg of proteinase K was added thereto, the solution was further shaken for 4.5 hours; 5 ml each of neutralized phenol and chloroform were gradually added to the mixture, which was then gently shaken for 5 minutes and centrifuged to recover the upper layer. 10 ml of chloroform was added to the layer, which was then gently shaken and centrifuged to obtain the upper layer. 20 ml of ethanol was added to the layer, which was then gently shaken, and precipitated DNA was wound onto a glass bar. The DNA was washed in ethanol, and dissolved in 3 ml of TES buffer. An amount of DNA thus obtained was about 2.8 mg. Next, 200 μg of the DNA was partially digested with restriction enzyme Sau3A1and subjected to electrophoresis on 0.3% agarose, and DNA fragments larger than about 20 Kb were isolated by electroelusion. The DNA fragments were extracted with phenol/chloroform, and precipitated with ethanol, and the precipitate was dissolved in 500 μl of TE buffer (1 mM EDTA, 10 mM Tris-HCl, pH 7.4).

Example 1-2

Insertion of Chromosomal DNA Fragments into Vector

As a vector, cosmid pWE15 (STRATAGENE) was used. 10 μg of pWE15 was completely digested with restriction enzyme BamHI, treated with calf intestine alkaline phosphatase at 37° C. for an hour, extracted with phenol/chloroform, and precipitated with ethanol, and the precipitate was dissolved in 10 μl of TE buffer. 1.5 μg of the vector DNA thus obtained was mixed with 1 μg of the chromosomal DNA prepared in Example 1 and partially digested with restriction enzyme Sau3A1, and these DNA were ligated using T4 DNA ligase at 26° C. for 10 minutes. One fourth of the reaction mixture was packaged according to a conventional method to form phage, which was then infected to *E. coli* K12/AG-1.

Example 1-3

Screening of Recombinant EPA Producing Strain

The *E. coli* suspension infected with the phage of Example 1-2 was plated on an LB agar medium (trypton 1%, yeast extract 0.5%, NaCl 1%, Agar 2%) containing 50 μg/ml ampicillin and cultured at 37° C. overnight. The developed colony was inoculated in 1.5 ml of LB medium containing 50 μg/ml ampicillin, and cultured at 25° C. for 1 to 7 days with shaking. The culture was centrifuged to collect the microbial cells, and after removing the medium, the cells were suspended in 0.5 ml of methanol saturated with hydrogen chloride. The cell suspension was sealed and incubated at 80° C. for an hour to methyl-esterify fatty acids. After allowing the suspension to cool, it was extracted three times with 0.3 ml hexane, the hexane layer was dried and the residue was dissolved in 20 μl of methanol. 2 μl of the solution was spotted on a silica gel plate which was then developed three times with a developing solvent of hexane and ether 19:1, dried in air, and colored with iodine.

In this way, as a result of tests of about 390 recombinant clones, one clone showing a thin layer chromatography spot at the same position as a standard methyl ester of EPA was obtained. From the clone, cosmid was extracted using an alkali/SDS method. This cosmid was designated as pEPA. The pEPA is a cosmid wherein a San3AI fragment of about 38 Kbp was inserted into BamHI site of pWE15.

Example 1-4

Preparation of Restriction Enzyme Map of pEPA

Comsmid pEPA was prepared from transformant AG-1/pEPA. The pEPA was cleaved with various restriction enzymes, and a restriction enzyme map was prepared (FIG. 1).

Example 1-5

Analysis of Sequence

An entire nucleotide sequence of a Sau3A1-Sau3A1 fragment containing a genomic DNA insert in the cosmid pEPA is shown in SEQ ID NO: 1. In the nucleotide sequence, 9 open reading frames, ORFs 2 to 10, can be identified, and these nucleotide sequences and corresponding amino acid sequences are shown in SEQ ID NOs: 2 to 19 respectively. The relationship between the entire nucleotide sequence (SEQ ID NO: 1) and ORFs 2 to 10 (SEQ ID NOs: 2 to 19, respectively) is shown in Table 2.

TABLE 2

| SEQ ID NO | Length of sequence | Positions on SEQ ID NO: 1 |
|---|---|---|
| 2 | 1983 | 6121–8103 |
| 4 | 831 | 8186–9016* |
| 6 | 2910 | 9681–12590 |
| 8 | 864 | 13040–13903 |
| 10 | 8268 | 13906–22173 |
| 12 | 2340 | 22176–24515 |
| 14 | 6012 | 24518–30529 |
| 16 | 1629 | 30730–32358 |
| 18 | 1575 | 32753–34327 |

*Reversed (and complemented)? sequence extending from the position No. 9016 to the position No. 8186 in the nucleotide sequence shown in SEQ ID NO: 1.

Figure 2:
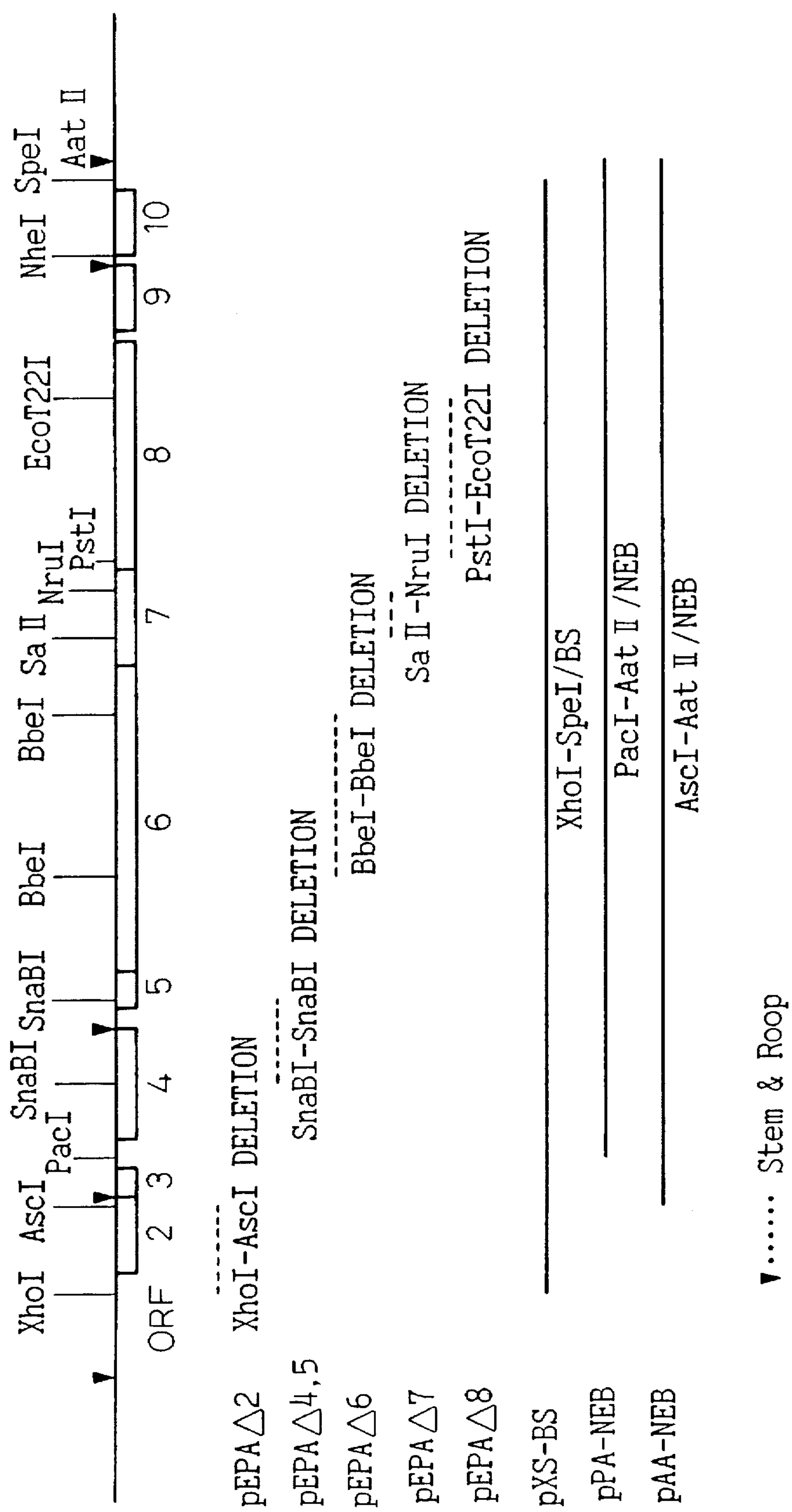
FIG. 2 represents a restriction enzyme map of a DNA fragment containing a group of the present genes.

A restriction enzyme map of the above-mentioned genomic DNA insert and positions of the ORFs 2 to 10 on the map are shown in FIG. 2. In FIG. 2, the symbols Δ show the sites at which mRNA forms a hair pin structure (stem and roop structure).

By comparison of the amino acid sequences of various ORFs with known amino acid sequences, it was found that five regions in the ORF 6, and 2 regions in the ORF 8 have homology to some extent with amino acid sequences of enzymes participating in fatty acid synthesis. The results are shown in Table 3.

TABLE 3

| SEQ. ID NO (ORF No.) | Position of amino acid sequence | Similar enzyme and position | References | Homology (%) |
|---|---|---|---|---|
| 10 (6) | 668(Leu)-930(Leu) | Malony1CoA-ACP transferase 56 (Leu)-309(Leu) | (1) | 29.1 |
| 10 (6) | 189(Phe)-424(His) | Fatty acid synthetase 120(Phe)-350(His) | (2) | 28.3 |
| 10 (6) | 200(Ser)-483(Leu) | Fatty acid synthetase (3-ketoacyl-ACP synthetase domain) 137(Ala)-406(Asp) | (3) | 29.3 |
| 10 (6) | 204(Ser)-488(Gln) | 3-Ketoacyl-ACP synthetase 137(Ala)-406(Asp) | (4) | 26.9 |
| 10 (6) | 2261(Phe)-2392(Gly) | 2-Oxoacylreductase 1470(Leu)-1604(Gly) | (5) | 25.8 |
| 14 (8) | 205(Ala)-442(Lys) | 3-Ketoacyl-ACP synthetase 187(Ala)-416 (Asn) | (6) | 29.1 |
| 14 (8) | 1373(Thr)-1547(Val) | 3-Hydroxydecanoyl-ACP dehydratase 29(Leu)-163(Val) | (7) | 31.0 |

References
(1) Magnuson K. et al., FEBS Lett. (1992) 299:262–266
(2) Kameda K. et al., J. Biol. Chem. (1991) 266:419–426
(3) Huang W. Y. et al., Arch. Biochem. Biophys. (1989) 270:92–98
(4) Kauppinen S. et al., Carlsberg Res. Commun. (1988) 53:357–370
(5) Beck J. et al., Eur. J. Biochem. (1990) 192:487–498
(6) Siggaard-Andersen M. et al., Proc. Natl. Acad.Sci. U.S.A. (1991) 88:4114–4118
(7) Cronan Jr. J. E. et al., J. Biol. Chem. (1988) 263:4641–4646

Example 2

Production of EPA by Transformant AG-1/pEPA

Transformant AG-1/pEPA was inoculated in 100 ml of LB medium containing 50 μl/ml ampicillin, and cultured at 25° C. for 48 hours. The cells were obtained by centrifugation, washed once and suspended in 2 ml of pure water, and the suspension was extracted three times with 12 ml of a solvent composed of chloroform and methanol 2:1. The solvent layer was dried, and the residue was dissolved in 1.5 ml of methanol saturated with hydrogen chloride, and the solution was sealed and incubated at 80° C. for an hour to methyl-esterify fatty acids. After allowing the solution to cool, it was extracted three times with 2 ml of hexane, and after the hexane layer was dried, the residue was dissolved in 20 μl of methanol. A part of the solution was analyzed by gas chromatography. As a result, a peak of EPA was observed, and a ratio of EPA relating to total fatty acid esters was calculated as about 1.36% from the area of peaks. The amount of EPA per culture volume was about 0.5 mg/l. The ester mixture thus obtained was spotted on an argentation silica gel plate, which was then developed by a solvent composed of hexane and ether at a ratio of 3:1. The plate was colored with fluorescein and ultraviolet light, the spot of the ester of the polyunsaturated fatty acid was scraped off, 1.8 ml of methanol and 0.2 ml of 10% NaCl were added thereto, and the mixture was shaken at room temperature for 30 minutes. The mixture was extracted three times with 2 ml of hexane, the hexane layer was dried, the residue was dissolved in 40 μl of hexane, and GC-MS analysis was carried out. As a result, molecular weight of the substance of the desired peak on the chromatography was 316, and the peak of the fragment conformed to that of an authentic sample, and the substance was identified as EPA. Note that MS fragment peaks were as follow:

Mass: 316($M^+$), 287, 273, 262, 247, 234, 220, 201, 180, 161, 148, 133, 119, 108, 93, 79, 67, 55, 41, 28.

Example 3

Production of EPA by Transformant JM109/pEPA

According to a conventional procedure the cosmid pEPA was used to transform *E. coli* K12/JM109. JM109/pEPA (FERM BP-4257) was obtained by selection using an LB agar medium containing 50 μl/ml ampicillin. According to the same procedure as described in Example 2, extraction of lipid from the cells, methyl-esterification and analysis by gas chromatography were carried out and a peak of EPA was detected. A ratio of EPA relating to a total of esters of fatty acids was calculated as about 1.43% on the basis of the area of peaks. An amount of EPA per culture volume was about 0.6 mg/l.

Example 4

To construct plasmids comprising a DNA wherein a part of the full length nucleotide sequence shown in SEQ ID NO: 1 has been deleted, the cosmid pEPA comprising a genomic insert having the nucleotide sequence shown SEQ ID NO: 1, constructed in Example 1-3 described in the specification was cleaved with various restriction enzymes and re-ligated to construct different plasmids. In this way, plasmids pEPAΔ2; pEPAΔ4, 5; pEPAΔ6; pEPAΔ7; pEPAΔ8; and pEPAΔ9 as shown in Table 4 were obtained. In addition, a DNA fragment XhoI(5661)-SpeI(34626) from the pEPA was inserted into XhoI-SpeI site of plasmid pBluescript (STRATAGENE) to construct pXS-BS. Further, a DNA fragment PacI(9060)-AatII(35559) from the pEPA was inserted into PacI-AatII site of plasmid pNEB (New England Biolabs) to construct pPA-NEB. In addition, a DNA fragment AscI(7709)-AatII(35559) from the pEPA was inserted into AscI-AatII site of plasmid pNEB to construct pAA-NEB. In addition, a DNA fragment XhoI(5661)-NheI (32515) from the pEPA was inserted into XhoI-SpeI site of plasmid pBluescript to construct pXN-BS. These plasmids were used to transform *E. coli*, and productivity of eicosapentaenoic acid by the transformants were determined.

For each plasmid, positions of deletion in the nucleotide sequence shown in SEQ ID NO: 1 is shown in FIG. 2, and the productivity of eicosapentaenoic acid (EPA) for each plasmid is shown in Table 4.

TABLE 4

| Name of plasmid | Position of delation in SEQ ID NO: 1 | Delated ORF* | Productivity of EPA** (mg/L) |
|---|---|---|---|
| pEPAΔ2 | XhoI(5666)-AscI(7709) | 2 | 2.2 |
| pEPAΔ4, 5 | SnaBI(10944)-SnaBI(13226) | 4, 5 | 0.09 |
| pEPAΔ6 | Bbe1(16563)-BbeI(20702) | 6 | — |
| pEPAΔ7 | SalI(22265)-NruI(23847) | 7 | — |
| pEPAΔ8 | PstI(24814)-EcoT22I(28946) | 8 | — |
| pEPAΔ9 | SpeI(31446)-SpeI(34626)*** | 9 | |
| pXS-BS | Sau3AI(1)-XhoI(5660), SpeI(34632)-Sau3AI(37895) | — | 2.6 |
| pPA-NEB | Sau3AI(1)-PacI(9060), AatII(35565)-Sau3AI(37895) | 2, 3 | — |
| pAA-NEB | Sau3AI(1)-AscI(7709) AatII(35565)-Sau3AI(37895) | 2 | 3.7 |

*ORF = open reading frame
**EPA = eicosapentaenoic acid
***The sequence was inserted in a reverse direction.

From the above-mentioned result, it is suggested that an upstream region of ORF 2, a downstream region of ORF 10, and ORF 2 itself do not participate in the synthesis of eicosapentaenoic acid. Also, it is observed that ORFs 3, 6, 7, 8 and 9 are necessary for the synthesis of eicosapentaenoic acid.

Example 5-1

Construction of clone lacking ORFs 2 and 5, using two vectors

Figure 3:
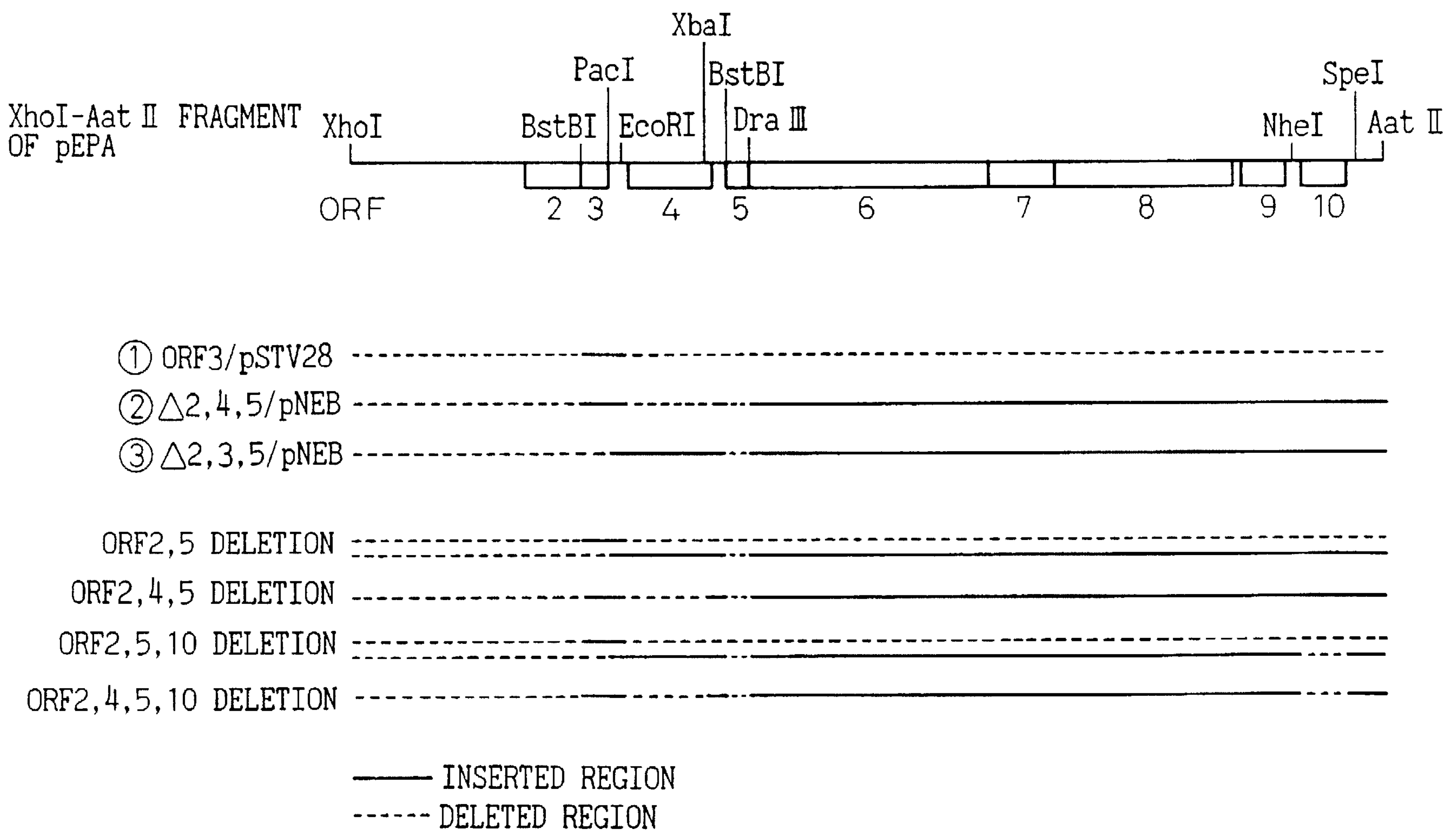
FIG. 3 represents the positions on the XhoI-ArtII fragment of pEPA, of the fragments inserted into the plasmids.

A BstBI(8081)-EcoRI(9441) fragment (1.36 Kbp) containing ORF 3 of cosmid pEPA was ligated to SmaI-EcoRI site of plasmid pSTV28 (Takara Shuzo) to construct plasmid ORF 3/pSTV28. A BstBI(13085)-DraIII(13888) fragment (0.8 Kbp) in ORF 5 was deleted from plasmid pPA-NEB containing ORFs 4 to 10 to construct plasmid Δ2, 3, 5/pNEB. *E. coli* transformed with Δ2, 3, 5/pNEB was further transformed with ORF 3/pSTV28, and the transformants were screened on an agar plate containing ampicillin and chloramphenicol to obtain a transformant (ORF 2, 5 deleted) containing the above-mentioned two plasmids. FIG. 3 shows the positions on the XhoI-ArtII fragment of pEPA, of the inserted fragments of these plasmids.

Example 5-2

Production of eicosapentaenoic acid using clone lacking ORF 2, 5

The clone lacking ORF 2, 5 constructed in Example 5-1 was cultured in 6 ml of LB medium containing 50 μg/ml ampicillin and 170 μg/ml chloramphenicol at 25° C. for 48 hours. 3 ml of the medium was sampled and centrifuged to obtain cells, which were then lyophilized overnight, suspended in 2 ml of methanol saturated with hydrogen chloride, and the suspension was incubated at 80° C. for an hour to esterify fatty acids extracted. After allowing to the cool, the reaction mixture was extracted three times with 2 ml of hexane, and the hexane layer was evaporated to dryness. The residue was dissolved in 10 μl of methanol. The solution was analyzed by gas chromatography. As a result, a peak of eicosapentaenoic acid was observed, and the ratio of the eicosapentaenoic acid per total fatty acid esters was calculated as 21.0% from the area of the peak. Productivity of eicosapentaenoic acid per culture medium was about 6.1 mg/L.

In addition, a peak was observed at the position corresponding to methyl docosapentaenoate (C22:5, n3), and the ratio thereof per total fatty acid esters was calculated as 3.1% from the area of the peak, and the productivity thereof per medium was 0.90 mg/L. Molecular weight of this substance was 344 as determined by GC-MS analysis, and therefore the substance was identified as methyl docosapentaenoate.

Mass: 344($M^+$), 315, 302, 290, 275, 264, 248, 236, 222, 208, 201, 187, 175, 161, 148, 133, 119, 105, 91, 79, 67, 55, 41, 29.

Example 6-1

Construction of clone lacking ORFs 2, 5 and 10, using two vectors

A BstI(13085)-DraIII(13888) fragment (0.8 Kbp) in ORF 5 and a NheI(32521)-SpeI(34626) fragment (2.1 Kbp) containing ORF 10 were deleted from plasmid pPA-NEB containing ORFs 4 to 10 of cosmid pEPA to construct a plasmid Δ2, 3, 5, 10/pNEB. *E. coli* JM109 transformed with Δ2, 3, 5, 10/pNEB was further transformed with ORF 3/pSTV28 constructed in Example 5-1, and the transformants screened on an agar plate medium containing ampicillin and chloramphenicol to obtain a transformant (ORF 2, 5, 10 deleted) containing two different plasmids. FIG. 3 shows the positions on the XhoI-ArtII fragment of pEPA, of the fragments inserted in the plasmids.

Example 6-2

Production of eicosapentaenoic acid using clone lacking ORFs 2, 5 and 10

The clone lacking ORFs 2, 5 and 10, constructed in Example 6-1 was cultured in 6 ml of LB medium containing 50 μg/ml ampicillin and 170 μg/ml chloramphenicol at 25° C. for 48 hours. 3 ml of the medium was sampled and centrifuged to obtain cells, which were then lyophilized overnight, suspended in 2 ml of methanol saturated with hydrogen chloride, and the suspension was incubated at 80° C. for an hour to esterify fatty acids extracted. After allowing to cool, the reaction mixture was extracted three times with 2 ml of hexane, and the hexane layer was evaporated to dryness. The residue was dissolved in 10 μl of methanol. The solution was analyzed by gas chromatography. As a result, a peak of eicosapentaenoic acid was observed, and the ratio of the eicosapentaenoic acid per total fatty acid esters was calculated as 21.6% from the area of the peak. Productivity of eicosapentaenoic acid per culture medium was about 6.3 mg/L.

Example 7-1

Construction of clone lacking ORFs 2, 4 and 5

An XbaI(12314)-ArtII(35559) fragment (23.3 Kbp) containing ORFs 5 to 10 of cosmid pEPA was ligated to XbaI-ArtII site of plasmid pNEB to construct PXA-NEB. A BstBI(13085)-DraIII(13888) fragment (0.8 Kbp) in ORF 5 was deleted from said plasmid pXA-NEB to construct plasmid Δ2, 3, 4, 5/pNEB.

A BstBI(8081)-EcoRI(9441) fragment (1.36 Kbp) of pEPA containing ORF 3 was inserted into SmaI-EcoRI site of PUC18 to construct ORF 3/pUC18. A PstI-PvuII fragment (1.57 Kbp) of the ORF 3/pUC18 containing ORF 3 was inserted into Sse8387I-PmeI site of the plasmid Δ2, 3, 4, 5/pNEB to construct plasmid Δ2, 4, 5/pNEB. *E. coli* JM109 was transformed with the Δ2, 4, 5/pNEB, and the transformants were screened on an agar plate medium containing ampicillin, to obtain a clone lacking ORFs 2, 4 and 5. FIG. 3 shows the positions on the XhoI-ArtII fragment of pEPA, of the fragments inserted in the plasmids.

Example 7-2

Production of eicosapentaenoic acid using clone lacking ORFs 2, 4 and 5

The clone lacking ORFs 2, 4 and 5, constructed in Example 7-1 was cultured in LB medium containing 50 μg/ml ampicillin according to the procedure as described in Example 5-2, and methyl esterification of lipid in the cells, an extraction with hexane and analysis by gas chromatography were carried out according to the procedure as described in Example 5-2. As a result, the ratio of the eicosapentaenoic acid per total fatty acid esters was calculated as 16.1% from the area of the peak. Productivity of eicosapentaenoic acid per culture medium was about 4.7 mg/L.

In addition, a peak was observed at the position corresponding to methyl docosapentaenoate (C22:5, n3), and the ratio thereof për total fatty acid esters was calculated as 2.5% from the area of the peak, and the productivity thereof per medium was 0.73 mg/L.

Example 8-1

Construction of clone lacking ORFs 2, 4, 5 and 10

A BstBI(13085)-DraIII(13888) fragment (0.8 Kbp) in ORF 5 and a NheI(32521)-SpeI(34625) fragment (2.1 Kbp) containing ORF 10 were deleted from the plasmid pXA-NEB constructed in Example 7-1 to construct plasmid Δ2, 3, 4, 5, 10/pNEB.

A BstBI(8081)-EcoRI(9441) fragment (1.36 Kbp) of pEPA containing ORF 3 was inserted into SmaI-EcoRI site of PUC18 to construct ORF 3/pEC18. A PstI-PvuII fragment (1.57 Kbp) containing the ORF 3/pUC18 containing ORF 3 was inserted into Sse8387I-PmeI fragment of plasmid Δ2, 3, 4, 5, 10/pNEB to construct plasmid Δ2, 4, 5, 10/pNEB. *E. coli* JM109 was transformed with said Δ2, 4, 5, 10/pNEB, and the transformants were screened on an agar plate medium containing ampicillin to obtain a clone lacking ORFs 2, 4, 5 and 10. FIG. 3 shows the position on the XhoI-ArtII fragment of pEPA, of the fragments inserted in the plasmids.

Example 8-2

Production of eicosapentaenoic acid by clone lacking ORFs 2, 4, 5 and 10

The clone lacking ORFs 2, 4, 5 and 10, constructed in Example 8-1 was cultured in LB medium containing 50 μg/ml ampicillin according to the procedure as described in Example 5-2, and methyl esterification of lipid in the cells, an extraction with hexane and analysis by gas chromatography were carried out according to the procedure as described in Example 5-2. As a result, the ratio of the eicosapentaenoic acid per total fatty acid esters was calculated as 16.4% from the area of the peak. Productivity of eicosapentaenoic acid per culture medium was about 4.8 mg/L.

From the above-mentioned results of Examples 5 to 8, it was suggested that ORF 5 adversely acts on the synthesis of eicosapentaenoic acid, while ORF 4 and ORF 10 participate in the synthesis of eicosapentaenoic acid.

Example 9-1

Subcloning of each ORF

Among ORFs in the pEPA, ORFs 4, 7, 8 and 9 were separately subcloned into pUC118. For the ORFs 4, 8 and 9, DNA sequence upstream of the translation start codon was shortened by replacing with the synthesized DNA sequence by polymerase chain reaction (PCR). The length of the inserted region and its position in SEQ ID NO: 1 for each subclone are shown in Table 5, and primers used for construction of the subclones are shown in Table 6.

TABLE 5

| Plasmid | SEQ ID NO (ORF No.) | Length of Sequence inserted | Position in SEQ ID NO: |
|---|---|---|---|
| pUCP2 | 6 (4) | 3365 | 9573–12937 |
| pUCO5 | 12 (7) | 3430 | 22119–25548 |
| pUCP6 | 14 (8) | 7083 | 24364–31446 |
| pUCP7 | 16 (9) | 2144 | 30629–32772 |

TABLE 6

| Plasmid | SEQ ID NO | Primers | Sequence of primer (5' → 3') |
|---|---|---|---|
| pUCP2 | 20 | 1 | AGCTCAAACAACGCGCTTACA |
| | 21 | 2 | TGTTAGTCCCATCACGTTCTTG |
| pUCP6 | 22 | 1 | GCCATCATCAGGTGCCATTATCGGT |
| | 23 | 2 | GTCTGGGTAGGCGTGGAAGATT |
| pUCP7 | 24 | 1 | AGTATCTGCGTCCTAACTCGAT |
| | 25 | 2 | CCACCTGAATCGGCCTCTG |

Example 9-2

Preparation of proteins

The plasmid pXS-BS prepared in Example 4 and having an ability to synthesize eicosapentaenoic acid, and the subclones prepared in Example 9-1, were used to transform *E. coli* JM109, and the resulting transformants were cultured in 50 ml of LB-ampicillin medium at 25° C. for 24 hours with shaking. Each culture was centrifuged at 4° C., 3,000 rpm (Hitachi RPR-20-2) for 20 minutes to collect the microbial cells. The cells were suspended in 10 ml of 10 mM PKB (10 mM potassium phosphate buffer, pH 7.0, 2 mM β-mercaptoethanol, 10 mM EDTA), and the suspension was centrifuged at 4° C., 3,000 rpm for 10 minutes to wash the cells. The cell precipitate was suspended in 2 ml of 10 mM PKB, and sonicated. The sonicated cells were centrifuged at 4° C., 33,000 rpm (Backmann, SW55) for 80 minutes to obtain a supernatant, which was then used as an enzyme sample.

Example 9-3

Detection of activity of enzyme samples to extend carbon chain

A reaction mixture for an enzyme reaction contained [1-$^{14}$C]stearoyl-CoA (19 nmoles/μCi) and stearoyl-CoA (total concentration 25 μM), 25 μM malonyl-CoA, 100 μg *E. coli* acyl carrier-protein (ACP), 1.5 mM NADPH, 1.5 mM NADH, 10 μM cerulenin, 20 μM PMSF and 250 μg of a protein obtained Experiment 3, in 0.5 ml of 0.1M potassium phosphate buffer (pH 7.0). A reaction was carried out at 25° C. for 30 minutes with shaking.

The reaction mixture was lyophilized overnight, and to the lyophirizate was added 1 ml of 8% HCl-methanol, and the mixture was heated at 80° C. for one hour so as to esterify fatty acids produced during the enzyme reaction. The reaction mixture was extracted three times with 1 ml each of n-hexane, and the hexane layer was evaporated in vacuum. The residue was extracted three times with 0.2 ml each of n-hexane. After concentration of the n-hexane extract, a part of the concentrate as well as methyl stearate and methyl arachidate were spotted on a reverse phase TLC plate (MERCK RP-8$F_{254}$S), and developed three times with acetonitrile: water (7:1 v/v) for 25 minutes. Distribution of radioisotope on the TLC plate was detected by an AMBIS-RI imaging system and autoradiography.

As a result, protein preparations obtained from pUCO5 and pUCP6 provided spots near to position of methyl arachidate, which is formed by two carbon-extension of stearic acid. To identify the spots near to the position of methyl arachidate, radio gas chromatography (RGLC) was carried out. The detection was carried out with FID ($N_2$ 60 ml/min.) and an aeration type proportional counter (3,400V) at RI side ($CH_4$ 250 ml/min.). An amount of product from the TLC, corresponding to two thirds of a run of the reaction was applied to the RCLC. As a result, the protein products expressed by the plasmids pUCO5 and pUCP6, which comprise ORF 7 and ORF 8 respectively, provided peak corresponding to methyl arachidate. Radioactivity of the peak is shown in Table 7. Each of these ORFs has an ability to convert stearic acid (C18) to arachidic acid (C20) by 2-carbon extension.

TABLE 7

| Plasmid | ORF | CPM |
|---|---|---|
| pUCP2 | 4 | 15.8 |
| pUCO5 | 7 | 42.0 |
| pUCP6 | 8 | 29.0 |
| pUCP7 | 9 | 9.0 |

Reference to deposited microorganisms and the depository authority under the Rule 13-2

Depository authority: National Institute of Bioscience and Human-Technology Agency of Industrial Science and Technology Deposition Number and Deposition Date:

May 14, 1992 FERM BP-4257

We claim:

1. An isolated DNA comprising nucleotides 5661 to 34631 in SEQ ID NO: 1, coding for a group of eicosapentaenoic acid synthesis enzymes.

2. An isolated DNA comprising nucleotides 8081 to 9441, 12314 to 13084, and 13889 to 32520 in SEQ ID NO: 1, coding for a group of eicosapentaenoic acid synthesis enzymes.

3. An isolated DNA comprising nucleotides 8081 to 9441, 12314 to 13084, 13889 to 32520, and 34627 to 35559 in SEQ ID NO: 1, coding for a group of eicosapentaenoic acid synthesis enzymes.

4. An isolated DNA comprising nucleotides 8081 to 9441, 12314 to 13084, and 13889 to 35559 in SEQ ID NO: 1, coding for a group of eicosapentaenoic acid synthesis enzymes.

5. An isolated DNA comprising nucleotides 8081 to 9441, 9681 to 13084, and 13889 to 32520 in SEQ ID NO: 1, coding for a group of eicosapentaenoic acid synthesis enzymes.

6. An isolated DNA comprising nucleotides 8081 to 9441, 9681 to 13084, and 13889 to 32520, and 34627 to 35564, coding for a group of eicosapentaenoic acid synthesis enzymes.

7. An isolated DNA comprising nucleotides 8081 to 9441, 9681 to 13084, and 13889 to 35564, coding for a group of eicosapentaenoic acid synthesis enzymes.

8. An isolated DNA coding for a group of eicosapentaenoic acid synthesis enzymes comprising the amino acid sequences shown in SEQ ID NOs: 5, 11, 13, 15 and 17.

9. An isolated DNA comprising the nucleotide sequences shown in SEQ ID NOs: 4, 10, 12, 14 and 16, coding for a group of eicosapentaenoic acid synthesis enzymes.

10. An isolated DNA comprising a nucleotide sequence coding for an enzyme having an amino acid sequence shown in SEQ ID NO: 13 or 15, for elongating the chain of stearic acid to arachidic acid.

11. A plasmid comprising an isolated DNA according to claim 1.

12. A plasmid comprising an isolated DNA according to claim 10.

13. A host cell transformed with a plasmid according to claim 11.

14. A host cell transformed with a plasmid according to claim 12.

* * * * *